United States Patent [19]

Amann et al.

[11] Patent Number: 5,756,664
[45] Date of Patent: May 26, 1998

[54] PROTEIN WITH BONE FORMATION ABILITY AND PROCESS FOR ITS PRODUCTION

[75] Inventors: Egon Amann, Tokyo; Yoko Otawara-Hamamoto, Kamifukuoka; Reiko Kikuno; Sunao Takeshita, both of Tokorozawa; Kenichi Tezuka, Sakado, all of Japan

[73] Assignee: Hoechst Japan Limited, Tokyo, Japan

[21] Appl. No.: 426,627

[22] Filed: Apr. 21, 1995

Related U.S. Application Data

[63] Continuation of Ser. No. 36,841, Mar. 25, 1993, abandoned.

[30] Foreign Application Priority Data

Mar. 27, 1992 [JP] Japan .................................. 4-071501

[51] Int. Cl.⁶ .......................... C07K 14/435; C07K 14/51; C07K 14/475; C07K 7/08
[52] U.S. Cl. .......................... 530/326; 530/327; 530/350; 514/12; 435/69.1; 536/23.5
[58] Field of Search .................. 435/69.1; 514/2, 514/12; 530/300, 350, 326, 327; 536/22.1, 23.1, 23.5

[56] References Cited

FOREIGN PATENT DOCUMENTS

WO 92/00324  1/1992  Japan.

OTHER PUBLICATIONS

Takeshita et al. Biochem J. (1993) 294 271–278.
Tezuka et al BBRC. (1990) 173 246–251.
Zinn, K., et al., Cell, "Sequence Analysis and Neuronal expression of fasciclin I in grasshopper and drosophila", vol. 53:577–587 (May 20, 1988).
Tezuka, K., et al., Biochemical and Biophysical Research Communications, "Isolation of mouse and human cDNA clones encoding a protein expressed specifically in osteoblasts and brain tissues," vol. 173(1) 246–251 (Nov. 30, 1990).
European Search Report for Application No. 93104650.2.

*Primary Examiner*—Keith C. Furman
*Attorney, Agent, or Firm*—Finnegan, Henderson, Farabow, Garrett & Dunner, L.L.P.

[57] ABSTRACT

The present invention provides the sequence of the novel bone-related protein OSF-2 which can be obtained from mammalian bone tissues. The invention further provides a method of production of OSF-2 by recombinant techniques.

4 Claims, 5 Drawing Sheets

```
hOSF-2pl R1   --------- ---GIVGATT TQRYSD---- -ASKLREEIE GKGSFTYFAP
hOSF-2pl R2   ----GTSIQD FIEAEDDLSS FRAAAI---- -TSDILEALG RDGHFTLFAP
hOSF-2pl R3   --------- SAKQVIELAG KQQTTFTDLV AQLGLASALR PDGEYTLLAP
hOSF-2pl R4   ----EKSLHE KLKQDKRFST FLSLLE---- -AADLKELLT QPGDWTLFVP
dFas-1  R1   --AAAADLAD KLRDDSELSQ FYSLLE---- -SNQIANSTL SLRSCTIFVP
dFas-1  R2   --NPNALKFL KNAEEFNVDN IGVRTYRSQV TMAKKESVYD AAGOHTFLVP
dFas-1  R3   IDTTVTQFLQ SFKENAENGA LRKFYEVIMD NGGAVLDDIN SLTEVTILAP
dFas-1  R4   --------YT TVLGKLESDP MMSDTYKMGK FSHFNDQLNN TQRRFTYFVP
Consensus    .......... ......E... .......... .......... ..G..T.FAP
                                                              V hOSF-2pl R1   SNEAWD---- NLDSDIRRGL ESNVNVELLN ALHSHMINKR ML----TKDL
hOSF-2pl R2   TNEAFE---- KLPRGVLERF MGD-KVASEA LMKYHILNTL QC----SESI
hOSF-2pl R3   VNNAFS---- --DDTLSMVQ RLL-KLILQN ----HILKVK VG----LNEL
hOSF-2pl R4   TNDAFK---- GMTSEEKEIL IRD-KNALQN IILYHLTPGV FI----GKGF
dFas-1  R1   TNEAFQ---- ---------- RYKSKTA--- HVLYHITTEA YT----QKRL
dFas-1  R2   VDEGFK---- ---------L SARSSLVDGK VIDGHVIPNT VIFTAAAQHD
dFas-1  R3   SNEAWN---- --SSNINNVL RDRNK--MRQ ILNMHIIKDR LN----VDKI
dFas-1  R4   RDKGWQKTEL DYPSAHKK_F MADFSYHSKS ILERHLAISD KEYT--MKDL
Consensus    .NEAF..... ...S.....L ....K..... IL..HI.... ......K.L hOSF-2pl R1   K---NGMIIP SMYNNLGLFI N----HYPNG VVTVNCAR-- --IIHGNQIA
hOSF-2pl R2   M---GGAVF- -ETLEGNTIE I----GCDGD SITVNGIK-- --MVNKKDIV
hOSF-2pl R3   Y---NGQIL- -ETIGG---- -----KQLRV FVYRTAVC-- --IENSCMEK
hOSF-2pl R4   E---PGVTNI LKTTQGSKIF L----KEVND TLLVNELK-- ---SKESDIM
dFas-1  R1   P---NTVSSD -MAGNPPLYI T----KNSNG DIFVNNAR-- --IPSLSVE
dFas-1  R2   DPKASAAFED LLKVTVSFFK QKNGKMYVKS NTIVGDAKHR VGVVLAEIVK
dFas-1  R3   RQKNANLIAQ VPTVNNNTFL YFNVRGEGSD TVITVEG--- -GGVNATVIQ
dFas-1  R4   VKFSQESGSV ILPTFRDSLS IRVEEEAGRY VIIWNYKK-- -----INVYR
Consensus    .....G.... ..T.....F. .......... ...VN..K.. ...V....I.

hOSF-2pl R1   T-----NGVV HVIDRVLTQI   ( 85 - 212 )
hOSF-2pl R2   TN----NGVI HLIDQVLIPD   ( 213 - 347 )
hOSF-2pl R3   GSKQGRNGAI HIFREIIKPA   ( 348 - 474 )
hOSF-2pl R4   TT----NGVI HVVDKLLYPA   ( 475 - 610 )
dFas-1  R1   TNSDGKRQIM HIIDEVLEPL   (   1 - 130 )
dFas-1  R2   ANIPVSNGVV HLIHRPLMI-   ( 142 - 295 )
dFas-1  R3   ADVAQTNGYV HIIDHVLGVP   ( 296 - 449 )
dFas-1  R4   PDVECTNGII HVIDYPLLEE   ( 450 - 602 )
Consensus    T.....NGVI H.ID.VL.P.
```

Fig. 2

```
hOSF-2pl R1   ---------- ---GIVGATT TQRYSD---- -ASKLREEIE GKGSFTYFAP
hOSF-2pl R2   ----GTSIQD FIEAEDDLSS FRAAAI---- -TSDILEALG RDGHFTLFAP
hOSF-2pl R3   ---------- SAKQVIELAG KQQTTFTDLV AQLGLASALR PDGEYTLLAP
hOSF-2pl R4   ----EKSLHE KLKQDKRFST FLSLLE---- -AADLKELLT QPGDWTLFVP
dFas-1   R1   --AAAADLAD KLRDDSELSQ FYSLLE---- -SNQIANSTL SLRSCTIFVP
dFas-1   R2   --NPNALKFL KNAEEFNVDN IGVRTYRSQV TMAKKESVYD AAGQHTFLVP
dFas-1   R3   IDTTVTQFLQ SFKENAENGA LRKFYEVIMD NGGAVLDDIN SLTEVTILAP
dFas-1   R4   --------YT TVLGKLESDP MMSDTYKMGK FSHFNDQLNN TQRRFTYFVP
Consensus     .......... ......E... .......... .......... ..G..T.FAP
                                                                   V hOSF-2pl R1   SNEAWD---- NLDSDIRRGL ESNVNVELLN ALHSHMINKR ML----TKDL
hOSF-2pl R2   TNEAFE---- KLPRGVLERF MGD-KVASEA LMKYHILNTL QC----SESI
hOSF-2pl R3   VNNAFS---- --DDTLSMVQ RLL-KLILQN ----HILKVK VG----LNEL
hOSF-2pl R4   TNDAFK---- GMTSEEKEIL IRD-KNALQN IILYHLTPGV FI----GKGF
dFas-1   R1   TNEAFQ---- ---------- RYKSKTA--- HVLYHITTEA YT----QKRL
dFas-1   R2   VDEGFK---- ---------L SARSSLVDGK VIDGHVIPNT VIFTAAAQHD
dFas-1   R3   SNEAWN---- --SSNINNVL RDRNK--MRQ ILNMHIIKDR LN----VDKI
dFas-1   R4   RDKGWQKTEL DYPSAHKKLF MADFSYHSKS ILERHLAISD KEYT--MKDL
Consensus     .NEAF..... ...S.....L ....K..... IL..HI.... ........K.L hOSF-2pl R1   K---NGMIIP SMYNNLGLFI N----HYPNG VVTVNCAR-- --IIHGNQIA
hOSF-2pl R2   M---GGAVF- -ETLEGNTIE I----GCDGD SITVNGIK-- --MVNKKDIV
hOSF-2pl R3   Y---NGQIL- -ETIGG---- -----KQLRV FVYRTAVC-- --IENSCMEK
hOSF-2pl R4   E---PGVTNI LKTTQGSKIF L----KEVND TLLVNELK-- ---SKESDIM
dFas-1   R1   P---NTVSSD -MAGNPPLYI T----KNSNG DIFVNNAR-- --IIPSLSVE
dFas-1   R2   DPKASAAFED LLKVTVSFFK QKNGKMYVKS NTIVGDAKHR VGVVLAEIVK
dFas-1   R3   RQKNANLIAQ VPTVNNNTFL YFNVRGEGSD TVITVEG--- -GGVNATVIQ
dFas-1   R4   VKFSQESGSV ILPTFRDSLS IRVEEEAGRY VIIWNYKK-- -----INVYR
Consensus     .....G.... ..T.....F. .......... ...VN..K.. ...V....I.

hOSF-2pl R1   T-----NGVV HVIDRVLTQI    ( 85  - 212 )
hOSF-2pl R2   TN----NGVI HLIDQVLIPD    ( 213 - 347 )
hOSF-2pl R3   GSKQGRNGAI HIFREIIKPA    ( 348 - 474 )
hOSF-2pl R4   TT----NGVI HVVDKLLYPA    ( 475 - 610 )
dFas-1   R1   TNSDGKRQIM HIIDEVLEPL    (  1  - 130 )
dFas-1   R2   ANIPVSNGVV HLIHRPLMI-    ( 142 - 295 )
dFas-1   R3   ADVAQTNGYV HIIDHVLGVP    ( 296 - 449 )
dFas-1   R4   PDVECTNGII HVIDYPLLEE    ( 450 - 602 )
Consensus     T.....NGVI H.ID.VL.P.
```

Fig. 3

```
                    60                                                                              120
mOSF-2    MVPLLPLYALLLFLCDINPANANSYYDKVLAHSRIRGRDQGPNVCALQQILGTKKKYFSSCKNWYQGAICGKKTTVLYECCPGYMRMEGMKGCPAYMPIDHVYGTLGIVGATTTQHYSD
hOSF-2os  .I.F..MFS....LI--V..I...NH..I.........................................T....KKS...Q..............................L....R....
hOSF-2pl  .I.F..MFS....LI--V..I...NH..I.........................................T....KKS...Q..............................L....R....

180                                                                              240
mOSF-2    VSKLREEIEGKGSYTYFAPSNEAWENLDSDIRRGLENNVNVELLNALHSHMVNKRMLTKDLKHGMVIPSMYNNLGLFINHYPNGVTVNCARVIHGNQIATNGVHVIDRVLTQIGTSIQ
hOSF-2os  A......................F........D.......S.......................N.I..................I............................
hOSF-2pl  A......................F........D.......S.......................N.I..................I............................

300                                                                              360
mOSF-2    DFLEAEDDILSSFRAAAITSDLLESLGRDGHFTLFAPTNEAFEKLPRGVLERIMGDKVASEALMKYHILNTLQCSEAITGGAVFETMEGNTIEIGCEGDSISINGIKMVNKKDIVTKNGVI
hOSF-2os  ..I...................I..A...........................F...................S.M......L.........D...TV...............N......
hOSF-2pl  ..I...................I..A...........................F...................S.M......L.........D...TV...............N......

420                                                                              480
mOSF-2    HLIDEVLIPDSAKQVIELAGRKQQTTFTDLVAQIGLASSLKPDGEYTLLAPVNNAPSDDTLSMDQRLLKLIIQNHILKVKVGLSDLYNGQILETIGGKQLRVFVYRTAICIENSCMVRGSK
hOSF-2os  ......Q...................................A.R..........................V.......................NE.................V...EK...
hOSF-2pl  ......Q...................................A.R..........................V.......................NE.................V...EK...

540                                                                              600
mOSF-2    QGRNGAIHIFREIIQPAEKSLHDMLRQDKRFSIFLSLLEAADLKDLLTQPGDWTLFAPTNDAFKGMTSEERELLIGDKNALQNIILYHLTPGVYIGKGFEPGVTNILKTTQGSKIYLKGV
hOSF-2os  ..............K......E..K...T......E...........................V.............K.I..R..................P....................F..E.
hOSF-2pl  ..............K......E..K...T......E...........................V.............K.I..R..................P....................F..E.

660                                                                              720
mOSF-2    NETLLVNELASKESDIMTTNGVIHVVDKLLYPADIPVGNDQLLELLNLIKYIQIKPVRGSTFKEIPMTVR------------PAMTKIQIEGDPDFRLIKEGE
hOSF-2os  ...D.........................................T......I..............V...TTKIITKVEPKIKVIEGSLQPIIKTBG.TL..VK..E.E..........
hOSF-2pl  ...D.........................................T......I..............V...K..........................................

780                                                                              838
mOSF-2    TVTEVIHGEPVIKKYTKIIDGVPVEITEKQTRREERIITGPEIKYTRISTGGGETGKFLQKEVSKVTKFIEGGDGHLFEDEEIKRLLQGDTPAKKIPANKRVQGPRRRSREGRSQ
hOSF-2os  .I..................................E..................................E.K.L..E.T..................VR.LQ...K..S...L.....
hOSF-2pl  --I..................................E..................................E.K...E.T..................VR.LQ...K..S...L.....
```

1 thymus
2 spleen
3 brain
4 kidney
5 liver
6 lung
7 testis
8 heart
9 calvarial osteoblast-enriched cells
10 MC3T3-E1 cell cultured for 3 days
11 MC3T3-E1 cell cultured for 12 days
12 MC3T3-E1 cell cultured for 60 days
13 NIH3T3 cell

PROTEIN WITH BONE FORMATION ABILITY AND PROCESS FOR ITS PRODUCTION

This application is a continuation of application Ser. No. 08/036,841 filed Mar. 25, 1993, now abandoned.

The present invention provides the novel bone-related protein. The protein of the present invention is termed herein OSF-2, which can be obtained from mammalian bone tissues including mouse and human. The present invention further provides the method of production of OSF-2 by recombinant techniques.

Differential cell adhesion plays an extremely important role in various biological phenomena. For instance, cells of dissociated animal tissues can assemble autonomously and reform the original tissue-like structures (e.g., Moscona and Moscona (1952), J. Anat., vol.86, p287–301; Townes and Holtfreter (1955), J. Exp. Zool., vol.128, p53–120; Weiss and Taylor (1960), Proc. Natl. Acad. Sci. USA, vol.46, p1177–1185). In some animal species, dispersed embryonic cells can even reconstruct the complete embryonic body (e.g., Guidice (1962), Develop. Biol., vol.5, p402–411; Spiegel and Spiegel (1975), Am. Zool., vol.15, p583–606).

The construction of bio-tissues, thus, seems to depend at least partly upon the intrinsic morphogenetic capacity of individual cells. An important property of cells associated with their morphogenetic capacity is their ability to recognize identical or different cell types, adhering preferentially to their own type when mixed with others (e.g., Roth and Weston (1967), Proc. Natl. Acad. Sci. USA, vol.58, p974–980). Such selectivity in cell-cell adhesion probably plays a key role in the organization of tissues comprising multiple cell types. Various cell adhesion molecules have been identified (e.g., Damsky et al., (1984), "The Biology of Glycoproteins" (ed. R. J. Ivatt), p1–64, New York, Plenum Publishing Co.). For example, specific cell adhesion molecules can regulate the outgrowth and guidance of neuronal growth cones (Jessell (1988), Neuron, vol.1, p3–13).

Some other neuronal adhesion molecules have been identified that appear to help mediate axon outgrowth, guidance, and fasciculation in the developing vertebrate nervous system. Analysis of the genes encoding most of these proteins shows that each neural adhesion molecule thus far examined belongs to one of several families of cell adhesion molecules, including the neural cell adhesion molecule N-CAM, L1, contactin F11 and N-cadherin. Despite the large number of cell-specific adhesion molecules described to date, no such factor has been reported in bone cell biology.

The process of bone formation can be initiated by two different steps: 1) endochondral ossification and 2) intramembranous ossification. In the endochondral ossification process, cartilage is formed and calcified. The calcified cartilage is absorbed and finally replaced by the new bone. In the intramembranous ossification process, bone is formed directly in the primitive connective tissues. In both cases, invasion and assemble of osteoblasts in calcified cartilage or connective tissues is the first phenomenon of bone formation and, therefore, important for the ossification.

Luring and assembling of sufficient amounts of osteoblasts is essential for the effective usage of autocrine growth factors, such as bone morphogenetic proteins (BMP), insulin-like growth factor (IGF), and transforming growth factor-beta (TGF-β), etc. OSF-2 is a molecule that is indispensable for the chondrocyte and/or osteoblast assembling in the early stage of bone formation.

The present invention provides a class of mature native mammalian proteins (the class is termed herein as OSF-2), represented by native human and mouse OSF-2 described herein, which plays an important role in the formation of bone. OSF-2 acts as a growth factor or adhesion or "guiding" protein to attract cells involved in the bone formation process to the site of the bone induction. The human or mouse OSF-2 can be used to identify and isolate other mammalian OSF-2 proteins which may be homologous to human or mouse OSF-2 in their nucleotide and amino acid sequences.

The present invention further provides human and mouse analogues, such as mutants and fusion proteins. The present invention, furthermore, provides fragments of human and mouse OSF-2.

The present invention refers to the gene encoding the OSF-2 proteins herein said. The cDNA encoding the mouse OSF-2 isolated from the mouse osteoblastic cell line MC3T3E1 encodes a protein comprising 811 amino acids, including a 23 residue long signal sequence. The cDNA encoding the human OSF-2 isolated from a human placenta cDNA library encodes a protein comprising 779 amino acids, including a 21 residue signal sequence, and the cDNA encoding a second human OSF-2 variant isolated from a osteosarcoma cDNA library encodes a protein comprising 836 amino acids, including a 21 residues signal sequence. The present invention also provides the methods of preparation of OSF-2 by recombinant DNA techniques. The present invention, moreover, provides therapeutic compositions comprising OSF-2 in combination with other bone inducing proteins such as BMP.

The present invention refers to the proteins, such as mOSF-2 encoding from the 1st to the 788th amino acids in the Table 1a–e (SEQ ID NO:2), hOSF-2pl encoding from the 1st to the 758th amino acids in the Table 2a–d (SEQ ID NO:4), hOSF-2os encoding from the 1st to the 815th amino acids in the Table 3a–e (SEQ ID NO:6), the analogue thereof, or the fragments thereof.

Table 1a–e (SEQ ID NO:2) is an amino acid sequence of the cDNA and mOSF-2 encoding mouse OSF-2 (mOSF-2) isolated from the mouse osteoblastic cell line MC3T3E1. Amino acid residue NO: 1 corresponds to the predicted N-terminal residue of mature mOSF-2. mOSF-2 is a mature protein comprising 788 amino acids.

Table 2a–d (SEQ ID NO:4) is an amino acid sequence of the cDNA and hOSF-2pl encoding human placenta OSF-2 (hOSF-2pl) isolated from human placenta cDNA library. Amino acid residue NO: 1 corresponds to the predicted N-terminal residue of mature hOSF-2pl. hOSF-2pl is a mature protein comprising 758 amino acids.

Table 3a–e (SEQ ID NO:6) is an amino acid sequence of the CDNA and hOSF-2os encoding human osteosarcoma OSF-2 variant (hOSF-2os) isolated from human osteosarcoma cell line. Amino acid residue NO: 1 corresponds to the predicted N-terminal residue of mature hOSF-2os. hOSF-2os is a mature protein comprising 815 amino acids.

Three OSF-2 analogues herein said refer to the amino acid sequences that are modified by substitution, deletion, or addition. Therefore, it is obvious that the analogues contain the protein comprising the equal amino acid sequence herein to OSF-2.

Moreover, the analogues herein said are defined as the proteins with a major domain of these amino acid sequence to the extent that the OSF-2s herein said keep their own major character. As for the proteins, the comparison of the amino acid sequences among three proteins show an identity of 85% or more; preferably to 90% or more.

The analogues of the present invention include so-called a mutant whose character has been improved by modification of amino acid sequences. OSF-2 and the analogues of the present invention can be fused with other proteins to make a fusion protein. Therefore, the present invention also covers the fusion protein herein said.

The present invention further refers to the fragments of OSF-2 and the analogues herein said. At least 12 amino acid sequences of the fragments of the present invention contain the peptide fully equal to those of OSF-2 in part. The fragments herein said are used mainly as antigens. These fragments can be fused with other proteins to make a fusion protein. Therefore, the present invention also covers the fusion protein herein said.

OSF-2 has a typical signal sequence found in secreted proteins but lacks a typical transmembrane region. OSF-2 comprises four homologous repeats of approximately 130 amino acids each (FIG. 1).

FIG. 1 is a diagram of the structure of human placenta OSF-2. OSF-2 can be divided into seven segments; from N-terminal, a signal domain (shown by a shadowed box), a Cys-rich domain, four-fold repeating domains (R1 to R4) and C-terminal domain. Arrows show potential sites for N-linked glycosylation and 'C' denotes the location of Cys-residue. Two particularly conserved regions found in each repeating domain are represented by a dotted and a closed box.

A similar repeating structure has been reported for the insect fasciclin I protein (Zinn et al., (1988) Cell, vol.53, p577–587).

FIG. 2 is an alignment of amino acid sequences of the repeating domains (R1 to R4) between human OSF-2 (hOSF-2) and Drosophila fasciclin-I (dFas-1). The beginning and ending residue numbers of each domain were shown in the parenthesis after each sequence; the numbers were defined as 1 at the N-terminal residue of mature protein. Gaps (–) were inserted to get the maximum sequence similarity. Residues identical in at least four sequences are indicated in the line of consensus sequence. Two particularly conserved regions were boxed.

The regions of highly conserved amino acid similarity between OSF-2 and fasciclin I from Drosophila melanogaster are very short, approximately 10 amino acids, and limited only to the proposed domain structure (FIG. 2). Outside of these domains, no amino acid homology is observed. However, the similarity within the domains of OSF-2 and fasciclin I are significant and this similarity implies that there is a functional relationship between these proteins. It is, therefore, concluded that OSF-2 plays a similar role in bone as fasciclin I in neuronal development; namely the guidance of specialized cells to their promissing location. In contrast to fasciclin I however, OSF-2 has no apparent phosphatidylinositol lipid membrane anchor which is sometimes found in membrane-bound proteins devoid of a transmembrane region. On the other hand, OSF-2 displays a region of amphiphatic alpha-helical nature which might serve as a membrane anchor sequence.

FIG. 3 is an alignment of amino acid sequences of OSF-2 between mouse and human. Gaps (–) were inserted to align the sequence optimally. Residues of human OSF-2 which are identical to those of mouse are represented by dots.

Compared to mOSF-2, hOSF-2os displays an insertion of a stretch of 27 amino acids located outside of the four-fold repeating structure in the C-terminal domain. Compared to mOSF-2, hOSF-2pl, in contrast, displays a deletion of a stretch of 31 consecutive amino acids outside of the four-fold repeating structure next to the site of the insertion observed in hOSF-2os (FIG. 3).

OSF-2 is highly conserved between mouse and human. Comparison of the amino acid sequences between mOSF-2 and hOSF-2os shows homology of 89.2% between these two proteins (FIG. 3). If the protein signal sequences are excluded from the comparison, the amino acid homology reaches even up to 90.1%. It can be concluded from this high degree of conversation that OSF-2 plays an essential part in bone cell biology in vertebrates. Therefore, other members of OSF-2 family can be surely isolated from other vertebrate species from bone extracts and their amino acid sequences will be extremely identical to mOSF-2, hOSF-2pl or hOSF-2os. Therefore, the present invention covers the OSF-2 proteins isolated from other vertebrate species.

Employing recombinant DNA techniques, the genetic information of OSF-2 protein family members can be isolated by screening cDNA libraries prepared from bone directly, from cultured bone cells and from other body tissues or from genomic DNA libraries with the laid open OSF cDNAs or probes derived from these DNA sequences. Therefore, the present invention refers to the necessary DNA, the vector therein, and transformation cell containing the vector for the production of OSF-2 by gene technology. The present invention refers to the DNA encoding the OSF-2 protein.

The mouse OSF-2 (mOSF-2) cDNA was cloned from a cDNA library prepared from the mouse osteoblastic cell line MC3T3E1 by a subtraction hybridization method. Subsequently, the mouse OSF-2 cDNA was used to screen two human cDNA libraries prepared from placenta and osteosarcoma. From both libraries, two variant forms of human OSF-2 were isolated, termed hOSF-2pl and hOSF-2os, respectively, and sequenced. The cDNA sequences are shown in the Table 1a–e (SEQ ID NO:2), Table 2a–e (SEQ ID NO:4) and Table 3a–e (SEQ ID NO:6). The cDNA sequences herein did not show any homology to any other DNA sequences as present in the DNA databases.

In order to prepare OSF-2, DNA with signal sequence at N-terminal of mature OSF-2 is used. The signal sequence herein said is a part encoding from the –21st to the –1st amino acid sequences in Table 1a. The signal sequence in Table 2a and 3a is a part encoding from the –21st to the –1st amino acid sequence, respectively. In order to produce OSF-2 by yeast or by E. coli., the N-terminal encoding mature OSF-2 is linked to typical secreted N-terminal signal sequence of yeast or E. coli. OSF-2 and the analogues thereof are produced by recombinant techniques at the following processes.

(a) providing a population of cells comprising a heterologous DNA sequence, wherein said DNA sequence comprises:
 (i) transcriptional and translational control sequences functional in said cells,
 (ii) a coding sequence under the control of said transcriptional and translational sequences that encodes a polypeptide comprising mammalian OSF-2 and analogues thereof,
(b) cultivating said population of cells under conditions whereby said polypeptide is expressed.

The population of cells herein said can be used microorganisms such as yeast or E. coli., etc. or mammalian cells.

Applying recombinant DNA techniques, OSF-2 from other vertebrate species can be cloned by using probes derived from the cDNA or DNA fragments of the present invention, from cDNA libraries or genomic DNA libraries prepared from bone, cultured bone cells and other body tissues.

Synthetic peptides derived from hydrophobic regions of mOSF-2 were prepared, coupled to bovine albumin and used for immunization of rabbits. The anti-mOSF-2 antipeptide sera were employed for immunohistochemical detection of OSF-2 in newborn-rat-whole-body cutted sections. OSF-2 was detected in osteoblasts, chondrocytes and tongue.

In general, OSF-2 can be obtained directly by extraction from bone or cartilage of human, bovine, mouse or other sources with known biochemical techniques. Alternatively, DNA encoding OSF-2 can be obtained by constructing cDNA libraries from mRNA isolated from bones of the vertebrates, and screening with labeled DNA probes encoding portions of the human or mouse cDNA sequences disclosed in this specification. Assembly of full-length clones can be performed also by a combination of the above described and more standard molecular biology techniques.

OSF-2 disclosed in the present invention can be applied to pharmaceutical drug for metabolic bone diseases.

BRIEF EXPLANATION OF FIGURES

FIG. 2 is an alignment of amino acid sequences of the repeating domains (R1 to R4) between human OSF-2 (hOSF-2) and Drosophila fasciclin-I (dFas-1).

FIG. 2 illustrates the following sequences:

hOSF-2pl R1 (SEQ ID NO:14);

hOSF-2pl R2 (SEQ ID NO:15);

hOSF-2pl R3 (SEQ ID NO:16);

hOSF-2pl R4 (SEQ ID NO:17);

dFas-1 R1 (SEQ ID NO:18);

dFas-1 R2 (SEQ ID NO:19);

dFas-1 R3 (SEQ ID NO:20);

dFas-1 R4 (SEQ ID NO:21).

FIG. 3 is an alignment of amino acid sequences of OSF-2 between mouse and human. Gaps (−) were inserted to align the sequence optimally. Residues of human OSF-2 which are identical to those of mouse are represented by dots.

FIG. 3 shows the following sequences:

mOSF-2 (SEQ ID NO:22);

hOSF-2os (SEQ ID NO:23);

hOSF-2pl (SEQ ID NO:24).

Figure 1:
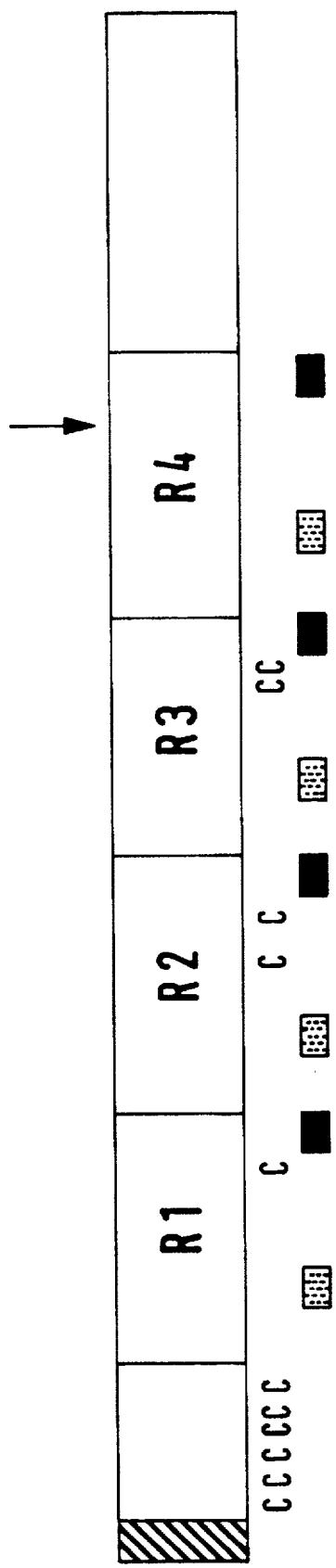
FIG. 1 is a diagram of the Structure of human placenta OSF-2.
Figure 4:
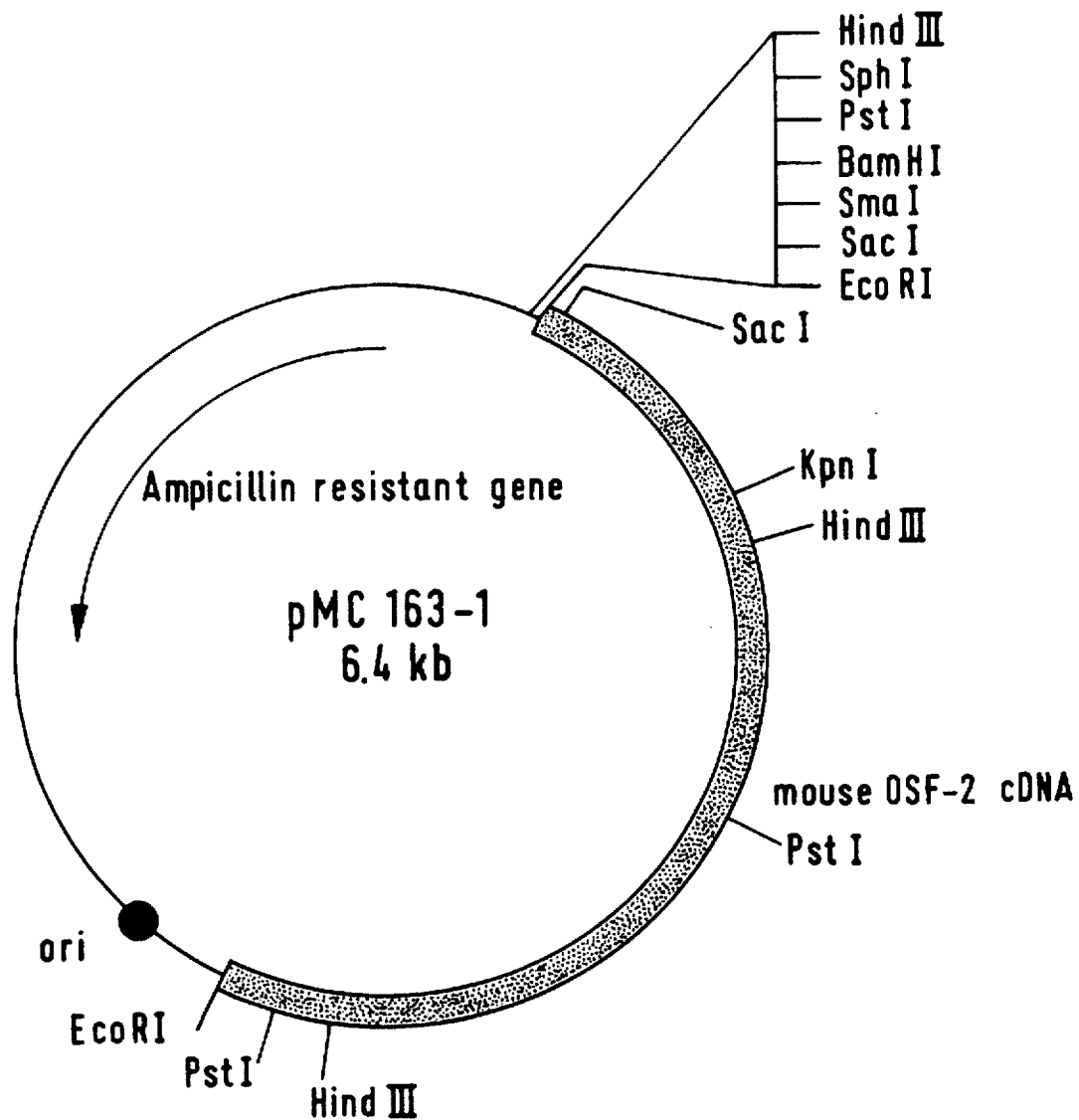

FIG. 4 is a restriction enzyme map of pMC163-1. Bold line is a mouse OSF-2 cDNA which was cloned into pUC118 vector. A arrow shows a location of Ampicillin resistant gene. A closed circle is a site of starting replication of the plasmid. A polylinker region and a restriction enzyme recognition site in the OSF-2 cDNA region, respectively, are also shown. pMC163-2, which is a similar plasmid to pMC163-1 was inserted in the same vector at the opposite direction.

Figure 5:
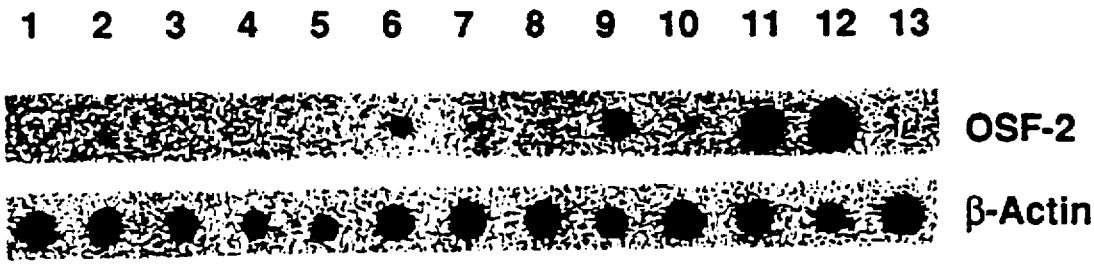

FIG. 5 is an autoradiography that shows the tissue-specific expression of mouse OSF-2. RNA was isolated from various tissues and cell lines and conducted by dot blot analysis according to Example 4 as described.

EXAMPLES

Example 1
Construction of a subtraction cDNA library

In this example, the construction of a specific cDNA library of mouse osteoblastic cell line MC3T3E1 is described. The cDNA library is a "subtraction library", from which all cDNA sequences in common with the fibroblastic cell line NIH3T3 and MC3T3E1 are subtracted.

All general recombinant DNA protocols were performed according to Sambrook et al. (1989), Molecular cloning manual, Cold Spring Harbor Laboratory, Cold Spring Harbor, otherwise indicated. Total RNAs were extracted by the guanidine method starting from 8×107 cells each, which were mouse osteoblastic cell line MC3T3E1 and mouse fibroblastic cell line NIH3T3 (ATCC CRL 1658), respectively. The mRNAs were purified from total RNAs by the "mRNA purification kit" from Pharmacia. Photobiotinylation, cDNA synthesis and subtraction hybridization protocols were performed according to the subtraction kit "Subtractor II from Invitrogen.

First, 100 mg of NIH3T3-derived mRNA was photobiotinylated. "First strand" cDNA was synthesized from 1.0 mg of MC3T3E1-derived mRNA. Photobiotinylated NIH3T3 mRNA and MC3T3E1 cDNA were mixed and hybridized, and then streptavidin was added to the hybridization mixture. The resulting photobiotinylated mRNA/cDNA hybrids (common sequences) were complexed with free streptavidin and removed from the hybridization mixture by standard phenol/chloroform extraction. The remaining cDNA molecules were converted to double-stranded form by "Second strand synthesis" and an EcoRI-NotI adaptor was ligated to the ends of the cDNA molecules using T4 DNA ligase.

The cDNA was ligated to the lambda gt10 cloning vector and packaged into lambda particles by the in vitro "Giga-pack" packaging kit. Recombinant phages were stored in SM buffer. The efficiency of this library was determined by infecting E. coli C600 (Japanese Cancer Research Resources Bank, National Institute of Health of Japan, HT003) with these phages, resulting in 2.8×107 phages/mg cDNA.

Example 2
Isolation of a mouse OSF-2 clone

In this example, the identification of OSF-2 cDNA as a MC3T3E1 specific clone by differential hybridization and its subcloning is described.

Using 1 mg of the mRNA prepared from MC3T3E1 or from NIH3T3 cells as described in Example 1, $^{32}$P labeled cDNA probe was synthesized using AMV reverse transcriptase. About 1.1×104 clones of the subtracted cDNA library prepared in Example 1 were plated and two nylon-membrane filters were used for replica transfers to be used for hybridization. Filter A was screened with the above radioactive cDNA probe prepared from MC3T3E1 mRNA and filter B was screened with the probe prepared from NIH3T3 mRNA.

155 clones were obtained which showed positive hybridization signals when they were hybridized with the MC3T3E1 probe and showed negative when hybridized with the NIH3T3 probe at the same time. These clones were selected and the recombinant phages thereof were amplified. The phage DNA of each clone was extracted with phenol. The phage DNA was precipitated with 70% ethanol and the DNA was digested with EcoRI. The cDNA inserts were fractioned by agarose gel electrophoresis and then purified. Aliquots of these individual cDNA inserts were used to prepare radioactive probes using the random primed DNA labeling kit (Boehringer Mannheim Yamanouchi).

0.3 mg of mRNA prepared from either MC3T3E1 cells or NIH3T3 cells was subjected to formaldehyde denaturing agarose gel electrophoresis and transferred to nylon membranes ("BYODYNE", Pall Bio Support, U.S.A.) by capillary blotting. The nylon filters were divided into equal stripes; each containing mRNA from both cell lines. Single stripes were hybridized with individual cDNA probes. One cDNA was termed MC163, which was hybridized specifically with the MC3T3E1 mRNA but was not hybridized with the NIH3T3 mRNA at the same time. This cDNA was cloned into pUC118 (purchased from Takara Shuzo). Then two orientations of the cDNA insert relative to the vector were recovered and the plasmid clones were termed pMC163-1 (FIG. 4) and pMC163-2, respectively. The hybridized mRNA was approximately 3.2 kb in size.

Example 3
DNA sequencing of mouse and human OSF-2

After the digestion of pMC163-1 and pMC163-2 with restriction enzymes, SphI and BamHI, 12 deletion mutants were constructed using the "Kilo sequence deletion kit" purchased from Takara Shuzo. The DNA sequences of both strands of these deletion mutants were determined using the automatic DNA sequencer model 370A from Applied Biosystems. Approximately 300 base pairs of the nucleotide sequence of each clone were determined, and the entire sequence of the cDNA was composed by combining the overlapping sequence data. The entire sequence and its deduced amino acid sequence are shown in the SEQ ID NO: 1 and SEQ ID NO:2 of the Sequence Listing, and the protein coded by this cDNA was designated as mouse OSF-2.

Example 4
Tissue specific expression of mouse OSF-2

RNA dot blotting was performed to examine the tissue specific expression of mouse OSF-2. Total RNA was prepared by the guanidine method from thymus, spleen, brain, kidney, liver, lung, testis and heart. Organs were prepared from ten 4-week-old mice. Calvarial osteoblast-enriched cells were prepared from primary culture of newborn ICR mice calvariae and its total RNA was prepared. 1.0 mg of RNA prepared from the above organs, from primary osteoblastic culture and from MC3T3E1 or NIH3T3 cells was dotted and fixed by baking at 80° C. on the BIODYNE nylon membrane. pMC163-1 was digested with EcoRI and the cDNA insert fragment was isolated by agarose gel electrophoresis. A radioactive probe was synthesized from this fragment by the "random primed DNA labeling kit" as mentioned above. RNA dot blot analysis indicated that high expression was observed in calvarial osteoblast-enriched cells and MC3T3E1, and rather low expression was observed in lung (FIG. 5).

Example 5
Cloning of cDNA encoding human OSF-2

Using the mouse OSF-2 cDNA which was prepared by EcoRI insert from pMC163-1 as hybridization probe, 1.5× 106 clones of human placenta cDNA phage library purchased from Clontech Co. and 1.3×105 clones of a human primary osteosarcoma cDNA phage library were screened. As a result, 72 positive clones from the placenta library and 31 positive clones from the osteosarcoma library were obtained. The seven clones showing the strongest signals from the placenta library and the five clones showing the strongest signals from the osteosarcoma library were amplified and their respective inserts were isolated. The largest inserts of each type were cloned into pUC118. The subclone resulted from the placenta library screen was termed pKOT133 and the one resulting from the osteosarcoma library screen was termed pKOT158, respectively.

Example 6
DNA sequence of human OSF-2

After the digestion of pKOT133 and pKOT158 with restriction enzymes such as SphI and XbaI, which were cloned according to Example 5 described above, the deletion mutants were constructed using the "Kilo sequence deletion kit". The DNA sequences of the cDNA inserts of pKOT133 and pKOT158 deletion mutants were determined using the automatic DNA sequencer model 373A from Applied Biosystems. Approximately 300 base pairs of nucleotide sequence of each clone were determined, and the entire sequence of the cDNA was composed by combining the overlapping sequence data. The entire sequences and their deduced amino acid sequences are shown in Tables 2a–e (SEQ ID NO:3 and SEQ ID NO:4) and 3a–e (SEQ ID NO:5 and SEQ ID NO:6).

EXAMPLE 7
Expression of OSF-2 in *E. coli*.

For the expression of mouse OSF-2 in *E. coli*, the pHSG741 plasmid vector (available from the Japanese Cancer Research Resources Bank, National Institute of Health of Japan, identification number VE040) was used. This vector employs the *E. coli* tryptophan (trp) promoter system and contains a polylinker region for the insertion of cloned DNA between the trp promoter and the rrnB transcriptional terminators. After digestion of pMC163-1 with ApaI and EcoRI (shown in FIG. 4), the slightly smaller ApaI-EcoRI fragment containing the cDNA fragment encoding the mature form of mouse OSF-2 was purified by using size fractionation of agarose gel. The following linker DNAs were synthesized on the automatic DNA synthesizer model 380 from Applied Biosystems and annealed.

TABLE 4

CATGCAACAGTTACTATGACAAGGTCCTGGCTCACAGCCGCATCAGGGGTCGG
GTTGTCAATGATACTGTTCCAGGACCGAGTGTCGGCGTAGTCCCCAGCC
GATCAGGGC 3' (SEQ ID NO: 7)
CTAGTC 5' (SEQ ID NO: 8)

After digestion of pHSG741 with NcoI and EcoRI, the large vector fragment was isolated and ligated with the above mentioned ApaI-EcoRI fragment containing the OSF-2 cDNA in the presence of the annealed synthetic linker described above by T4 DNA ligase. The resulting expression plasmid was termed pOSF2E1.

*E. coli* cells, strain W3110, were transformed with pOSF2E1 and ampicillin-resistant transformants were cultured in LB broth for 24 hours. The cells were inoculated into "minimal essential medium" and grown until the optical density measured to reach 0.9 at 550 nm. In order to induce the trp promoter, indolacrylic acid (IAA) was added at the same time as casamino acids and glucose. After culturing the cells for several hours, the *E. coli* cells were collected and lysed. The OSF-2 protein was detected in the intercellular fraction. pHSG741 is a suitable vector for the expression of OSF-2 in *E. coli*, and many different vectors can also be used for the expression of OSF-2 in *E. coli*.

Example 8
Expression of OSF-2 in yeast

For the expression of mouse OSF-2 in yeast, the pEMBLyex4 plasmid expression vector was used (Cesareni and Murray (1988), Genetic Engineering, vol.9, p135–154). pEMBLyex4 bears an inducible galactose promoter, a polylinker for the insertion of cloned genes, followed by a yeast transcription terminator and can efficiently express the cloned genes.

The OSF-2 cDNA was inserted into the polylinker of pEMBLyex4 as follows: pEMBLyex4 was digested with SacI and SphI and the larger vector fragment was purified by agarose gel electrophoresis. A SacI-SphI fragment containing the region fully encoding OSF-2 was isolated from pMC163-2 by the same method. These two fragments were ligated by T4 DNA ligase and the ligation mix was transformed into E. coli cells. A plasmid with the anticipated structure was identified, isolated, and termed pOSF2Y1.

Yeast cells were transformed with pOSF2Y1 and then the plasmid-bearing yeast cells were selected using the transformants' leucine and uracil prototrophy. These transformants were cultured in a yeast medium without leucine nor uracil. The OSF-2 protein was detected intercellularly in the yeast cells. Similar plasmid construction using yeast specific secretion signals can be used for the secretion of OSF-2 from yeast cells into the medium.

Example 9
Expression of OSF-2 in animal cells

The expression of OSF-2 in animal cell culture was performed according to the method described in Gene, vol. 71, p9–18 (1988). The mouse OSF-2 cDNA was inserted into the EcoRI site located in the cloning cassette of vector pHSG757 between the SV40 T antigen early promoter and the poly A signals. A plasmid clone with the insert in the right orientation for the expression of OSF-2 was designated as pOSF2A1.

An OSF-2 "expression unit fragment" shown in Table 5 contains multiple OSF-2 cDNA inserts in order to enhance the expression rate and has asymmetric cohesive ends which can be obtained by digesting pOSF2A1 with BstXI.

TABLE 5

| 5' | CTGG | | CCACGGG 3' |
|---|---|---|---|
| | OSF-2 Expression Unit | | |
| 3' CCCCGACC | | GGTG | 5' |

An isolated "OSF-2 expression unit fragment" as shown above was mixed with the isolated DNA fragment shown below, prepared from cosmid vector pHSG293 which is available from Japanese Cancer Research Resources Bank, National Institute of Health of Japan, identification number VE046 (Table 6).

TABLE 6

| 5' | CTGG | | CCACGGG 3' |
|---|---|---|---|
| | neo gene + cos site | | |
| 3' CCCCGACC | | GGTG | 5' |

Due to the existence of the asymmetrical BstXI site, approximately from 10 to 12 copies of the "head to tail ligation" OSF-2 cDNA can be present on one packed cosmid molecule. Isolated cosmid DNA, containing multiple copies of the mouse OSF-2 cDNA fragment, was transfected into Chinese Hamster Ovary (CHO) cells by the conventional calcium phosphate co-precipitation method. As a result, G418 resistant cells were selected and cloned using the "cloning cylinder" method.

As for 7 clones obtained, total RNA of each clone was prepared by the guanidine method and OSF-2 mRNA levels were determined by Northern blot analysis using radiolabeled OSF-2 cDNA as hybridization probe. The highest producer clones were cultured in alpha-MEM containing 10% fetal calf serum. In 24 hours, the expression of the OSF-2 protein came to be detected by Western blot analysis. After cell expansion, the OSF-2 protein could be isolated from the cells themselves or from the conditioned medium. Similar plasmid expression vectors and a variety of animal cell lines can be used for the expression of mouse and human OSF-2 in animal cells.

Example 10
Preparation of anti-OSF-2 antipeptide serum

Synthetic peptides, whose sequences were selected by the character of high antigenicity from the mouse OSF-2 amino acid sequence, were synthesized by the solid phase method using the 430A peptide synthesizer from Applied Biosystems. The synthesized peptides were coupled to ovalbumin as a carrier using glutaraldehyde as the coupling agent (Regenmortel et al. (1988), "Synthetic polypeptides as antigens", Burden and Knippenberg, Elsevier, p95–205) and used for immunization of rabbits. The synthetic peptides were: OSF-2.1 Table 7 (SEQ ID NO:9), OSF-2.2 Table 8 (SEQ ID NO:10), OSF-2.3 Table 9 (SEQ ID NO:11), OSF-2.4 Table 10 (SEQ ID NO:12), and OSF-2.5 Table 11 (SEQ ID NO:13). The anti-peptide sera obtained by the method described above were used to detect the existence of OSF-2 in new-born-rat-whole-body cuts immunologically and the expression of OSF-2 in E. coli, yeast and animal cells.

OSF-2 provided by the present invention can be used for the treatment of metabolic bone diseases. This OSF-2 herein said has high organ specificity to the bones and can be used for diagnostics of bone diseases.

TABLE 1a

SEQUENCE Description: SEQ ID NO: 1

| GAATTCGCGG | CCGCCGGAGC | TCAGGGCTGA | AG | ATG | GTT | CCT | CTC | CTG | CCC | TTA | 53 |
|---|---|---|---|---|---|---|---|---|---|---|---|
| | | | | Met | Val | Pro | Leu | Leu | Pro | Leu | |
| | | | | | | −20 | | | | | |

| TAT | GCT | CTG | CTG | CTG | CTG | TTC | CTG | TGT | GAT | ATT | AAC | CCT | GCA | AAT | GCC | 101 |
|---|---|---|---|---|---|---|---|---|---|---|---|---|---|---|---|---|
| Tyr | Ala | Leu | Leu | Leu | Leu | Phe | Leu | Cys | Asp | Ile | Asn | Pro | Ala | Asn | Ala | |
| | −15 | | | | | −10 | | | | −5 | | | | | | |

TABLE 1a-continued

| | | | | | | | | | | | | | | | | |
|---|---|---|---|---|---|---|---|---|---|---|---|---|---|---|---|---|
| AAC | AGT | TAC | TAT | GAC | AAG | GTC | CTG | GCT | CAC | AGC | CGC | ATC | AGG | GGT | CGG | 149 |
| Asn | Ser | Tyr | Tyr | Asp | Lys | Val | Leu | Ala | His | Ser | Arg | Ile | Arg | Gly | Arg | |
| 1 | | | | 5 | | | | | 10 | | | | | 15 | | |
| GAT | CAG | GGC | CCA | AAC | GTC | TGT | GCC | CTC | CAG | CAA | ATT | CTG | GGC | ACC | AAA | 197 |
| Asp | Gln | Gly | Pro | Asn | Val | Cys | Ala | Leu | Gln | Gln | Ile | Leu | Gly | Thr | Lys | |
| | | | 20 | | | | | 25 | | | | | | 30 | | |
| AAG | AAA | TAC | TTC | AGC | TCC | TGT | AAG | AAC | TGG | TAT | CAA | GGT | GCT | ATC | TGC | 245 |
| Lys | Lys | Tyr | Phe | Ser | Ser | Cys | Lys | Asn | Trp | Tyr | Gln | Gly | Ala | Ile | Cys | |
| | | 35 | | | | | 40 | | | | | 45 | | | | |
| GGG | AAG | AAA | ACC | ACT | GTG | CTA | TAT | GAA | TGC | TGC | CCT | GGC | TAT | ATG | AGA | 293 |
| Gly | Lys | Lys | Thr | Thr | Val | Leu | Tyr | Glu | Cys | Cys | Pro | Gly | Tyr | Met | Arg | |
| | 50 | | | | | 55 | | | | | 60 | | | | | |
| ATG | GAA | GGG | ATG | AAA | GGC | TGC | CCC | GCA | GTG | ATG | CCT | ATT | GAC | CAT | GTT | 341 |
| Met | Glu | Gly | Met | Lys | Gly | Cys | Pro | Ala | Val | Met | Pro | Ile | Asp | His | Val | |
| 65 | | | | | 70 | | | | | 75 | | | | | 80 | |
| TAT | GGC | ACG | CTG | GGC | ATT | GTG | GGA | GCC | ACT | ACC | ACT | CAG | CAC | TAC | TCC | 389 |
| Tyr | Gly | Thr | Leu | Gly | Ile | Val | Gly | Ala | Thr | Thr | Thr | Gln | His | Tyr | Ser | |
| | | | | 85 | | | | | 90 | | | | | 95 | | |
| GAT | GTC | TCG | AAG | CTG | AGA | GAA | GAG | ATT | GAA | GGA | AAA | GGG | TCA | TAC | ACG | 437 |
| Asp | Val | Ser | Lys | Leu | Arg | Glu | Glu | Ile | Glu | Gly | Lys | Gly | Ser | Tyr | Thr | |
| | | | 100 | | | | | 105 | | | | | 110 | | | |
| TAC | TTC | GCG | CCG | AGT | AAC | GAG | GCT | TGG | GAG | AAC | CTG | GAT | TCT | GAC | ATT | 485 |
| Tyr | Phe | Ala | Pro | Ser | Asn | Glu | Ala | Trp | Glu | Asn | Leu | Asp | Ser | Asp | Ile | |
| | | 115 | | | | | 120 | | | | | 125 | | | | |
| CGC | AGA | GGA | CTG | GAG | AAC | AAT | GTC | AAT | GTT | GAG | CTA | CTG | AAT | GCC | TTA | 533 |
| Arg | Arg | Gly | Leu | Glu | Asn | Asn | Val | Asn | Val | Glu | Leu | Leu | Asn | Ala | Leu | |
| | 130 | | | | | 135 | | | | | 140 | | | | | |

TABLE 1b

| | | | | | | | | | | | | | | | | |
|---|---|---|---|---|---|---|---|---|---|---|---|---|---|---|---|---|
| CAC | AGC | CAC | ATG | GTT | AAT | AAG | AGA | ATG | TTA | ACC | AAG | GAC | CTG | AAA | CAC | 581 |
| His | Ser | His | Met | Val | Asn | Lys | Arg | Met | Leu | Thr | Lys | Asp | Leu | Lys | His | |
| 145 | | | | | 150 | | | | | 155 | | | | | 160 | |
| GGC | ATG | GTT | ATT | CCT | TCA | ATG | TAC | AAC | AAT | CTG | GGG | CTT | TTT | ATT | AAC | 629 |
| Gly | Met | Val | Ile | Pro | Ser | Met | Tyr | Asn | Asn | Leu | Gly | Leu | Phe | Ile | Asn | |
| | | | | 165 | | | | | 170 | | | | | 175 | | |
| CAT | TAT | CCC | AAT | GGG | GTT | GTC | ACT | GTG | AAC | TGT | GCT | CGA | GTC | ATC | CAT | 677 |
| His | Tyr | Pro | Asn | Gly | Val | Val | Thr | Val | Asn | Cys | Ala | Arg | Val | Ile | His | |
| | | | 180 | | | | | 185 | | | | | 190 | | | |
| GGG | AAC | CAG | ATT | GCC | ACA | AAT | GGT | GTC | GTC | CAT | GTC | ATT | GAC | CGT | GTC | 725 |
| Gly | Asn | Gln | Ile | Ala | Thr | Asn | Gly | Val | Val | His | Val | Ile | Asp | Arg | Val | |
| | | 195 | | | | | 200 | | | | | 205 | | | | |
| CTG | ACA | CAA | ATT | GGT | ACC | TCC | ATC | CAA | GAC | TTC | CTT | GAA | GCA | GAA | GAC | 773 |
| Leu | Thr | Gln | Ile | Gly | Thr | Ser | Ile | Gln | Asp | Phe | Leu | Glu | Ala | Glu | Asp | |
| | 210 | | | | | 215 | | | | | 220 | | | | | |
| GAC | CTT | TCA | TCA | TTT | AGA | GCA | GCC | GCC | ATC | ACC | TCT | GAC | CTC | TTG | GAG | 821 |
| Asp | Leu | Ser | Ser | Phe | Arg | Ala | Ala | Ala | Ile | Thr | Ser | Asp | Leu | Leu | Glu | |
| 225 | | | | | 230 | | | | | 235 | | | | | 240 | |
| TCC | CTT | GGA | AGA | GAT | GGT | CAC | TTC | ACG | CTC | TTT | GCT | CCC | ACC | AAT | GAA | 869 |
| Ser | Leu | Gly | Arg | Asp | Gly | His | Phe | Thr | Leu | Phe | Ala | Pro | Thr | Asn | Glu | |
| | | | | 245 | | | | | 250 | | | | | 255 | | |
| GCT | TTC | GAG | AAA | CTG | CCA | CGA | GGT | GTC | CTA | GAA | AGG | ATC | ATG | GGA | GAC | 917 |
| Ala | Phe | Glu | Lys | Leu | Pro | Arg | Gly | Val | Leu | Glu | Arg | Ile | Met | Gly | Asp | |
| | | | 260 | | | | | 265 | | | | | 270 | | | |
| AAA | GTG | GCT | TCT | GAA | GCT | CTC | ATG | AAG | TAC | CAC | ATC | CTA | AAT | ACC | CTC | 965 |
| Lys | Val | Ala | Ser | Glu | Ala | Leu | Met | Lys | Tyr | His | Ile | Leu | Asn | Thr | Leu | |
| | | 275 | | | | | 280 | | | | | 285 | | | | |
| CAG | TGC | TCT | GAG | GCC | ATC | ACT | GGA | GGA | GCC | GTG | TTT | GAG | ACC | ATG | GAA | 1013 |
| Gln | Cys | Ser | Glu | Ala | Ile | Thr | Gly | Gly | Ala | Val | Phe | Glu | Thr | Met | Glu | |
| | 290 | | | | | 295 | | | | | 300 | | | | | |

TABLE 1b-continued

| | | | | | | | | | | | | | | | | |
|---|---|---|---|---|---|---|---|---|---|---|---|---|---|---|---|---|
| GGA | AAC | ACT | ATT | GAG | ATA | GGG | TGC | GAA | GGG | GAC | AGT | ATC | TCC | ATT | AAC | 1061 |
| Gly | Asn | Thr | Ile | Glu | Ile | Gly | Cys | Glu | Gly | Asp | Ser | Ile | Ser | Ile | Asn | |
| 305 | | | | 310 | | | | | 315 | | | | | 320 | | |
| GGA | ATC | AAG | ATG | GTG | AAC | AAG | AAA | GAC | ATT | GTG | ACT | AAG | AAT | GGT | GTC | 1109 |
| Gly | Ile | Lys | Met | Val | Asn | Lys | Lys | Asp | Ile | Val | Thr | Lys | Asn | Gly | Val | |
| | | | | 325 | | | | | 330 | | | | | 335 | | |
| ATC | CAC | CTG | ATT | GAT | GAA | GTC | CTC | ATT | CCT | GAT | TCT | GCC | AAA | CAA | GTT | 1157 |
| Ile | His | Leu | Ile | Asp | Glu | Val | Leu | Ile | Pro | Asp | Ser | Ala | Lys | Gln | Val | |
| | | | 340 | | | | | 345 | | | | | 350 | | | |

TABLE 1c

| | | | | | | | | | | | | | | | | |
|---|---|---|---|---|---|---|---|---|---|---|---|---|---|---|---|---|
| ATT | GAG | CTG | GCT | GGA | AAA | CAG | CAA | ACC | ACT | TTC | ACC | GAC | CTG | GTA | GCC | 1205 |
| Ile | Glu | Leu | Ala | Gly | Lys | Gln | Gln | Thr | Thr | Phe | Thr | Asp | Leu | Val | Ala | |
| | | 355 | | | | 360 | | | | | 365 | | | | | |
| CAA | TTA | GGC | TTG | GCA | TCC | TCT | CTG | AAG | CCA | GAT | GGA | GAG | TAC | ACC | TTA | 1253 |
| Gln | Leu | Gly | Leu | Ala | Ser | Ser | Leu | Lys | Pro | Asp | Gly | Glu | Tyr | Thr | Leu | |
| | 370 | | | | | 375 | | | | | 380 | | | | | |
| TTA | GCA | CCT | GTG | AAC | AAT | GCG | TTC | TCT | GAT | GAC | ACT | CTG | AGC | ATG | GAC | 1301 |
| Leu | Ala | Pro | Val | Asn | Asn | Ala | Phe | Ser | Asp | Asp | Thr | Leu | Ser | Met | Asp | |
| 385 | | | | | 390 | | | | | 395 | | | | | 400 | |
| CAA | CGC | CTT | CTT | AAG | CTA | ATT | CTG | CAA | AAT | CAC | ATA | TTG | AAA | GTA | AAA | 1349 |
| Gln | Arg | Leu | Leu | Lys | Leu | Ile | Leu | Gln | Asn | His | Ile | Leu | Lys | Val | Lys | |
| | | | | 405 | | | | | 410 | | | | | 415 | | |
| GTT | GGC | CTT | AGC | GAC | CTC | TAC | AAT | GGA | CAG | ATA | CTG | GAA | ACC | ATT | GGA | 1397 |
| Val | Gly | Leu | Ser | Asp | Leu | Tyr | Asn | Gly | Gln | Ile | Leu | Glu | Thr | Ile | Gly | |
| | | | 420 | | | | | 425 | | | | | 430 | | | |
| GGC | AAA | CAA | CTC | CGA | GTC | TTT | GTG | TAT | CGG | ACG | GCT | ATC | TGC | ATA | GAA | 1445 |
| Gly | Lys | Gln | Leu | Arg | Val | Phe | Val | Tyr | Arg | Thr | Ala | Ile | Cys | Ile | Glu | |
| | | 435 | | | | | 440 | | | | | 445 | | | | |
| AAC | TCA | TGC | ATG | GTG | AGA | GGA | AGC | AAG | CAG | GGA | AGG | AAT | GGT | GCC | ATT | 1493 |
| Asn | Ser | Cys | Met | Val | Arg | Gly | Ser | Lys | Gln | Gly | Arg | Asn | Gly | Ala | Ile | |
| | 450 | | | | | 455 | | | | | 460 | | | | | |
| CAC | ATA | TTC | CGA | GAA | ATC | ATC | CAA | CCA | GCA | GAG | AAA | TCC | CTG | CAC | GAC | 1541 |
| His | Ile | Phe | Arg | Glu | Ile | Ile | Gln | Pro | Ala | Glu | Lys | Ser | Leu | His | Asp | |
| 465 | | | | | 470 | | | | | 475 | | | | | 480 | |
| AAG | CTG | CGG | CAA | GAC | AAG | CGC | TTT | AGC | ATC | TTC | CTC | AGC | CTC | CTT | GAA | 1589 |
| Lys | Leu | Arg | Gln | Asp | Lys | Arg | Phe | Ser | Ile | Phe | Leu | Ser | Leu | Leu | Glu | |
| | | | | 485 | | | | | 490 | | | | | 495 | | |
| GCT | GCA | GAT | TTG | AAA | GAT | CTC | CTG | ACA | CAG | CCC | GGA | GAT | TGG | ACC | TTG | 1637 |
| Ala | Ala | Asp | Leu | Lys | Asp | Leu | Leu | Thr | Gln | Pro | Gly | Asp | Trp | Thr | Leu | |
| | | | 500 | | | | | 505 | | | | | 510 | | | |
| TTT | GCA | CCA | ACC | AAT | GAT | GCC | TTC | AAG | GGA | ATG | ACT | AGC | GAA | GAA | AGG | 1685 |
| Phe | Ala | Pro | Thr | Asn | Asp | Ala | Phe | Lys | Gly | Met | Thr | Ser | Glu | Glu | Arg | |
| | | 515 | | | | | 520 | | | | | 525 | | | | |
| GAG | CTT | CTG | ATT | GGG | GAT | AAA | AAT | GCT | CTC | CAA | AAC | ATC | ATT | CTT | TAT | 1733 |
| Glu | Leu | Leu | Ile | Gly | Asp | Lys | Asn | Ala | Leu | Gln | Asn | Ile | Ile | Leu | Tyr | |
| | 530 | | | | | 535 | | | | | 540 | | | | | |
| CAC | CTG | ACC | CCA | GGG | GTT | TAT | ATT | GGA | AAG | GGA | TTC | GAA | CCC | GGA | GTC | 1781 |
| His | Leu | Thr | Pro | Gly | Val | Tyr | Ile | Gly | Lys | Gly | Phe | Glu | Pro | Gly | Val | |
| 545 | | | | | 550 | | | | | 555 | | | | | 560 | |

TABLE 1d

| | | | | | | | | | | | | | | | | |
|---|---|---|---|---|---|---|---|---|---|---|---|---|---|---|---|---|
| ACT | AAT | ATC | CTG | AAG | ACC | ACA | CAG | GGA | AGC | AAA | ATC | TAT | CTG | AAA | GGA | 1829 |
| Thr | Asn | Ile | Leu | Lys | Thr | Thr | Gln | Gly | Ser | Lys | Ile | Tyr | Leu | Lys | Gly | |
| | | | | 565 | | | | | 570 | | | | | 575 | | |
| GTA | AAC | GAA | ACG | CTT | CTA | GTG | AAT | GAG | TTG | AAG | TCC | AAA | GAA | TCT | GAC | 1877 |
| Val | Asn | Glu | Thr | Leu | Leu | Val | Asn | Glu | Leu | Lys | Ser | Lys | Glu | Ser | Asp | |
| | | | 580 | | | | | 585 | | | | | 590 | | | |

TABLE 1d-continued

```
ATC ATG ACG ACA AAT GGT GTC ATC CAC GTC GTG GAC AAA CTC CTC TAT   1925
Ile Met Thr Thr Asn Gly Val Ile His Val Val Asp Lys Leu Leu Tyr
        595                 600                 605

CCA GCA GAT ATT CCA GTT GGA AAT GAT CAG CTC TTG GAA TTA CTG AAC   1973
Pro Ala Asp Ile Pro Val Gly Asn Asp Gln Leu Leu Glu Leu Leu Asn
        610                 615                 620

AAA CTG ATA AAA TAC ATC CAA ATC AAG TTT GTT CGT GGC AGC ACC TTC   2021
Lys Leu Ile Lys Tyr Ile Gln Ile Lys Phe Val Arg Gly Ser Thr Phe
625                 630                 635                 640

AAA GAA ATC CCC ATG ACT GTC TAT AGA CCT GCA ATG ACG AAG ATC CAA   2069
Lys Glu Ile Pro Met Thr Val Tyr Arg Pro Ala Met Thr Lys Ile Gln
                    645                 650                 655

ATT GAA GGT GAT CCC GAC TTC AGG CTG ATT AAA GAA GGC GAA ACG GTG   2117
Ile Glu Gly Asp Pro Asp Phe Arg Leu Ile Lys Glu Gly Glu Thr Val
                660                 665                 670

ACA GAA GTG ATC CAC GGA GAG CCA GTC ATT AAA AAG TAC ACC AAA ATC   2165
Thr Glu Val Ile His Gly Glu Pro Val Ile Lys Lys Tyr Thr Lys Ile
            675                 680                 685

ATA GAT GGA GTT CCT GTT GAA ATA ACT GAA AAA CAG ACT CGG GAA GAA   2213
Ile Asp Gly Val Pro Val Glu Ile Thr Glu Lys Gln Thr Arg Glu Glu
        690                 695                 700

CGA ATC ATT ACA GGT CCT GAG ATA AAA TAT ACC AGG ATT TCC ACA GGA   2261
Arg Ile Ile Thr Gly Pro Glu Ile Lys Tyr Thr Arg Ile Ser Thr Gly
705                 710                 715                 720

GGT GGA GAA ACA GGA GAG ACC TTG CAG AAA TTC TTG CAA AAA GAG GTC   2309
```

TABLE 1e

```
Gly Gly Glu Thr Gly Glu Thr Leu Gln Lys Phe Leu Gln Lys Glu Val
            725                 730                 735

TCC AAG GTC ACA AAG TTC ATT GAA GGT GGC GAT GGT CAC TTA TTT GAA   2357
Ser Lys Val Thr Lys Phe Ile Glu Gly Gly Asp Gly His Leu Phe Glu
                740                 745                 750

GAT GAG GAG ATT AAA AGA CTG CTT CAG GGA GAC ACA CCT GCA AAG AAG   2405
Asp Glu Glu Ile Lys Arg Leu Leu Gln Gly Asp Thr Pro Ala Lys Lys
            755                 760                 765

ATA CCA GCC AAC AAA AGG GTT CAA GGG CCT AGA AGA CGA TCA AGA GAA   2453
Ile Pro Ala Asn Lys Arg Val Gln Gly Pro Arg Arg Arg Ser Arg Glu
        770                 775                 780

GGC CGT TCT CAG TGA AAACCCAGAG GCCAGACCAC AGAGTTTATA TAATCCTAAA   2508
Gly Arg Ser Gln ***
785

TCAACGATCT GATTTTAAGG GAAATTGTAA GAGCCACCAC ACTGACTTCA GAATCTGAAA   2568
TGACAACCAA CAGAAGCCAA TCTTCAAGCA AGTCCAAACA CAGAGTTCAT GTCTTTGTTT   2628
CTGCATGAGA AATATAAGAA AATGATAGCT AGTCTCCTGT GGGGTAGGAA CTGAGGAAAT   2688
ATAGGACCAT GCAGGGATTT TATCTCAATG AGAAAACTTC TGATTAAAGT AGAATCCACC   2748
AAAGAACATC ATTGTGACTG GGTCCATACA GCTAAGTCTT TGCACAGTAA AAACCTTCCG   2808
CCTCAGGAAG AGGCTGGAAA AACCCAAAGC ACACAGTTAC CTTTCCAGGG GAGGCTAAGG   2868
TATCAAAAGG GGTGTTCAGT TATACAACAT GCAAACAAAC CTACCAAATT ACGAACAGTG   2928
GTGTTACATA TTTCTCATGC AATGTGGGTT TCCTGCTAAA TTTTGTTATT TTTACACTTG   2988
ATTTATATCC TCGAGATGAT TGTCATAAGC TTCTTGCAAT ACAAATGTTT TCTCTCAAAC   3048
ATTTCAATAA AACCATTCTT CAGGTATAAA GAGAATTACT GCAGAGTTGG TAATTCAGAA   3108
```

TABLE 1e-continued

```
AACTCAAGGT TTAAGTTAAA AGTGAGTTTA GACTTTGGAA TAGGACTTCA TACCTTTTTT    3168

TATTGTTAAC AAGTACTCAA TAAAGTAAAC TGAGCGGCCG CGAATTC                  3215
```

TABLE 2a

SEQUENCE Description: SEQ ID NO: 2:

```
GAATTCGGGG AACAGAACTG CAACGGAGAG ACTCAAG ATG ATT CCC TTT TTA CCC      55
                                         Met Ile Pro Phe Leu Pro
                                             -20

ATG TTT TCT CTA CTA TTG CTG CTT ATT GTT AAC CCT ATA AAC GCC AAC      103
Met Phe Ser Leu Leu Leu Leu Leu Ile Val Asn Pro Ile Asn Ala Asn
-15              -10                  -5                        1

AAT CAT TAT GAC AAG ATC TTG GCT CAT AGT CGT ATC AGG GGT CGG GAC      151
Asn His Tyr Asp Lys Ile Leu Ala His Ser Arg Ile Arg Gly Arg Asp
                5                10                  15

CAA GGC CCA AAT GCT TGT GCC CTT CAA CAG ATT TTG GGC ACC AAA AAG      199
Gln Gly Pro Asn Ala Cys Ala Leu Gln Gln Ile Leu Gly Thr Lys Lys
            20                25                  30

AAA TAC TTC AGC ACT TGT AAG AAC TGG TAT AAA AAG TCC ATC TGT GGA      247
Lys Tyr Phe Ser Thr Cys Lys Asn Trp Tyr Lys Lys Ser Ile Cys Gly
        35                40                  45

CAG AAA ACG ACT GTT TTA TAT GAA TGT TGC CCT GGT TAT ATG AGA ATG      295
Gln Lys Thr Thr Val Leu Tyr Glu Cys Cys Pro Gly Tyr Met Arg Met
50                    55                  60                  65

GAA GGA ATG AAA GGC TGC CCA GCA GTT TTG CCC ATT GAC CAT GTT TAT      343
Glu Gly Met Lys Gly Cys Pro Ala Val Leu Pro Ile Asp His Val Tyr
                70                  75                  80

GGC ACT CTG GGC ATC GTG GGA GCC ACC ACA ACG CAG CGC TAT TCT GAC      391
Gly Thr Leu Gly Ile Val Gly Ala Thr Thr Thrs Gln Arg Tyr Ser Asp
            85                  90                  95

GCC TCA AAA CTG AGG GAG GAG ATC GAG GGA AAG GGA TCC TTC ACT TAC      439
Ala Ser Lys Leu Arg Glu Glu Ile Glu Gly Lys Gly Ser Phe Thr Tyr
        100                   105                 110

TTT GCA CCG AGT AAT GAG GCT TGG GAC AAC TTG GAT TCT GAT ATC CGT      487
Phe Ala Pro Ser Asn Glu Ala Trp Asp Asn Leu Asp Ser Asp Ile Arg
    115                   120                 125

AGA GGT TTG GAG AGC AAC GTG AAT GTT GAA TTA CTG AAT GCT TTA CAT      535
Arg Gly Leu Glu Ser Asn Val Asn Val Glu Leu Leu Asn Ala Leu His
130                   135                 140                 145

AGT CAC ATG ATT AAT AAG AGA ATG TTG ACC AAG GAC TTA AAA AAT GGC      583
Ser His Met Ile Asn Lys Arg Met Leu Thr Lys Asp Leu Lys Asn Gly
```

TABLE 2b

```
                150                 155                   160

ATG ATT ATT CCT TCA ATG TAT AAC AAT TTG GGG CTT TTC ATT AAC CAT      631
Met Ile Ile Pro Ser Met Tyr Asn Asn Leu Gly Leu Phe Ile Asn His
            165                 170                 175

TAT CCT AAT GGG GTT GTC ACT GTT AAT TGT GCT CGA ATC ATC CAT GGG      679
Tyr Pro Asn Gly Val Val Thr Val Asn Cys Ala Arg Ile Ile His Gly
            180                 185                 190

AAC CAG ATT GCA ACA AAT GGT GTT GTC CAT GTC ATT GAC CGT GTG CTT      727
Asn Gln Ile Ala Thr Asn Gly Val Val His Val Ile Asp Arg Val Leu
        195                 200                 205
```

TABLE 2b-continued

| | | | | | | | | | | | | | | | | |
|---|---|---|---|---|---|---|---|---|---|---|---|---|---|---|---|---|
| ACA | CAA | ATT | GGT | ACC | TCA | ATT | CAA | GAC | TTC | ATT | GAA | GCA | GAA | GAT | GAC | 775 |
| Thr 210 | Gln | Ile | Gly | Thr | Ser 215 | Ile | Gln | Asp | Phe | Ile 220 | Glu | Ala | Glu | Asp | Asp 225 | |
| CTT | TCA | TCT | TTT | AGA | GCA | GCT | GCC | ATC | ACA | TCG | GAC | ATA | TTG | GAG | GCC | 823 |
| Leu | Ser | Ser | Phe | Arg 230 | Ala | Ala | Ala | Ile | Thr 235 | Ser | Asp | Ile | Leu | Glu 240 | Ala | |
| CTT | GGA | AGA | GAC | GGT | CAC | TTC | ACA | CTC | TTT | GCT | CCC | ACC | AAT | GAG | GCT | 871 |
| Leu | Gly | Arg | Asp 245 | Gly | His | Phe | Thr | Leu 250 | Phe | Ala | Pro | Thr | Asn 255 | Glu | Ala | |
| TTT | GAG | AAA | CTT | CCA | CGA | GGT | GTC | CTA | GAA | AGG | TTC | ATG | GGA | GAC | AAA | 919 |
| Phe | Glu | Lys 260 | Leu | Pro | Arg | Gly | Val 265 | Leu | Glu | Arg | Phe | Met 270 | Gly | Asp | Lys | |
| GTG | GCT | TCC | GAA | GCT | CTT | ATG | AAG | TAC | CAC | ATC | TTA | AAT | ACT | CTC | CAG | 967 |
| Val | Ala 275 | Ser | Glu | Ala | Leu | Met 280 | Lys | Tyr | His | Ile | Leu 285 | Asn | Thr | Leu | Gln | |
| TGT | TCT | GAG | TCT | ATT | ATG | GGA | GGA | GCA | GTC | TTT | GAG | ACG | CTG | GAA | GGA | 1015 |
| Cys 290 | Ser | Glu | Ser | Ile | Met 295 | Gly | Gly | Ala | Val | Phe 300 | Glu | Thr | Leu | Glu | Gly 305 | |
| AAT | ACA | ATT | GAG | ATA | GGA | TGT | GAC | GGT | GAC | AGT | ATA | ACA | GTA | AAT | GGA | 1063 |
| Asn | Thr | Ile | Glu | Ile 310 | Gly | Cys | Asp | Gly | Asp 315 | Ser | Ile | Thr | Val | Asn 320 | Gly | |
| ATC | AAA | ATG | GTG | AAC | AAA | AAG | GAT | ATT | GTG | ACA | AAT | AAT | GGT | GTG | ATC | 1111 |
| Ile | Lys | Met | Val 325 | Asn | Lys | Lys | Asp | Ile 330 | Val | Thr | Asn | Asn | Gly 335 | Val | Ile | |
| CAT | TTG | ATT | GAT | CAG | GTC | CTA | ATT | CCT | GAT | TCT | GCC | AAA | CAA | GTT | ATT | 1159 |
| His | Leu | Ile 340 | Asp | Gln | Val | Leu | Ile 345 | Pro | Asp | Ser | Ala | Lys 350 | Gln | Val | Ile | |
| GAG | CTG | GCT | GGA | AAA | CAG | CAA | ACC | ACC | TTC | ACG | GAT | CTT | GTG | GCC | CAA | 1207 |
| Glu | Leu | Ala 355 | Gly | Lys | Gln | Gln 360 | Thr | Thr | Phe | Thr | Asp 365 | Leu | Val | Ala | Gln | |

TABLE 2c

| | | | | | | | | | | | | | | | | |
|---|---|---|---|---|---|---|---|---|---|---|---|---|---|---|---|---|
| TTA | GGC | TTG | GCA | TCT | GCT | CTG | AGG | CCA | GAT | GGA | GAA | TAC | ACT | TTG | CTG | 1255 |
| Leu 370 | Gly | Leu | Ala | Ser | Ala 375 | Leu | Arg | Pro | Asp | Gly 380 | Glu | Tyr | Thr | Leu | Leu 385 | |
| GCA | CCT | GTG | ATT | AAT | GCA | TTT | TCT | GAT | GAT | ACT | CTC | AGC | ATG | GTT | CAG | 1303 |
| Ala | Pro | Val | Asn | Asn 390 | Ala | Phe | Ser | Asp | Asp 395 | Thr | Leu | Ser | Met | Val 400 | Gln | |
| CGC | CTC | CTT | AAA | TTA | ATT | CTG | CAG | AAT | CAC | ATA | TTG | AAA | GTA | AAA | GTT | 135 |
| Arg | Leu | Leu | Lys 405 | Leu | Ile | Leu | Gln | Asn 410 | His | Ile | Leu | Lys | Val 415 | Lys | Val | |
| GGC | CTT | AAT | GAG | CTT | TAC | AAC | GGG | CAA | ATA | CTG | GAA | ACC | ATC | GGA | GGC | 1399 |
| Gly | Leu | Asn | Glu 420 | Leu | Tyr | Asn | Gly | Gln 425 | Ile | Leu | Glu | Thr | Ile 430 | Gly | Gly | |
| AAA | CAG | CTC | AGA | GTC | TTC | GTA | TAT | CGT | ACA | GCT | GTC | TGC | ATT | GAA | AAT | 1447 |
| Lys | Gln 435 | Leu | Arg | Val | Phe | Val 440 | Tyr | Arg | Thr | Ala | Val 445 | Cys | Ile | Glu | Asn | |
| TCA | TGC | ATG | GAG | AAA | GGG | AGT | AAG | CAA | GGG | AGA | AAC | GGT | GCG | ATT | CAC | 1495 |
| Ser 450 | Cys | Met | Glu | Lys | Gly 455 | Ser | Lys | Gln | Gly | Arg 460 | Asn | Gly | Ala | Ile | His 465 | |
| ATA | TTC | CGC | GAG | ATC | ATC | AAG | CCA | GCA | GAG | AAA | TCC | CTC | CAT | GAA | AAG | 1543 |
| Ile | Phe | Arg | Glu | Ile 470 | Ile | Lys | Pro | Ala | Glu 475 | Lys | Ser | Leu | His | Glu 480 | Lys | |
| TTA | AAA | CAA | GAT | AAG | CGC | TTT | AGC | ACC | TTC | CTC | AGC | CTA | CTT | GAA | GCT | 1591 |
| Leu | Lys | Gln | Asp 485 | Lys | Arg | Phe | Ser | Thr 490 | Phe | Leu | Ser | Leu | Leu 495 | Glu | Ala | |
| GCA | GAC | TTG | AAA | GAG | CTC | CTG | ACA | CAA | CCT | GGA | GAC | TGG | ACA | TTA | TTT | 1639 |
| Ala | Asp | Leu 500 | Lys | Glu | Leu | Leu | Thr 505 | Gln | Pro | Gly | Asp | Trp 510 | Thr | Leu | Phe | |

TABLE 2c-continued

| | | | | | | | | | | | | | | | | |
|---|---|---|---|---|---|---|---|---|---|---|---|---|---|---|---|---|
| GTG | CCA | ACC | AAT | GAT | GCT | TTT | AAG | GGA | ATG | ACT | AGT | GAA | GAA | AAA | GAA | 1687 |
| Val | Pro 515 | Thr | Asn | Asp | Ala | Phe 520 | Lys | Gly | Met | Thr | Ser 525 | Glu | Glu | Lys | Glu | |
| ATT | CTG | ATA | CGG | GAC | AAA | AAT | GCT | CTT | CAA | AAC | ATC | ATT | CTT | TAT | CAC | 1735 |
| Ile 530 | Leu | Ile | Arg | Asp | Lys 535 | Asn | Ala | Leu | Gln | Asn 540 | Ile | Ile | Leu | Tyr | His 545 | |
| CTG | ACA | CCA | GGA | GTT | TTC | ATT | GGA | AAA | GGA | TTT | GAA | CCT | GGT | GTT | ACT | 1783 |
| Leu | Thr | Pro | Gly | Val 550 | Phe | Ile | Gly | Lys | Gly 555 | Phe | Glu | Pro | Gly | Val 560 | Thr | |
| AAC | ATT | TTA | AAG | ACC | ACA | CAA | GGA | AGC | AAA | ATC | TTT | CTG | AAA | GAA | GTA | 1831 |
| Asn | Ile | Leu | Lys 565 | Thr | Thr | Gln | Gly | Ser 570 | Lys | Ile | Phe | Leu | Lys 575 | Glu | Val | |
| AAT | GAT | ACA | CTT | CTG | GTG | AAT | GAA | TTG | AAA | TCA | AAA | GAA | TCT | GAC | ATC | 1879 |

TABLE 2d

| | | | | | | | | | | | | | | |
|---|---|---|---|---|---|---|---|---|---|---|---|---|---|---|
| Asn | Asp | Thr 580 | Leu | Leu | Val | Asn | Glu 585 | Leu | Lys | Ser | Lys | Glu 590 | Ser | Asp | Ile |

| | | | | | | | | | | | | | | | |
|---|---|---|---|---|---|---|---|---|---|---|---|---|---|---|---|
| ATG | ACA | ACA | AAT | GGT | GTA | ATT | CAT | GTT | GTA | GAT | AAA | CTC | CTC | TAT | CCA | 1927 |
| Met | Thr 595 | Thr | Asn | Gly | Val | Ile 600 | His | Val | Val | Asp | Lys 605 | Leu | Leu | Tyr | Pro |
| GCA | GAC | ACA | CCT | GTT | GGA | AAT | GAT | CAA | CTG | CTG | GAA | ATA | CTT | AAT | AAA | 1975 |
| Ala 610 | Asp | Thr | Pro | Val | Gly 615 | Asn | Asp | Gln | Leu | Leu 620 | Glu | Ile | Leu | Asn | Lys 625 |
| TTA | ATC | AAA | TAC | ATC | CAA | ATT | AAG | TTT | GTT | CGT | GGT | AGC | ACC | TTC | AAA | 2023 |
| Leu | Ile | Lys | Tyr | Ile 630 | Gln | Ile | Lys | Phe | Val 635 | Arg | Gly | Ser | Thr | Phe 640 | Lys |
| GAA | ATC | CCC | GTG | ACT | GTC | TAT | AAG | CCA | ATT | ATT | AAA | AAA | TAC | ACC | AAA | 2071 |
| Glu | Ile | Pro | Val 645 | Thr | Val | Tyr | Lys | Pro 650 | Ile | Ile | Lys | Lys | Tyr 655 | Thr | Lys |
| ATC | ATT | GAT | GGA | GTG | CCT | GTG | GAA | ATA | ACT | GAA | AAA | GAG | ACA | CGA | GAA | 2119 |
| Ile | Ile | Asp 660 | Gly | Val | Pro | Val | Glu 665 | Ile | Thr | Glu | Lys | Glu 670 | Thr | Arg | Glu |
| GAA | CGA | ATC | ATT | ACA | GGT | CCT | GAA | ATA | AAA | TAC | ACT | AGG | ATT | TCT | ACT | 2167 |
| Glu | Arg 675 | Ile | Ile | Thr | Gly | Pro 680 | Glu | Ile | Lys | Tyr | Thr 685 | Arg | Ile | Ser | Thr |
| GGA | GGT | GGA | GAA | ACA | GAA | GAA | ACT | CTG | AAG | AAA | TTG | TTA | CAA | GAA | GAG | 2215 |
| Gly 690 | Gly | Gly | Glu | Thr | Glu 695 | Glu | Thr | Leu | Lys | Lys 700 | Leu | Leu | Gln | Glu | Glu 705 |
| GTC | ACC | AAG | GTC | ACC | AAA | TTC | ATT | GAA | GGT | GGT | GAT | GGT | CAT | TTA | TTT | 2263 |
| Val | Thr | Lys | Val | Thr 710 | Lys | Phe | Ile | Glu | Gly 715 | Gly | Asp | Gly | His | Leu 720 | Phe |
| GAA | GAT | GAA | GAA | ATT | AAA | AGA | CTG | CTT | CAG | GGA | GAC | ACA | CCC | GTG | AGG | 2311 |
| Glu | Asp | Glu | Glu 725 | Ile | Lys | Arg | Leu | Leu 320 | Gln | Gly | Asp | Thr | Pro 735 | Val | Arg |
| AAG | TTG | CAA | GCC | AAC | AAA | AAA | GTT | CAA | GGT | TCT | AGA | AGA | CGA | TTA | AGG | 2359 |
| Lys | Leu | Gln 740 | Ala | Asn | Lys | Lys | Val 745 | Gln | Gly | Ser | Arg | Arg 750 | Arg | Leu | Arg |
| GAA | GGT | CGT | TCT | CAG | TGA | AAATCCAAAA | ACCAGAAAAA | AATGTTTATA | | | | | | | | 2407 |
| Glu | Gly | Arg | Ser | Gln 755 | *** | | | | | | | | | | | |

CAACCCTAAG TCAATAACCT GACCTTAGAA AATTGTGAGA GCCAAGTTGA CTTCAGGAAC 2467

TGAAACATCA GCACAAAGAA GCAATCATCA AATAATTCTG AACACAAATT TAATATTTTT 2527

TTTTCTGAAT GAGAAACATG AGGGAAATTG TGGAGTTAGC CTCCTGTGGA GTTAGCCTCC 2587

TGTGGTAAAG GAATTGAAGA AAATATAACA CCTTACACCC TTTTTCATCT TGACATTAAA 2647

AGTTCTGGCT AACTTTGGAA TCCATTAGAG AAAAATCCTT GTCACCAGAT TCATTACAAT 2707

TABLE 2e

| | | | | |
|---|---|---|---|---|
| TCAAATCGAA | GAGTTGTGAA | CTGTTATCCC | ATTGAAAAGA | CCGAGCCTTG TATGTATGTT 2767 |
| ATGGATACAT | AAAATGCACG | CAAGCCATTA | TCTCTCCATG | GGAAGCTAAG TTATAAAAAT 2827 |
| AGGTGCTTGG | TGTACAAAAC | TTTTTATATC | AAAAGGCTTT | GCACATTTCT ATATGAGTGG 2887 |
| GTTTACTGGT | AAATTATGTT | ATTTTTTACA | ACTAATTTTG | TACTCTCAGA ATGTTTGTCA 2947 |
| TATGCTTCTT | GCAATGCATA | TTTTTTAATC | TCAAACGTTT | CAATAAAACC ATTTTTCAGA 3007 |
| TATAAAGAGA | ATTACTTCAA | ATTGAGTAAT | TCAGAAAAAC | TCAAGATTTA AGTTAAAAAG 3067 |
| TGGTTTGGAC | TTGGGAACAG | GACTT | | 3092 |

TABLE 3a

SEQUENCE Description: SEQ ID NO: 3:

```
GAATTCGGAG ATCTACAGGG AGAGACTCAA G ATG ATT CCC TTT TTA CCC ATG   52
                                  Met Ile Pro Phe Leu Pro Met
                                  -20                     -15

TTT TCT CTA CTA TTG CTG CTT ATT GTT AAC CCT ATA AAC GCC AAC AAT  100
Phe Ser Leu Leu Leu Leu Leu Ile Val Asn Pro Ile Asn Ala Asn Asn
            -10                  -5                       1

CAT TAT GAC AAG ATC TTG GCT CAT AGT CGT ATC AGG GGT CGG GAC CAA  148
His Tyr Asp Lys Ile Leu Ala His Ser Arg Ile Arg Gly Arg Asp Gln
        5                   10                  15

GGC CCA AAT GTC TGT GCC CTT CAA CAG ATT TTG GGC ACC AAA AAG AAA  196
Gly Pro Asn Val Cys Ala Leu Gln Gln Ile Leu Gly Thr Lys Lys Lys
    20              25                  30

TAC TTC AGC ACT TGT AAG AAC TGG TAT AAA AAG TCC ATC TGT GGA CAG  244
Tyr Phe Ser Thr Cys Lys Asn Trp Tyr Lys Lys Ser Ile Cys Gly Gln
35              40              45                      50
```

TABLE 3b

```
AAA ACG ACT GTT TTA TAT GAA TGT TGC CCT GGT TAT ATG AGA ATG GAA
Lys Thr Thr Val Leu Tyr Glu Cys Cys Pro Gly Tyr Met Arg Met Glu
                55                  60                  65

GGA ATG AAA GGC TGC CCA GCA GTT TTG CCC ATT GAC CAT GTT TAT GGC
Gly Met Lys Gly Cys Pro Ala Val Leu Pro Ile Asp His Val Tyr Gly
            70                  75                  80

ACT CTG GGC ATC GTG GGA GCC ACC ACA ACG CAG CGC TAT TCT GAC GCC
Thr Leu Gly Ile Val Gly Ala Thr Thr Thr Gln Arg Tyr Ser Asp Ala
        85                  90                  95

TCA AAA CTG AGG GAG GAG ATC GAG GGA AAG GGA TCC TTC ACT TAC TTT  436
Ser Lys Leu Arg Glu Glu Ile Glu Gly Lys Gly Ser Phe Thr Tyr Phe
    100                 105                 110

GCA CCG AGT AAT GAG GCT TGG GAC AAC TTG GAT TCT GAT ATC CGT AGA  484
Ala Pro Ser Asn Glu Ala Trp Asp Asn Leu Asp Ser Asp Ile Arg Arg
115                 120                 125                 130

GGT TTG GAG AGC AAC GTG AAT GTT GAA TTA CTG AAT GCT TTA CAT AGT  532
Gly Leu Glu Ser Asn Val Asn Val Glu Leu Leu Asn Ala Leu His Ser
                137                 140                 145

CAC ATG ATT AAT AAG AGA ATG TTG ACC AAG GAC TTA AAA AAT GGC ATG  580
His Met Ile Asn Lys Arg Met Leu Thr Lys Asp Leu Lys Asn Gly Met
            150                 155                 160

ATT ATT CCT TCA ATG TAT AAC AAT TTG GGG CTT TTC ATT AAC CAT TAT  628
Ile Ile Pro Ser Met Tyr Asn Asn Leu Gly Leu Phe Ile Asn His Tyr
        165                 170                 175

CCT AAT GGG GTT GTC ACT GTT AAT TGT GCT CGA ATC ATC CAT GGG AAC  676
Pro Asn Gly Val Val Thr Val Asn Cys Ala Arg Ile Ile His Gly Asn
    180                 185                 190
```

TABLE 3b-continued

| | | | | | | | | | | | | | | | |
|---|---|---|---|---|---|---|---|---|---|---|---|---|---|---|---|
| CAG | ATT | GCA | ACA | AAT | GGT | GTT | GTC | CAT | GTC | ATT | GAC | CGT | GTG | CTT | ACA | 724 |
| Gln | Ile | Ala | Thr | Asn | Gly | Val | Val | His | Val | Ile | Asp | Arg | Val | Leu | Thr |
| 195 | | | | | 200 | | | | | 205 | | | | | 210 |

| | | | | | | | | | | | | | | | |
|---|---|---|---|---|---|---|---|---|---|---|---|---|---|---|---|
| CAA | ATT | GGT | ACC | TCA | ATT | CAA | GAC | TTC | ATT | GAA | GCA | GAA | GAT | GAC | CTT | 772 |
| Gln | Ile | Gly | Thr | Ser | Ile | Gln | Asp | Phe | Ile | Glu | Ala | Glu | Asp | Asp | Leu |
| | | | | 215 | | | | | 220 | | | | | 225 | |

| | | | | | | | | | | | | | | | |
|---|---|---|---|---|---|---|---|---|---|---|---|---|---|---|---|
| TCA | TCT | TTT | AGA | HCA | GCT | GCC | ATC | ACA | TCG | GAC | ATA | TTG | GAG | GCC | CTT | 820 |
| Ser | Ser | Phe | Arg | Ala | Ala | Ala | Ile | Thr | Ser | Asp | Ile | Leu | Glu | Ala | Leu |
| | | | 230 | | | | | 235 | | | | | 240 | | |

| | | | | | | | | | | | | | | | |
|---|---|---|---|---|---|---|---|---|---|---|---|---|---|---|---|
| GGA | AGA | GAC | GGT | CAC | TTC | ACA | CTC | TTT | GCT | CCC | ACC | AAT | GAG | GCT | TTT | 868 |
| Gly | Arg | Asp | Gly | His | Phe | Thr | Leu | Phe | Ala | Pro | Thr | Asn | Glu | Ala | Phe |
| | | 245 | | | | 250 | | | | | 255 | | | | |

| | | | | | | | | | | | | | | |
|---|---|---|---|---|---|---|---|---|---|---|---|---|---|---|
| GAG | AAA | CTT | CCA | CGA | GGT | GTC | CTA | GAA | AGG | TTC | ATG | GGA | GAC | AAA | GTG | 916 |

TABLE 3c

| | | | | | | | | | | | | | | |
|---|---|---|---|---|---|---|---|---|---|---|---|---|---|---|
| Glu | Lys | Leu | Pro | Arg | Gly | Val | Leu | Glu | Arg | Phe | Met | Gly | Asp | Lys | Val |
| | 260 | | | | | 265 | | | | | 270 | | | | |

| | | | | | | | | | | | | | | | |
|---|---|---|---|---|---|---|---|---|---|---|---|---|---|---|---|
| GCT | TCC | GAA | GCT | CTT | ATG | AAG | TAC | CAC | ATC | TTA | AAT | ACT | CTC | CAG | TGT | 964 |
| Ala | Ser | Glu | Ala | Leu | Met | Lys | Tyr | His | Ile | Leu | Asn | Thr | Leu | Gln | Cys |
| 275 | | | | | 280 | | | | | 285 | | | | | 290 |

| | | | | | | | | | | | | | | | |
|---|---|---|---|---|---|---|---|---|---|---|---|---|---|---|---|
| TCT | GAG | TCT | ATT | ATG | GGA | GGA | GCA | GTC | TTT | GAG | ACG | CTG | GAA | GGA | AAT | 1012 |
| Ser | Glu | Ser | Ile | Met | Gly | Gly | Ala | Val | Phe | Glu | Thr | Leu | Glu | Gly | Asn |
| | | | | 295 | | | | | 300 | | | | | 305 | |

| | | | | | | | | | | | | | | | |
|---|---|---|---|---|---|---|---|---|---|---|---|---|---|---|---|
| ACA | ATT | GAG | ATA | GGA | TGT | GAC | GGT | GAC | AGT | ATA | ACA | GTA | AAT | GGA | ATC | 1060 |
| Thr | Ile | Glu | Ile | Gly | Cys | Asp | Gly | Asp | Ser | Ile | Thr | Val | Asn | Gly | Ile |
| | | | 310 | | | | | 315 | | | | | 320 | | |

| | | | | | | | | | | | | | | | |
|---|---|---|---|---|---|---|---|---|---|---|---|---|---|---|---|
| AAA | ATG | GTG | AAC | AAA | AAG | GAT | ATT | GTG | ACA | AAT | AAT | GGT | GTG | ATC | CAT | 1108 |
| Lys | Met | Val | Asn | Lys | Lys | Asp | Ile | Val | Thr | Asn | Asn | Gly | Val | Ile | His |
| | | 325 | | | | | 330 | | | | | 335 | | | |

| | | | | | | | | | | | | | | | |
|---|---|---|---|---|---|---|---|---|---|---|---|---|---|---|---|
| TTG | ATT | GAT | CAG | GTC | CTA | ATT | CCT | GAT | TCT | GCC | AAA | CAA | GTT | ATT | GAG | 1156 |
| Leu | Ile | Asp | Gln | Val | Leu | Ile | Pro | Asp | Ser | Ala | Lys | Gln | Val | Ile | Glu |
| | 340 | | | | | 345 | | | | | 350 | | | | |

| | | | | | | | | | | | | | | | |
|---|---|---|---|---|---|---|---|---|---|---|---|---|---|---|---|
| CTG | GCT | GGA | AAA | CAG | CAA | ACC | ACC | TTC | ACG | GAT | CTT | GTG | GCC | CAA | TTA | 1204 |
| Leu | Ala | Gly | Lys | Gln | Gln | Thr | Thr | Phe | Thr | Asp | Leu | Val | Ala | Gln | Leu |
| 355 | | | | | 360 | | | | | 365 | | | | | 370 |

| | | | | | | | | | | | | | | | |
|---|---|---|---|---|---|---|---|---|---|---|---|---|---|---|---|
| GGC | TTG | GCA | TCT | GCT | CTG | AGG | CCA | GAT | GGA | GAA | TAC | ACT | TTG | CTG | GCA | 1252 |
| Gly | Leu | Ala | Ser | Ala | Leu | Arg | Pro | Asp | Gly | Glu | Tyr | Thr | Leu | Leu | Ala |
| | | | | 375 | | | | | 380 | | | | | 385 | |

| | | | | | | | | | | | | | | | |
|---|---|---|---|---|---|---|---|---|---|---|---|---|---|---|---|
| CCT | GTG | AAT | AAT | GCA | TTT | TCT | GAT | GAT | ACT | CTC | AGC | ATG | GTT | CAG | CGC | 1300 |
| Pro | Val | Asn | Asn | Ala | Phe | Ser | Asp | Asp | Thr | Leu | Ser | Met | Val | Gln | Arg |
| | | | 390 | | | | | 395 | | | | | 400 | | |

| | | | | | | | | | | | | | | | |
|---|---|---|---|---|---|---|---|---|---|---|---|---|---|---|---|
| CTC | CTT | AAA | TTA | ATT | CTG | CAG | AAT | CAC | ATA | TTG | AAA | GTA | AAA | GTT | GGC | 1348 |
| Leu | Leu | Lys | Leu | Ile | Leu | Gln | Asn | His | Ile | Leu | Lys | Val | Lys | Val | Gly |
| | | 405 | | | | | 410 | | | | | 415 | | | |

| | | | | | | | | | | | | | | | |
|---|---|---|---|---|---|---|---|---|---|---|---|---|---|---|---|
| CTT | AAT | GAG | CTT | TAC | AAC | GGG | CAA | ATA | CTG | GAA | ACC | ATC | GGA | GGC | AAA | 13 |
| Leu | Asn | Glu | Leu | Tyr | Asn | Gly | Gln | Ile | Leu | Glu | Thr | Ile | Gly | Gly | Lys |
| | | 420 | | | | 425 | | | | | 430 | | | | |

| | | | | | | | | | | | | | | | |
|---|---|---|---|---|---|---|---|---|---|---|---|---|---|---|---|
| CAG | CTC | AGA | GTC | TTC | GTA | TAT | CGT | ACA | GCT | GTC | TGC | ATT | GAA | AAT | TCA |
| Gln | Leu | Arg | Val | Phe | Val | Tyr | Arg | Thr | Ala | Val | Cys | Ile | Glu | Asn | Ser |
| 435 | | | | | 440 | | | | | 445 | | | | | 450 |

| | | | | | | | | | | | | | | | |
|---|---|---|---|---|---|---|---|---|---|---|---|---|---|---|---|
| TGC | ATG | GAG | AAA | GGG | AGT | AAG | CAA | GGG | AGA | AAC | GGT | GCG | ATT | CAC | ATA |
| Cys | Met | Glu | Lys | Gly | Ser | Lys | Gln | Gly | Arg | Asn | Gly | Ala | Ile | His | Ile |
| | | | | 455 | | | | | 460 | | | | | 465 | |

| | | | | | | | | | | | | | | |
|---|---|---|---|---|---|---|---|---|---|---|---|---|---|---|
| TTC | CGC | GAG | ATC | ATC | AAG | CCA | GCA | GAG | AAA | TCC | CTC | CAT | GAA | AAG | TTA |
| Phe | Arg | Glu | Ile | Ile | Lys | Pro | Ala | Glu | Lys | Ser | Leu | His | Glu | Lys | Leu |

TABLE 3d

|     |     |     | 470 |     |     |     | 275 |     |     |     |     | 480 |     |     |     |      |
|-----|-----|-----|-----|-----|-----|-----|-----|-----|-----|-----|-----|-----|-----|-----|-----|------|
| AAA | CAA | GAT | AAG | CGC | TTT | AGC | ACC | TTC | CTC | AGC | CTA | CTT | GAA | GCT | GCA | 1588 |
| Lys | Gln | Asp | Lys | Arg | Phe | Ser | Thr | Phe | Leu | Ser | Leu | Leu | Glu | Ala | Ala |      |
|     |     | 485 |     |     |     |     | 490 |     |     |     |     | 495 |     |     |     |      |
| GAC | TTG | AAA | GAG | CTC | CTG | ACA | CAA | CCT | GGA | GAC | TGG | ACA | TTA | TTT | GTG | 1636 |
| Asp | Leu | Lys | Glu | Leu | Leu | Thr | Gln | Pro | Gly | Asp | Trp | Thr | Leu | Phe | Val |      |
|     |     | 500 |     |     |     |     | 505 |     |     |     |     | 510 |     |     |     |      |
| CCA | ACC | AAT | GAT | GCT | TTT | AAG | GGA | ATG | ACT | AGT | GAA | GAA | AAA | GAA | ATT | 1684 |
| Pro | Thr | Asn | Asp | Ala | Phe | Lys | Gly | Met | Thr | Ser | Glu | Glu | Lys | Glu | Ile |      |
| 515 |     |     |     |     | 520 |     |     |     |     | 525 |     |     |     |     | 530 |      |
| CTG | ATA | CGG | GAC | AAA | AAT | GCT | CTT | CAA | AAC | ATC | ATT | CTT | TAT | CAC | CTG | 1732 |
| Leu | Ile | Arg | Asp | Lys | Asn | Ala | Leu | Gln | Asn | Ile | Ile | Leu | Tyr | His | Leu |      |
|     |     |     |     | 535 |     |     |     | 540 |     |     |     |     |     | 545 |     |      |
| ACA | CCA | GGA | GTT | TTC | ATT | GGA | AAA | GGA | TTT | GAA | CCT | GGT | GTT | ACT | AAC | 1780 |
| Thr | Pro | Gly | Val | Phe | Ile | Gly | Lys | Gly | Phe | Glu | Pro | Gly | Val | Thr | Asn |      |
|     |     |     | 550 |     |     |     |     | 555 |     |     |     |     | 560 |     |     |      |
| ATT | TTA | AAG | ACC | ACA | CAA | GGA | AGC | AAA | ATC | TTT | CTG | AAA | GAA | GTA | AAT | 1828 |
| Ile | Leu | Lys | Thr | Thr | Gln | Gly | Ser | Lys | Ile | Phe | Leu | Lys | Glu | Val | Asn |      |
|     |     | 565 |     |     |     |     | 570 |     |     |     |     | 575 |     |     |     |      |
| GAT | ACA | CTT | CTG | GTG | AAT | GAA | TTG | AAA | TCA | AAA | GAA | TCT | GAC | ATC | ATG | 1876 |
| Asp | Thr | Leu | Leu | Val | Asn | Glu | Leu | Lys | Ser | Lys | Glu | Ser | Asp | Ile | Met |      |
|     | 580 |     |     |     |     | 585 |     |     |     |     | 590 |     |     |     |     |      |
| ACA | ACA | AAT | GGT | GTA | ATT | CAT | GTT | GTA | GAT | AAA | CTC | CTC | TAT | CCA | GCA | 1924 |
| Thr | Thr | Asn | Gly | Val | Ile | His | Val | Val | Asp | Lys | Leu | Leu | Tyr | Pro | Ala |      |
| 595 |     |     |     |     | 600 |     |     |     |     | 605 |     |     |     |     | 610 |      |
| GAC | ACA | CCT | GTT | GGA | AAT | GAT | CAA | CTG | CTG | GAA | ATA | CTT | AAT | AAA | TTA | 1972 |
| Asp | Thr | Pro | Val | Gly | Asn | Asp | Gln | Leu | Leu | Glu | Ile | Leu | Asn | Lys | Leu |      |
|     |     |     |     | 615 |     |     |     |     | 620 |     |     |     |     | 625 |     |      |
| ATC | AAA | TAC | ATC | CAA | ATT | AAG | TTT | GTT | CGT | GGT | AGC | ACC | TTC | AAA | GAA | 2020 |
| Ile | Lys | Tyr | Ile | Gln | Ile | Lys | Phe | Val | Arg | Gly | Ser | Thr | Phe | Lys | Glu |      |
|     |     |     | 630 |     |     |     |     | 635 |     |     |     | 640 |     |     |     |      |
| ATC | CCC | GTG | ACT | GTC | TAT | ACA | ACT | AAA | ATT | ATA | ACC | AAA | GTT | GTG | GAA | 2068 |
| Ile | Pro | Val | Thr | Val | Tyr | Thr | Thr | Lys | Ile | Ile | Thr | Lys | Val | Val | Glu |      |
|     |     | 645 |     |     |     |     | 650 |     |     |     |     | 655 |     |     |     |      |
| CCA | AAA | ATT | AAA | GTG | ATT | GAA | GGC | AGT | CTT | CAG | CCT | ATT | ATC | AAA | ACT | 2116 |
| Pro | Lys | Ile | Lys | Val | Ile | Glu | Gly | Ser | Leu | Gln | Pro | Ile | Ile | Lys | Thr |      |
|     | 660 |     |     |     |     | 665 |     |     |     |     | 670 |     |     |     |     |      |
| GAA | GGA | CCC | ACA | CTA | ACA | AAA | GTC | AAA | ATT | GAA | GGT | GAA | CCT | GAA | TTC | 2164 |
| Glu | Gly | Pro | Thr | Leu | Thr | Lys | Val | Lys | Ile | Glu | Gly | Glu | Pro | Glu | Phe |      |
| 675 |     |     |     |     | 680 |     |     |     |     | 685 |     |     |     |     | 690 |      |

TABLE 3e

| AGA | CTG | ATT | AAA | GAA | GGT | GAA | ACA | ATA | ACT | GAA | GTG | ATC | CAT | GGA | GAG |     | 2212 |
|-----|-----|-----|-----|-----|-----|-----|-----|-----|-----|-----|-----|-----|-----|-----|-----|-----|------|
| Arg | Leu | Ile | Lys | Glu | Gly | Glu | Thr | Ile | Thr | Glu | Val | Ile | His | Gly | Glu |     |      |
|     |     |     |     | 695 |     |     |     | 700 |     |     |     |     |     | 705 |     |     |      |
| CCA | ATT | ATT | AAA | AAA | TAC | ACC | AAA | ATC | ATT | GAT | GGA | GTG | CCT | GTG | GAA |     | 2260 |
| Pro | Ile | Ile | Lys | Lys | Tyr | Thr | Lys | Ile | Ile | Asp | Gly | Val | Pro | Val | Glu |     |      |
|     |     |     | 710 |     |     |     |     | 715 |     |     |     |     | 720 |     |     |     |      |
| ATA | ACT | GAA | AAA | GAG | ACA | CGA | GAA | GAA | CGA | ATC | ATT | ACA | GGT | CCT | GAA |     | 2308 |
| Ile | Thr | Glu | Lys | Glu | Thr | Arg | Glu | Glu | Arg | Ile | Ile | Thr | Gly | Pro | Glu |     |      |
|     |     | 725 |     |     |     |     | 730 |     |     |     |     | 735 |     |     |     |     |      |
| ATA | AAA | TAC | ACT | AGG | ATT | TCT | ACT | GGA | GGT | GGA | GAA | ACA | GAA | GAA | ACT |     | 2356 |
| Ile | Lys | Tyr | Thr | Arg | Ile | Ser | Thr | Gly | Gly | Gly | Glu | Thr | Glu | Glu | Thr |     |      |
|     | 740 |     |     |     |     | 745 |     |     |     |     | 750 |     |     |     |     |     |      |
| CTG | AAG | AAA | TTG | TTA | CAA | GAA | GAG | GTC | ACC | AAG | GTC | ACC | AAA | TTC | ATT |     | 2404 |
| Leu | Lys | Lys | Leu | Leu | Gln | Glu | Glu | Val | Thr | Lys | Val | Thr | Lys | Phe | Ile |     |      |
| 755 |     |     |     |     | 760 |     |     |     |     | 765 |     |     |     |     | 770 |     |      |

TABLE 3e-continued

| | | | | | | | | | | | | | | | | |
|---|---|---|---|---|---|---|---|---|---|---|---|---|---|---|---|---|
| GAA | GGT | GGT | GAT | GGT | CAT | TTA | TTT | GAA | GAT | GAA | GAA | ATT | AAA | AGA | CTG | 2452 |
| Glu | Gly | Gly | Asp | Gly 775 | His | Leu | Phe | Glu | Asp 780 | Glu | Glu | Ile | Lys | Arg 785 | Leu | |
| CTT | CAG | GGA | GAC | ACA | CCC | GTG | AGG | AAG | TTG | CAA | GCC | AAC | AAA | AAA | GTT | 2500 |
| Leu | Gln | Gly | Asp 790 | Thr | Pro | Val | Arg | Lys 795 | Leu | Gln | Ala | Asn | Lys 800 | Lys | Val | |
| CAA | GGT | TCT | AGA | AGA | CGA | TTA | AGG | GAA | GGT | CGT | TCT | CAG | TGA | | | 2542 |
| Gln | Gly | Ser 805 | Arg | Arg | Arg | Leu | Arg 810 | Glu | Gly | Arg | Ser | Gln 815 | *** | | | |

AAATCCAAAA ACCAGAAAAA AATGTTTATA CAACCCTAAG TCAATAACCT GACCTTAGAA 2602

AATTGTGAGA GCCAAGTTGA CTTCAGGAAC TGAAACATCA GCACAAAGAA GCAATCATCA 2662

AATAATTCTG AACACAAATT TAATATTTTT TTTTCTGAAT GAGAAACATG AGGGAAATTG 2722

TGGAGTTAGC CTCCTGTGGT AAAGGAATTG AAGAAAATAT AACACCTTAC ACCCTTTTTC 2782

ATCTTGACAT TAAAAGTTCT GGCTAACTTT GGAATCCATT AGAGAAAAAT CCTTGTCACC 2842

AGATTCATTA CAATTCAAAT CGAAGAGTTG TGAACTGTTA TCCCATTGAA AAGACCGAGC 2902

CTTGTATGTA TGTTATGGAT ACATAAAATG CACGCAAGCC ATTATCTCTC CATGGGAAGC 2962

TAAGTTATAA AAATAGGTGC TTGGTGTACA AAACTTTTTA TATCAAAAGG CTTTGCACAT 3022

TTCTATATGA GTGGGTTTAC TGGTAAATTA TGTTATTTTT TACAACTAAT TTTGTACTCT 3082

CAGAATGTTT GTCATATGCT TCTTGCAATG CATATTTTTT AATCTCAAAC GTTTCAATAA 3142

AACCATTTTT CAGATATAAA GAGAATTACT TCAAATTGAG TAATTCAGAA AAACTCAAGA 3202

TTTAAGTTAA AAAGTGGTTT GGACTTGGGA ACCCTGTAGA TCTCCGAATT C 3253

TABLE 7

FEATURE: OSF-2.1 (antigen peptide)
LOCATION:
  segment of mouse OSF-2 from the 122nd to the 137th amino acid residue
SEQUENCE Description: SEQ ID NO: 6:

Glu Asn Leu Asp Ser Asp Ile Arg Arg Gly Leu Glu Asn Asn Val Asn
              5                  10                  15

TABLE 8

FEATURE: OSF-2.2 (antigen peptide)
LOCATION:
  segment of mouse OSF-2 from the 475th to the 487th amino acid residue
SEQUENCE Description: SEQ ID NO: 7:

Glu Lys Ser Leu His Asp Lys Leu Arg Gln Asp Lys Arg
              5                  10

TABLE 9

FEATURE: OSF-2.3 (antigen peptide)
LOCATION:
  segment of mouse OSF-2 from the 772nd to the 787th amino acid residue
SEQUENCE Description: SEQ ID NO: 8:

Asn Lys Arg Val Gln Gly Pro Arg Arg Arg Ser Arg Glu Gly Arg Ser
              5                  10                  15

TABLE 10

FEATURE: OSF-2.4 (antigen peptide)
LOCATION:
  segment of mouse OSF-2 from the 246th to the 261st amino acid residue
SEQUENCE Description: SEQ ID NO: 9:

Gly His Phe Thr Leu Phe Ala Pro Thr Asn Glu Ala Phe Glu Lys Leu
              5                  10                  15

TABLE 11

FEATURE: OSF-2.5 (antigen peptide)
LOCATION:
  segment of mouse OSF-2 from the 330th to the 347th amino acid residue
SEQUENCE Description: SEQ ID NO: 10:

Ile Val Thr Lys Asn Gly Val Ile His Leu Ile Asp Glu Val Leu Ile
              5                  10                  15
Pro Asp

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
      ( A ) LENGTH: 3215 base pairs
      ( B ) TYPE: nucleic acid
      ( C ) STRANDEDNESS: double
      ( D ) TOPOLOGY: linear ( i i ) MOLECULE TYPE: cDNA to mRNA ( v i ) ORIGINAL SOURCE:
      ( A ) ORGANISM: Mus musculus
      ( B ) STRAIN: osteoblastic cell line MC3T3E1

( i x ) FEATURE:
      ( A ) NAME/KEY: CDS
      ( B ) LOCATION: join(33..2466)

( i x ) FEATURE:
      ( A ) NAME/KEY: mat_peptide
      ( B ) LOCATION: join(104..2466)

( x i ) SEQUENCE DESCRIPTION: SEQ ID NO:1:

```
GAATTCGCGG CCGCCGGAGC TCAGGGCTGA AG ATG GTT CCT CTC CTG CCC TTA      53
                                    Met Val Pro Leu Leu Pro Leu
                                    -23         -20

TAT GCT CTG CTG CTG CTG TTC CTG TGT GAT ATT AAC CCT GCA AAT GCC     101
Tyr Ala Leu Leu Leu Leu Phe Leu Cys Asp Ile Asn Pro Ala Asn Ala
    -15                 -10                      -5

AAC AGT TAC TAT GAC AAG GTC CTG GCT CAC AGC CGC ATC AGG GGT CGG     149
Asn Ser Tyr Tyr Asp Lys Val Leu Ala His Ser Arg Ile Arg Gly Arg
  1           5                   10                  15

GAT CAG GGC CCA AAC GTC TGT GCC CTC CAG CAA ATT CTG GGC ACC AAA     197
Asp Gln Gly Pro Asn Val Cys Ala Leu Gln Gln Ile Leu Gly Thr Lys
            20                  25                  30

AAG AAA TAC TTC AGC TCC TGT AAG AAC TGG TAT CAA GGT GCT ATC TGC     245
Lys Lys Tyr Phe Ser Ser Cys Lys Asn Trp Tyr Gln Gly Ala Ile Cys
        35                  40                  45

GGG AAG AAA ACC ACT GTG CTA TAT GAA TGC TGC CCT GGC TAT ATG AGA     293
Gly Lys Lys Thr Thr Val Leu Tyr Glu Cys Cys Pro Gly Tyr Met Arg
 50                  55                  60

ATG GAA GGG ATG AAA GGC TGC CCC GCA GTG ATG CCT ATT GAC CAT GTT     341
Met Glu Gly Met Lys Gly Cys Pro Ala Val Met Pro Ile Asp His Val
 65              70                  75                      80

TAT GGC ACG CTG GGC ATT GTG GGA GCC ACT ACC ACT CAG CAC TAC TCC     389
Tyr Gly Thr Leu Gly Ile Val Gly Ala Thr Thr Thr Gln His Tyr Ser
                 85                  90                  95

GAT GTC TCG AAG CTG AGA GAA GAG ATT GAA GGA AAA GGG TCA TAC ACG     437
Asp Val Ser Lys Leu Arg Glu Glu Ile Glu Gly Lys Gly Ser Tyr Thr
             100                 105                 110

TAC TTC GCG CCG AGT AAC GAG GCT TGG GAG AAC CTG GAT TCT GAC ATT     485
Tyr Phe Ala Pro Ser Asn Glu Ala Trp Glu Asn Leu Asp Ser Asp Ile
         115                 120                 125

CGC AGA GGA CTG GAG AAC AAT GTC AAT GTT GAG CTA CTG AAT GCC TTA     533
Arg Arg Gly Leu Glu Asn Asn Val Asn Val Glu Leu Leu Asn Ala Leu
     130                 135                 140

CAC AGC CAC ATG GTT AAT AAG AGA ATG TTA ACC AAG GAC CTG AAA CAC     581
His Ser His Met Val Asn Lys Arg Met Leu Thr Lys Asp Leu Lys His
145                 150                 155                 160
```

| | | | | | | | | | | | | | | | | |
|---|---|---|---|---|---|---|---|---|---|---|---|---|---|---|---|---|
| GGC | ATG | GTT | ATT | CCT | TCA | ATG | TAC | AAC | AAT | CTG | GGG | CTT | TTT | ATT | AAC | 629 |
| Gly | Met | Val | Ile | Pro<br>165 | Ser | Met | Tyr | Asn | Asn<br>170 | Leu | Gly | Leu | Phe | Ile<br>175 | Asn | |
| CAT | TAT | CCC | AAT | GGG | GTT | GTC | ACT | GTG | AAC | TGT | GCT | CGA | GTC | ATC | CAT | 677 |
| His | Tyr | Pro | Asn<br>180 | Gly | Val | Val | Thr | Val<br>185 | Asn | Cys | Ala | Arg | Val<br>190 | Ile | His | |
| GGG | AAC | CAG | ATT | GCC | ACA | AAT | GGT | GTC | GTC | CAT | GTC | ATT | GAC | CGT | GTC | 725 |
| Gly | Asn | Gln<br>195 | Ile | Ala | Thr | Asn | Gly<br>200 | Val | Val | His | Val | Ile<br>205 | Asp | Arg | Val | |
| CTG | ACA | CAA | ATT | GGT | ACC | TCC | ATC | CAA | GAC | TTC | CTT | GAA | GCA | GAA | GAC | 773 |
| Leu | Thr<br>210 | Gln | Ile | Gly | Thr | Ser<br>215 | Ile | Gln | Asp | Phe | Leu<br>220 | Glu | Ala | Glu | Asp | |
| GAC | CTT | TCA | TCA | TTT | AGA | GCA | GCC | GCC | ATC | ACC | TCT | GAC | CTC | TTG | GAG | 821 |
| Asp<br>225 | Leu | Ser | Ser | Phe | Arg<br>230 | Ala | Ala | Ala | Ile | Thr<br>235 | Ser | Asp | Leu | Leu | Glu<br>240 | |
| TCC | CTT | GGA | AGA | GAT | GGT | CAC | TTC | ACG | CTC | TTT | GCT | CCC | ACC | AAT | GAA | 869 |
| Ser | Leu | Gly | Arg | Asp<br>245 | Gly | His | Phe | Thr | Leu<br>250 | Phe | Ala | Pro | Thr | Asn<br>255 | Glu | |
| GCT | TTC | GAG | AAA | CTG | CCA | CGA | GGT | GTC | CTA | GAA | AGG | ATC | ATG | GGA | GAC | 917 |
| Ala | Phe | Glu | Lys<br>260 | Leu | Pro | Arg | Gly | Val<br>265 | Leu | Glu | Arg | Ile | Met<br>270 | Gly | Asp | |
| AAA | GTG | GCT | TCT | GAA | GCT | CTC | ATG | AAG | TAC | CAC | ATC | CTA | AAT | ACC | CTC | 965 |
| Lys | Val | Ala | Ser<br>275 | Glu | Ala | Leu | Met | Lys<br>280 | Tyr | His | Ile | Leu | Asn<br>285 | Thr | Leu | |
| CAG | TGC | TCT | GAG | GCC | ATC | ACT | GGA | GGA | GCC | GTG | TTT | GAG | ACC | ATG | GAA | 1013 |
| Gln | Cys | Ser | Glu | Ala<br>290 | Ile | Thr | Gly | Gly | Ala<br>295 | Val | Phe | Glu | Thr | Met<br>300 | Glu | |
| GGA | AAC | ACT | ATT | GAG | ATA | GGG | TGC | GAA | GGG | GAC | AGT | ATC | TCC | ATT | AAC | 1061 |
| Gly | Asn | Thr | Ile | Glu<br>305 | Ile | Gly | Cys | Glu | Gly<br>310 | Asp | Ser | Ile | Ser | Ile<br>315 | Asn<br>320 | |
| GGA | ATC | AAG | ATG | GTG | AAC | AAG | AAA | GAC | ATT | GTG | ACT | AAG | AAT | GGT | GTC | 1109 |
| Gly | Ile | Lys | Met | Val<br>325 | Asn | Lys | Lys | Asp | Ile<br>330 | Val | Thr | Lys | Asn | Gly<br>335 | Val | |
| ATC | CAC | CTG | ATT | GAT | GAA | GTC | CTC | ATT | CCT | GAT | TCT | GCC | AAA | CAA | GTT | 1157 |
| Ile | His | Leu | Ile<br>340 | Asp | Glu | Val | Leu | Ile<br>345 | Pro | Asp | Ser | Ala | Lys<br>350 | Gln | Val | |
| ATT | GAG | CTG | GCT | GGA | AAA | CAG | CAA | ACC | ACT | TTC | ACC | GAC | CTG | GTA | GCC | 1205 |
| Ile | Glu | Leu | Ala<br>355 | Gly | Lys | Gln | Gln | Thr<br>360 | Thr | Phe | Thr | Asp | Leu<br>365 | Val | Ala | |
| CAA | TTA | GGC | TTG | GCA | TCC | TCT | CTG | AAG | CCA | GAT | GGA | GAG | TAC | ACC | TTA | 1253 |
| Gln | Leu | Gly<br>370 | Leu | Ala | Ser | Ser | Leu<br>375 | Lys | Pro | Asp | Gly | Glu<br>380 | Tyr | Thr | Leu | |
| TTA | GCA | CCT | GTG | AAC | AAT | GCG | TTC | TCT | GAT | GAC | ACT | CTG | AGC | ATG | GAC | 1301 |
| Leu<br>385 | Ala | Pro | Val | Asn | Asn<br>390 | Ala | Phe | Ser | Asp | Asp<br>395 | Thr | Leu | Ser | Met | Asp<br>400 | |
| CAA | CGC | CTT | CTT | AAG | CTA | ATT | CTG | CAA | AAT | CAC | ATA | TTG | AAA | GTA | AAA | 1349 |
| Gln | Arg | Leu | Leu | Lys<br>405 | Leu | Ile | Leu | Gln | Asn<br>410 | His | Ile | Leu | Lys | Val<br>415 | Lys | |
| GTT | GGC | CTT | AGC | GAC | CTC | TAC | AAT | GGA | CAG | ATA | CTG | GAA | ACC | ATT | GGA | 1397 |
| Val | Gly | Leu | Ser<br>420 | Asp | Leu | Tyr | Asn | Gly<br>425 | Gln | Ile | Leu | Glu | Thr<br>430 | Ile | Gly | |
| GGC | AAA | CAA | CTC | CGA | GTC | TTT | GTG | TAT | CGG | ACG | GCT | ATC | TGC | ATA | GAA | 1445 |
| Gly | Lys | Gln | Leu<br>435 | Arg | Val | Phe | Val | Tyr<br>440 | Arg | Thr | Ala | Ile | Cys<br>445 | Ile | Glu | |
| AAC | TCA | TGC | ATG | GTG | AGA | GGA | AGC | AAG | CAG | GGA | AGG | AAT | GGT | GCC | ATT | 1493 |
| Asn | Ser | Cys<br>450 | Met | Val | Arg | Gly | Ser<br>455 | Lys | Gln | Gly | Arg | Asn<br>460 | Gly | Ala | Ile | |
| CAC | ATA | TTC | CGA | GAA | ATC | ATC | CAA | CCA | GCA | GAG | AAA | TCC | CTG | CAC | GAC | 1541 |
| His | Ile | Phe | Arg<br>465 | Glu | Ile | Ile | Gln<br>470 | Pro | Ala | Glu | Lys | Ser<br>475 | Leu | His | Asp<br>480 | |

| | |
|---|---|
| AAG CTG CGG CAA GAC AAG CGC TTT AGC ATC TTC CTC AGC CTC CTT GAA<br>Lys Leu Arg Gln Asp Lys Arg Phe Ser Ile Phe Leu Ser Leu Leu Glu<br>485                                490                         495 | 1589 |
| GCT GCA GAT TTG AAA GAT CTC CTG ACA CAG CCC GGA GAT TGG ACC TTG<br>Ala Ala Asp Leu Lys Asp Leu Leu Thr Gln Pro Gly Asp Trp Thr Leu<br>500                              505                         510 | 1637 |
| TTT GCA CCA ACC AAT GAT GCC TTC AAG GGA ATG ACT AGC GAA GAA AGG<br>Phe Ala Pro Thr Asn Asp Ala Phe Lys Gly Met Thr Ser Glu Glu Arg<br>515                              520                       525 | 1685 |
| GAG CTT CTG ATT GGG GAT AAA AAT GCT CTC CAA AAC ATC ATT CTT TAT<br>Glu Leu Leu Ile Gly Asp Lys Asn Ala Leu Gln Asn Ile Ile Leu Tyr<br>530                              535                       540 | 1733 |
| CAC CTG ACC CCA GGG GTT TAT ATT GGA AAG GGA TTC GAA CCC GGA GTC<br>His Leu Thr Pro Gly Val Tyr Ile Gly Lys Gly Phe Glu Pro Gly Val<br>545                          550                       555                   560 | 1781 |
| ACT AAT ATC CTG AAG ACC ACA CAG GGA AGC AAA ATC TAT CTG AAA GGA<br>Thr Asn Ile Leu Lys Thr Thr Gln Gly Ser Lys Ile Tyr Leu Lys Gly<br>                        565                             570                       575 | 1829 |
| GTA AAC GAA ACG CTT CTA GTG AAT GAG TTG AAG TCC AAA GAA TCT GAC<br>Val Asn Glu Thr Leu Leu Val Asn Glu Leu Lys Ser Lys Glu Ser Asp<br>                   580                          585                       590 | 1877 |
| ATC ATG ACG ACA AAT GGT GTC ATC CAC GTC GTG GAC AAA CTC CTC TAT<br>Ile Met Thr Thr Asn Gly Val Ile His Val Val Asp Lys Leu Leu Tyr<br>         595                              600                   605 | 1925 |
| CCA GCA GAT ATT CCA GTT GGA AAT GAT CAG CTC TTG GAA TTA CTG AAC<br>Pro Ala Asp Ile Pro Val Gly Asn Asp Gln Leu Leu Glu Leu Leu Asn<br>610                              615                       620 | 1973 |
| AAA CTG ATA AAA TAC ATC CAA ATC AAG TTT GTT CGT GGC AGC ACC TTC<br>Lys Leu Ile Lys Tyr Ile Gln Ile Lys Phe Val Arg Gly Ser Thr Phe<br>625                              630                       635                   640 | 2021 |
| AAA GAA ATC CCC ATG ACT GTC TAT AGA CCT GCA ATG ACG AAG ATC CAA<br>Lys Glu Ile Pro Met Thr Val Tyr Arg Pro Ala Met Thr Lys Ile Gln<br>                   645                          650                       655 | 2069 |
| ATT GAA GGT GAT CCC GAC TTC AGG CTG ATT AAA GAA GGC GAA ACG GTG<br>Ile Glu Gly Asp Pro Asp Phe Arg Leu Ile Lys Glu Gly Glu Thr Val<br>                   660                        665                       670 | 2117 |
| ACA GAA GTG ATC CAC GGA GAG CCA GTC ATT AAA AAG TAC ACC AAA ATC<br>Thr Glu Val Ile His Gly Glu Pro Val Ile Lys Lys Tyr Thr Lys Ile<br>675                              680                       685 | 2165 |
| ATA GAT GGA GTT CCT GTT GAA ATA ACT GAA AAA CAG ACT CGG GAA GAA<br>Ile Asp Gly Val Pro Val Glu Ile Thr Glu Lys Gln Thr Arg Glu Glu<br>690                              695                       700 | 2213 |
| CGA ATC ATT ACA GGT CCT GAG ATA AAA TAT ACC AGG ATT TCC ACA GGA<br>Arg Ile Ile Thr Gly Pro Glu Ile Lys Tyr Thr Arg Ile Ser Thr Gly<br>705                              710                       715                   720 | 2261 |
| GGT GGA GAA ACA GGA GAG ACC TTG CAG AAA TTC TTG CAA AAA GAG GTC<br>Gly Gly Glu Thr Gly Glu Thr Leu Gln Lys Phe Leu Gln Lys Glu Val<br>                        725                             730                       735 | 2309 |
| TCC AAG GTC ACA AAG TTC ATT GAA GGT GGC GAT GGT CAC TTA TTT GAA<br>Ser Lys Val Thr Lys Phe Ile Glu Gly Gly Asp Gly His Leu Phe Glu<br>                   740                          745                   750 | 2357 |
| GAT GAG GAG ATT AAA AGA CTG CTT CAG GGA GAC ACA CCT GCA AAG AAG<br>Asp Glu Glu Ile Lys Arg Leu Leu Gln Gly Asp Thr Pro Ala Lys Lys<br>         755                              760                   765 | 2405 |
| ATA CCA GCC AAC AAA AGG GTT CAA GGG CCT AGA AGA CGA TCA AGA GAA<br>Ile Pro Ala Asn Lys Arg Val Gln Gly Pro Arg Arg Arg Ser Arg Glu<br>770                              775                       780 | 2453 |
| GGC CGT TCT CAGTGAAAAC CCAGAGGCCA GACCACAGAG TTTATATAAT<br>Gly Arg Ser Gln<br>785 | 2502 |

| | | | | | | |
|---|---|---|---|---|---|---|
| CCTAAATCAA | CGATCTGATT | TTAAGGGAAA | TTGTAAGAGC | CACCACACTG | ACTTCAGAAT | 2562 |
| CTGAAATGAC | AACCAACAGA | AGCCAATCTT | CAAGCAAGTC | CAAACACAGA | GTTCATGTCT | 2622 |
| TTGTTTCTGC | ATGAGAAATA | TAAGAAAATG | ATAGCTAGTC | TCCTGTGGGG | TAGGAACTGA | 2682 |
| GGAAATATAG | GACCATGCAG | GGATTTTATC | TCAATGAGAA | AACTTCTGAT | TAAAGTAGAA | 2742 |
| TCCACCAAAG | AACATCATTG | TGACTGGGTC | CATACAGCTA | AGTCTTTGCA | CAGTAAAAAC | 2802 |
| CTTCCGCCTC | AGGAAGAGGC | TGGAAAAACC | CAAAGCACAC | AGTTACCTTT | CCAGGGGAGG | 2862 |
| CTAAGGTATC | AAAAGGGGTG | TTCAGTTATA | CAACATGCAA | ACAAACCTAC | CAAATTACGA | 2922 |
| ACAGTGGTGT | TACATATTTC | TCATGCAATG | TGGGTTTCCT | GCTAAATTTT | GTTATTTTTA | 2982 |
| CACTTGATTT | ATATCCTCGA | GATGATTGTC | ATAAGCTTCT | TGCAATACAA | ATGTTTCTC | 3042 |
| TCAAACATTT | CAATAAAACC | ATTCTTCAGG | TATAAAGAGA | ATTACTGCAG | AGTTGGTAAT | 3102 |
| TCAGAAAACT | CAAGGTTTAA | GTTAAAAGTG | AGTTTAGACT | TTGGAATAGG | ACTTCATACC | 3162 |
| TTTTTTTATT | GTTAACAAGT | ACTCAATAAA | GTAAACTGAG | CGGCCGCGAA | TTC | 3215 |

( 2 ) INFORMATION FOR SEQ ID NO:2:

( i ) SEQUENCE CHARACTERISTICS:
        ( A ) LENGTH: 811 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Pro Leu Leu Pro Leu Tyr Ala Leu Leu Leu Phe Leu Cys
-23         -20             -15             -10

Asp Ile Asn Pro Ala Asn Ala Asn Ser Tyr Tyr Asp Lys Val Leu Ala
         -5               1               5

His Ser Arg Ile Arg Gly Arg Asp Gln Gly Pro Asn Val Cys Ala Leu
 10              15              20                      25

Gln Gln Ile Leu Gly Thr Lys Lys Tyr Phe Ser Ser Cys Lys Asn
                 30              35                  40

Trp Tyr Gln Gly Ala Ile Cys Gly Lys Lys Thr Thr Val Leu Tyr Glu
             45              50              55

Cys Cys Pro Gly Tyr Met Arg Met Glu Gly Met Lys Gly Cys Pro Ala
         60              65              70

Val Met Pro Ile Asp His Val Tyr Gly Thr Leu Gly Ile Val Gly Ala
     75              80              85

Thr Thr Thr Gln His Tyr Ser Asp Val Ser Lys Leu Arg Glu Glu Ile
 90              95              100                     105

Glu Gly Lys Gly Ser Tyr Thr Tyr Phe Ala Pro Ser Asn Glu Ala Trp
             110             115                 120

Glu Asn Leu Asp Ser Asp Ile Arg Arg Gly Leu Glu Asn Asn Val Asn
             125             130             135

Val Glu Leu Leu Asn Ala Leu His Ser His Met Val Asn Lys Arg Met
         140             145             150

Leu Thr Lys Asp Leu Lys His Gly Met Val Ile Pro Ser Met Tyr Asn
     155             160             165

Asn Leu Gly Leu Phe Ile Asn His Tyr Pro Asn Gly Val Val Thr Val
170             175             180             185

Asn Cys Ala Arg Val Ile His Gly Asn Gln Ile Ala Thr Asn Gly Val
             190             195             200

Val His Val Ile Asp Arg Val Leu Thr Gln Ile Gly Thr Ser Ile Gln
         205             210             215
```

| | | | | | | | | | | | | | |
|---|---|---|---|---|---|---|---|---|---|---|---|---|---|
|Asp|Phe|Leu|Glu|Ala|Glu|Asp|Leu|Ser|Ser|Phe|Arg|Ala|Ala|Ala|
| | |220| | | |225| | | |230| | | |
|Ile|Thr|Ser|Asp|Leu|Leu|Glu|Ser|Leu|Gly|Arg|Asp|Gly|His|Phe|Thr|
| |235| | | |240| | | |245| | | | | |
|Leu|Phe|Ala|Pro|Thr|Asn|Glu|Ala|Phe|Glu|Lys|Leu|Pro|Arg|Gly|Val|
|250| | | | |255| | | |260| | | | |265|
|Leu|Glu|Arg|Ile|Met|Gly|Asp|Lys|Val|Ala|Ser|Glu|Ala|Leu|Met|Lys|
| | | | |270| | | |275| | | | |280| |
|Tyr|His|Ile|Leu|Asn|Thr|Leu|Gln|Cys|Ser|Glu|Ala|Ile|Thr|Gly|Gly|
| | | |285| | | |290| | | | |295| | |
|Ala|Val|Phe|Glu|Thr|Met|Glu|Gly|Asn|Thr|Ile|Glu|Ile|Gly|Cys|Glu|
| | |300| | | |305| | | | |310| | | |
|Gly|Asp|Ser|Ile|Ser|Ile|Asn|Gly|Ile|Lys|Met|Val|Asn|Lys|Lys|Asp|
| |315| | | | |320| | | |325| | | | |
|Ile|Val|Thr|Lys|Asn|Gly|Val|Ile|His|Leu|Ile|Asp|Glu|Val|Leu|Ile|
|330| | | | |335| | | |340| | | | |345|
|Pro|Asp|Ser|Ala|Lys|Gln|Val|Ile|Glu|Leu|Ala|Gly|Lys|Gln|Gln|Thr|
| | | | |350| | | |355| | | | |360| |
|Thr|Phe|Thr|Asp|Leu|Val|Ala|Gln|Leu|Gly|Leu|Ala|Ser|Ser|Leu|Lys|
| | | |365| | | |370| | | | |375| | |
|Pro|Asp|Gly|Glu|Tyr|Thr|Leu|Leu|Ala|Pro|Val|Asn|Asn|Ala|Phe|Ser|
| | |380| | | | |385| | | | |390| | |
|Asp|Asp|Thr|Leu|Ser|Met|Asp|Gln|Arg|Leu|Leu|Lys|Leu|Ile|Leu|Gln|
| |395| | | | |400| | | | |405| | | |
|Asn|His|Ile|Leu|Lys|Val|Lys|Val|Gly|Leu|Ser|Asp|Leu|Tyr|Asn|Gly|
|410| | | | |415| | | |420| | | | |425|
|Gln|Ile|Leu|Glu|Thr|Ile|Gly|Gly|Lys|Gln|Leu|Arg|Val|Phe|Val|Tyr|
| | | | |430| | | |435| | | | |440| |
|Arg|Thr|Ala|Ile|Cys|Ile|Glu|Asn|Ser|Cys|Met|Val|Arg|Gly|Ser|Lys|
| | | |445| | | |450| | | | |455| | |
|Gln|Gly|Arg|Asn|Gly|Ala|Ile|His|Ile|Phe|Arg|Glu|Ile|Ile|Gln|Pro|
| | |460| | | | |465| | | | |470| | |
|Ala|Glu|Lys|Ser|Leu|His|Asp|Lys|Leu|Arg|Gln|Asp|Lys|Arg|Phe|Ser|
| |475| | | | |480| | | | |485| | | |
|Ile|Phe|Leu|Ser|Leu|Leu|Glu|Ala|Ala|Asp|Leu|Lys|Asp|Leu|Leu|Thr|
|490| | | | |495| | | |500| | | | |505|
|Gln|Pro|Gly|Asp|Trp|Thr|Leu|Phe|Ala|Pro|Thr|Asn|Asp|Ala|Phe|Lys|
| | | |510| | | |515| | | | |520| | |
|Gly|Met|Thr|Ser|Glu|Glu|Arg|Glu|Leu|Leu|Ile|Gly|Asp|Lys|Asn|Ala|
| | |525| | | |530| | | | |535| | | |
|Leu|Gln|Asn|Ile|Ile|Leu|Tyr|His|Leu|Thr|Pro|Gly|Val|Tyr|Ile|Gly|
| | |540| | | |545| | | | |550| | | |
|Lys|Gly|Phe|Glu|Pro|Gly|Val|Thr|Asn|Ile|Leu|Lys|Thr|Thr|Gln|Gly|
| |555| | | |560| | | |565| | | | | |
|Ser|Lys|Ile|Tyr|Leu|Lys|Gly|Val|Asn|Glu|Thr|Leu|Leu|Val|Asn|Glu|
|570| | | |575| | | |580| | | | |585| |
|Leu|Lys|Ser|Lys|Glu|Ser|Asp|Ile|Met|Thr|Thr|Asn|Gly|Val|Ile|His|
| | | |590| | | |595| | | | |600| | |
|Val|Val|Asp|Lys|Leu|Leu|Tyr|Pro|Ala|Asp|Ile|Pro|Val|Gly|Asn|Asp|
| | |605| | | |610| | | |615| | | | |
|Gln|Leu|Leu|Glu|Leu|Leu|Asn|Lys|Leu|Ile|Lys|Tyr|Ile|Gln|Ile|Lys|
| |620| | | | |625| | | |630| | | | |
|Phe|Val|Arg|Gly|Ser|Thr|Phe|Lys|Glu|Ile|Pro|Met|Thr|Val|Tyr|Arg|

|       |       |       |       | 635   |       |       |       |       | 640   |       |       |       |       | 645   |       |
|-------|-------|-------|-------|-------|-------|-------|-------|-------|-------|-------|-------|-------|-------|-------|-------|
| Pro   | Ala   | Met   | Thr   | Lys   | Ile   | Gln   | Ile   | Glu   | Gly   | Asp   | Pro   | Asp   | Phe   | Arg   | Leu   |
| 650   |       |       |       |       | 655   |       |       |       |       | 660   |       |       |       |       | 665   |
| Ile   | Lys   | Glu   | Gly   | Glu   | Thr   | Val   | Thr   | Glu   | Val   | Ile   | His   | Gly   | Glu   | Pro   | Val   |
|       |       |       |       | 670   |       |       |       |       | 675   |       |       |       |       | 680   |       |
| Ile   | Lys   | Lys   | Tyr   | Thr   | Lys   | Ile   | Ile   | Asp   | Gly   | Val   | Pro   | Val   | Glu   | Ile   | Thr   |
|       |       |       | 685   |       |       |       |       | 690   |       |       |       |       | 695   |       |       |
| Glu   | Lys   | Gln   | Thr   | Arg   | Glu   | Glu   | Arg   | Ile   | Ile   | Thr   | Gly   | Pro   | Glu   | Ile   | Lys   |
|       |       | 700   |       |       |       |       | 705   |       |       |       |       | 710   |       |       |       |
| Tyr   | Thr   | Arg   | Ile   | Ser   | Thr   | Gly   | Gly   | Gly   | Glu   | Thr   | Gly   | Glu   | Thr   | Leu   | Gln   |
|       | 715   |       |       |       |       | 720   |       |       |       |       | 725   |       |       |       |       |
| Lys   | Phe   | Leu   | Gln   | Lys   | Glu   | Val   | Ser   | Lys   | Val   | Thr   | Lys   | Phe   | Ile   | Glu   | Gly   |
| 730   |       |       |       |       | 735   |       |       |       |       | 740   |       |       |       |       | 745   |
| Gly   | Asp   | Gly   | His   | Leu   | Phe   | Glu   | Asp   | Glu   | Glu   | Ile   | Lys   | Arg   | Leu   | Leu   | Gln   |
|       |       |       |       | 750   |       |       |       |       | 755   |       |       |       |       | 760   |       |
| Gly   | Asp   | Thr   | Pro   | Ala   | Lys   | Lys   | Ile   | Pro   | Ala   | Asn   | Lys   | Arg   | Val   | Gln   | Gly   |
|       |       |       | 765   |       |       |       |       | 770   |       |       |       |       | 775   |       |       |
| Pro   | Arg   | Arg   | Arg   | Ser   | Arg   | Glu   | Gly   | Arg   | Ser   | Gln   |       |       |       |       |       |
|       |       | 780   |       |       |       |       | 785   |       |       |       |       |       |       |       |       |

( 2 ) INFORMATION FOR SEQ ID NO:3:

( i ) SEQUENCE CHARACTERISTICS:
        ( A ) LENGTH: 3092 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens
        ( F ) TISSUE TYPE: Placenta ( i x ) FEATURE:
        ( A ) NAME/KEY: CDS
        ( B ) LOCATION: join(38..2375)

( i x ) FEATURE:
        ( A ) NAME/KEY: mat_peptide
        ( B ) LOCATION: join(101..2375)

( x i ) SEQUENCE DESCRIPTION: SEQ ID NO:3:

| GAATTCGGGG | AACAGAACTG | CAACGGAGAG | ACTCAAG | ATG | ATT | CCC | TTT | TTA | CCC | 55 |
|---|---|---|---|---|---|---|---|---|---|---|
|   |   |   |   | Met | Ile | Pro | Phe | Leu | Pro |   |
|   |   |   |   | -21 | -20 |   |   |   |   |   |

| ATG | TTT | TCT | CTA | CTA | TTG | CTG | CTT | ATT | GTT | AAC | CCT | ATA | AAC | GCC | AAC | 103 |
|---|---|---|---|---|---|---|---|---|---|---|---|---|---|---|---|---|
| Met | Phe | Ser | Leu | Leu | Leu | Leu | Leu | Ile | Val | Asn | Pro | Ile | Asn | Ala | Asn |   |
| -15 |   |   |   | -10 |   |   |   |   | -5 |   |   |   |   |   | 1 |   |

| AAT | CAT | TAT | GAC | AAG | ATC | TTG | GCT | CAT | AGT | CGT | ATC | AGG | GGT | CGG | GAC | 151 |
|---|---|---|---|---|---|---|---|---|---|---|---|---|---|---|---|---|
| Asn | His | Tyr | Asp | Lys | Ile | Leu | Ala | His | Ser | Arg | Ile | Arg | Gly | Arg | Asp |   |
|   |   |   | 5 |   |   |   |   | 10 |   |   |   |   | 15 |   |   |   |

| CAA | GGC | CCA | AAT | GTC | TGT | GCC | CTT | CAA | CAG | ATT | TTG | GGC | ACC | AAA | AAG | 199 |
|---|---|---|---|---|---|---|---|---|---|---|---|---|---|---|---|---|
| Gln | Gly | Pro | Asn | Val | Cys | Ala | Leu | Gln | Gln | Ile | Leu | Gly | Thr | Lys | Lys |   |
|   |   | 20 |   |   |   |   | 25 |   |   |   |   | 30 |   |   |   |   |

| AAA | TAC | TTC | AGC | ACT | TGT | AAG | AAC | TGG | TAT | AAA | AAG | TCC | ATC | TGT | GGA | 247 |
|---|---|---|---|---|---|---|---|---|---|---|---|---|---|---|---|---|
| Lys | Tyr | Phe | Ser | Thr | Cys | Lys | Asn | Trp | Tyr | Lys | Lys | Ser | Ile | Cys | Gly |   |
|   | 35 |   |   |   |   | 40 |   |   |   |   | 45 |   |   |   |   |   |

| CAG | AAA | ACG | ACT | GTT | TTA | TAT | GAA | TGT | TGC | CCT | GGT | TAT | ATG | AGA | ATG | 295 |
|---|---|---|---|---|---|---|---|---|---|---|---|---|---|---|---|---|
| Gln | Lys | Thr | Thr | Val | Leu | Tyr | Glu | Cys | Cys | Pro | Gly | Tyr | Met | Arg | Met |   |
| 50 |   |   |   |   | 55 |   |   |   |   | 60 |   |   |   |   | 65 |   |

| GAA | GGA | ATG | AAA | GGC | TGC | CCA | GCA | GTT | TTG | CCC | ATT | GAC | CAT | GTT | TAT | 343 |
|---|---|---|---|---|---|---|---|---|---|---|---|---|---|---|---|---|
| Glu | Gly | Met | Lys | Gly | Cys | Pro | Ala | Val | Leu | Pro | Ile | Asp | His | Val | Tyr |   |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 70  |     |     |     |     | 75  |     |     |     |     |     | 80  |     |      |
| GGC | ACT | CTG | GGC | ATC | GTG | GGA | GCC | ACC | ACA | ACG | CAG | CGC | TAT | TCT | GAC | 391  |
| Gly | Thr | Leu | Gly | Ile | Val | Gly | Ala | Thr | Thr | Thr | Gln | Arg | Tyr | Ser | Asp |      |
|     |     |     | 85  |     |     |     |     | 90  |     |     |     |     |     | 95  |     |      |
| GCC | TCA | AAA | CTG | AGG | GAG | GAG | ATC | GAG | GGA | AAG | GGA | TCC | TTC | ACT | TAC | 439  |
| Ala | Ser | Lys | Leu | Arg | Glu | Glu | Ile | Glu | Gly | Lys | Gly | Ser | Phe | Thr | Tyr |      |
|     |     |     | 100 |     |     |     |     | 105 |     |     |     |     |     | 110 |     |      |
| TTT | GCA | CCG | AGT | AAT | GAG | GCT | TGG | GAC | AAC | TTG | GAT | TCT | GAT | ATC | CGT | 487  |
| Phe | Ala | Pro | Ser | Asn | Glu | Ala | Trp | Asp | Asn | Leu | Asp | Ser | Asp | Ile | Arg |      |
|     |     |     | 115 |     |     |     |     | 120 |     |     |     |     |     | 125 |     |      |
| AGA | GGT | TTG | GAG | AGC | AAC | GTG | AAT | GTT | GAA | TTA | CTG | AAT | GCT | TTA | CAT | 535  |
| Arg | Gly | Leu | Glu | Ser | Asn | Val | Asn | Val | Glu | Leu | Leu | Asn | Ala | Leu | His |      |
|     | 130 |     |     |     |     | 135 |     |     |     |     | 140 |     |     |     | 145 |      |
| AGT | CAC | ATG | ATT | AAT | AAG | AGA | ATG | TTG | ACC | AAG | GAC | TTA | AAA | AAT | GGC | 583  |
| Ser | His | Met | Ile | Asn | Lys | Arg | Met | Leu | Thr | Lys | Asp | Leu | Lys | Asn | Gly |      |
|     |     |     |     | 150 |     |     |     |     | 155 |     |     |     |     | 160 |     |      |
| ATG | ATT | ATT | CCT | TCA | ATG | TAT | AAC | AAT | TTG | GGG | CTT | TTC | ATT | AAC | CAT | 631  |
| Met | Ile | Ile | Pro | Ser | Met | Tyr | Asn | Asn | Leu | Gly | Leu | Phe | Ile | Asn | His |      |
|     |     |     | 165 |     |     |     |     | 170 |     |     |     |     |     | 175 |     |      |
| TAT | CCT | AAT | GGG | GTT | GTC | ACT | GTT | AAT | TGT | GCT | CGA | ATC | ATC | CAT | GGG | 679  |
| Tyr | Pro | Asn | Gly | Val | Val | Thr | Val | Asn | Cys | Ala | Arg | Ile | Ile | His | Gly |      |
|     |     |     | 180 |     |     |     |     | 185 |     |     |     |     |     | 190 |     |      |
| AAC | CAG | ATT | GCA | ACA | AAT | GGT | GTT | GTC | CAT | GTC | ATT | GAC | CGT | GTG | CTT | 727  |
| Asn | Gln | Ile | Ala | Thr | Asn | Gly | Val | Val | His | Val | Ile | Asp | Arg | Val | Leu |      |
|     | 195 |     |     |     |     | 200 |     |     |     |     | 205 |     |     |     |     |      |
| ACA | CAA | ATT | GGT | ACC | TCA | ATT | CAA | GAC | TTC | ATT | GAA | GCA | GAA | GAT | GAC | 775  |
| Thr | Gln | Ile | Gly | Thr | Ser | Ile | Gln | Asp | Phe | Ile | Glu | Ala | Glu | Asp | Asp |      |
| 210 |     |     |     |     | 215 |     |     |     |     | 220 |     |     |     |     | 225 |      |
| CTT | TCA | TCT | TTT | AGA | GCA | GCT | GCC | ATC | ACA | TCG | GAC | ATA | TTG | GAG | GCC | 823  |
| Leu | Ser | Ser | Phe | Arg | Ala | Ala | Ala | Ile | Thr | Ser | Asp | Ile | Leu | Glu | Ala |      |
|     |     |     |     | 230 |     |     |     |     | 235 |     |     |     |     | 240 |     |      |
| CTT | GGA | AGA | GAC | GGT | CAC | TTC | ACA | CTC | TTT | GCT | CCC | ACC | AAT | GAG | GCT | 871  |
| Leu | Gly | Arg | Asp | Gly | His | Phe | Thr | Leu | Phe | Ala | Pro | Thr | Asn | Glu | Ala |      |
|     |     |     | 245 |     |     |     |     | 250 |     |     |     |     |     | 255 |     |      |
| TTT | GAG | AAA | CTT | CCA | CGA | GGT | GTC | CTA | GAA | AGG | TTC | ATG | GGA | GAC | AAA | 919  |
| Phe | Glu | Lys | Leu | Pro | Arg | Gly | Val | Leu | Glu | Arg | Phe | Met | Gly | Asp | Lys |      |
|     |     | 260 |     |     |     |     | 265 |     |     |     |     | 270 |     |     |     |      |
| GTG | GCT | TCC | GAA | GCT | CTT | ATG | AAG | TAC | CAC | ATC | TTA | AAT | ACT | CTC | CAG | 967  |
| Val | Ala | Ser | Glu | Ala | Leu | Met | Lys | Tyr | His | Ile | Leu | Asn | Thr | Leu | Gln |      |
|     | 275 |     |     |     |     | 280 |     |     |     |     | 285 |     |     |     |     |      |
| TGT | TCT | GAG | TCT | ATT | ATG | GGA | GGA | GCA | GTC | TTT | GAG | ACG | CTG | GAA | GGA | 1015 |
| Cys | Ser | Glu | Ser | Ile | Met | Gly | Gly | Ala | Val | Phe | Glu | Thr | Leu | Glu | Gly |      |
| 290 |     |     |     |     | 295 |     |     |     |     | 300 |     |     |     |     | 305 |      |
| AAT | ACA | ATT | GAG | ATA | GGA | TGT | GAC | GGT | GAC | AGT | ATA | ACA | GTA | AAT | GGA | 1063 |
| Asn | Thr | Ile | Glu | Ile | Gly | Cys | Asp | Gly | Asp | Ser | Ile | Thr | Val | Asn | Gly |      |
|     |     |     |     | 310 |     |     |     |     | 315 |     |     |     |     | 320 |     |      |
| ATC | AAA | ATG | GTG | AAC | AAA | AAG | GAT | ATT | GTG | ACA | AAT | AAT | GGT | GTG | ATC | 1111 |
| Ile | Lys | Met | Val | Asn | Lys | Lys | Asp | Ile | Val | Thr | Asn | Asn | Gly | Val | Ile |      |
|     |     |     | 325 |     |     |     |     | 330 |     |     |     |     |     | 335 |     |      |
| CAT | TTG | ATT | GAT | CAG | GTC | CTA | ATT | CCT | GAT | TCT | GCC | AAA | CAA | GTT | ATT | 1159 |
| His | Leu | Ile | Asp | Gln | Val | Leu | Ile | Pro | Asp | Ser | Ala | Lys | Gln | Val | Ile |      |
|     |     | 340 |     |     |     |     | 345 |     |     |     |     | 350 |     |     |     |      |
| GAG | CTG | GCT | GGA | AAA | CAG | CAA | ACC | ACC | TTC | ACG | GAT | CTT | GTG | GCC | CAA | 1207 |
| Glu | Leu | Ala | Gly | Lys | Gln | Gln | Thr | Thr | Phe | Thr | Asp | Leu | Val | Ala | Gln |      |
|     | 355 |     |     |     |     | 360 |     |     |     |     | 365 |     |     |     |     |      |
| TTA | GGC | TTG | GCA | TCT | GCT | CTG | AGG | CCA | GAT | GGA | GAA | TAC | ACT | TTG | CTG | 1255 |
| Leu | Gly | Leu | Ala | Ser | Ala | Leu | Arg | Pro | Asp | Gly | Glu | Tyr | Thr | Leu | Leu |      |
| 370 |     |     |     |     | 375 |     |     |     |     | 380 |     |     |     |     | 385 |      |
| GCA | CCT | GTG | AAT | AAT | GCA | TTT | TCT | GAT | GAT | ACT | CTC | AGC | ATG | GTT | CAG | 1303 |
| Ala | Pro | Val | Asn | Asn | Ala | Phe | Ser | Asp | Asp | Thr | Leu | Ser | Met | Val | Gln |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 390 |     |     |     |     | 395 |     |     |     |     | 400 |     |      |
| CGC | CTC | CTT | AAA | TTA | ATT | CTG | CAG | AAT | CAC | ATA | TTG | AAA | GTA | AAA | GTT | 1351 |
| Arg | Leu | Leu | Lys | Leu | Ile | Leu | Gln | Asn | His | Ile | Leu | Lys | Val | Lys | Val |      |
|     |     |     | 405 |     |     |     |     | 410 |     |     |     |     | 415 |     |     |      |
| GGC | CTT | AAT | GAG | CTT | TAC | AAC | GGG | CAA | ATA | CTG | GAA | ACC | ATC | GGA | GGC | 1399 |
| Gly | Leu | Asn | Glu | Leu | Tyr | Asn | Gly | Gln | Ile | Leu | Glu | Thr | Ile | Gly | Gly |      |
|     |     | 420 |     |     |     |     | 425 |     |     |     |     | 430 |     |     |     |      |
| AAA | CAG | CTC | AGA | GTC | TTC | GTA | TAT | CGT | ACA | GCT | GTC | TGC | ATT | GAA | AAT | 1447 |
| Lys | Gln | Leu | Arg | Val | Phe | Val | Tyr | Arg | Thr | Ala | Val | Cys | Ile | Glu | Asn |      |
|     | 435 |     |     |     |     | 440 |     |     |     |     | 445 |     |     |     |     |      |
| TCA | TGC | ATG | GAG | AAA | GGG | AGT | AAG | CAA | GGG | AGA | AAC | GGT | GCG | ATT | CAC | 1495 |
| Ser | Cys | Met | Glu | Lys | Gly | Ser | Lys | Gln | Gly | Arg | Asn | Gly | Ala | Ile | His |      |
| 450 |     |     |     |     | 455 |     |     |     |     | 460 |     |     |     |     | 465 |      |
| ATA | TTC | CGC | GAG | ATC | ATC | AAG | CCA | GCA | GAG | AAA | TCC | CTC | CAT | GAA | AAG | 1543 |
| Ile | Phe | Arg | Glu | Ile | Ile | Lys | Pro | Ala | Glu | Lys | Ser | Leu | His | Glu | Lys |      |
|     |     |     |     | 470 |     |     |     |     | 475 |     |     |     |     | 480 |     |      |
| TTA | AAA | CAA | GAT | AAG | CGC | TTT | AGC | ACC | TTC | CTC | AGC | CTA | CTT | GAA | GCT | 1591 |
| Leu | Lys | Gln | Asp | Lys | Arg | Phe | Ser | Thr | Phe | Leu | Ser | Leu | Leu | Glu | Ala |      |
|     |     |     | 485 |     |     |     |     | 490 |     |     |     |     | 495 |     |     |      |
| GCA | GAC | TTG | AAA | GAG | CTC | CTG | ACA | CAA | CCT | GGA | GAC | TGG | ACA | TTA | TTT | 1639 |
| Ala | Asp | Leu | Lys | Glu | Leu | Leu | Thr | Gln | Pro | Gly | Asp | Trp | Thr | Leu | Phe |      |
|     |     | 500 |     |     |     |     | 505 |     |     |     |     | 510 |     |     |     |      |
| GTG | CCA | ACC | AAT | GAT | GCT | TTT | AAG | GGA | ATG | ACT | AGT | GAA | GAA | AAA | GAA | 1687 |
| Val | Pro | Thr | Asn | Asp | Ala | Phe | Lys | Gly | Met | Thr | Ser | Glu | Glu | Lys | Glu |      |
|     | 515 |     |     |     |     | 520 |     |     |     |     | 525 |     |     |     |     |      |
| ATT | CTG | ATA | CGG | GAC | AAA | AAT | GCT | CTT | CAA | AAC | ATC | ATT | CTT | TAT | CAC | 1735 |
| Ile | Leu | Ile | Arg | Asp | Lys | Asn | Ala | Leu | Gln | Asn | Ile | Ile | Leu | Tyr | His |      |
| 530 |     |     |     |     | 535 |     |     |     |     | 540 |     |     |     |     | 545 |      |
| CTG | ACA | CCA | GGA | GTT | TTC | ATT | GGA | AAA | GGA | TTT | GAA | CCT | GGT | GTT | ACT | 1783 |
| Leu | Thr | Pro | Gly | Val | Phe | Ile | Gly | Lys | Gly | Phe | Glu | Pro | Gly | Val | Thr |      |
|     |     |     |     | 550 |     |     |     |     | 555 |     |     |     |     | 560 |     |      |
| AAC | ATT | TTA | AAG | ACC | ACA | CAA | GGA | AGC | AAA | ATC | TTT | CTG | AAA | GAA | GTA | 1831 |
| Asn | Ile | Leu | Lys | Thr | Thr | Gln | Gly | Ser | Lys | Ile | Phe | Leu | Lys | Glu | Val |      |
|     |     |     | 565 |     |     |     |     | 570 |     |     |     |     | 575 |     |     |      |
| AAT | GAT | ACA | CTT | CTG | GTG | AAT | GAA | TTG | AAA | TCA | AAA | GAA | TCT | GAC | ATC | 1879 |
| Asn | Asp | Thr | Leu | Leu | Val | Asn | Glu | Leu | Lys | Ser | Lys | Glu | Ser | Asp | Ile |      |
|     |     | 580 |     |     |     |     | 585 |     |     |     |     | 590 |     |     |     |      |
| ATG | ACA | ACA | AAT | GGT | GTA | ATT | CAT | GTT | GTA | GAT | AAA | CTC | CTC | TAT | CCA | 1927 |
| Met | Thr | Thr | Asn | Gly | Val | Ile | His | Val | Val | Asp | Lys | Leu | Leu | Tyr | Pro |      |
|     | 595 |     |     |     |     | 600 |     |     |     |     | 605 |     |     |     |     |      |
| GCA | GAC | ACA | CCT | GTT | GGA | AAT | GAT | CAA | CTG | CTG | GAA | ATA | CTT | AAT | AAA | 1975 |
| Ala | Asp | Thr | Pro | Val | Gly | Asn | Asp | Gln | Leu | Leu | Glu | Ile | Leu | Asn | Lys |      |
| 610 |     |     |     |     | 615 |     |     |     |     | 620 |     |     |     |     | 625 |      |
| TTA | ATC | AAA | TAC | ATC | CAA | ATT | AAG | TTT | GTT | CGT | GGT | AGC | ACC | TTC | AAA | 2023 |
| Leu | Ile | Lys | Tyr | Ile | Gln | Ile | Lys | Phe | Val | Arg | Gly | Ser | Thr | Phe | Lys |      |
|     |     |     |     | 630 |     |     |     |     | 635 |     |     |     |     | 640 |     |      |
| GAA | ATC | CCC | GTG | ACT | GTC | TAT | AAG | CCA | ATT | ATT | AAA | AAA | TAC | ACC | AAA | 2071 |
| Glu | Ile | Pro | Val | Thr | Val | Tyr | Lys | Pro | Ile | Ile | Lys | Lys | Tyr | Thr | Lys |      |
|     |     |     | 645 |     |     |     |     | 650 |     |     |     |     | 655 |     |     |      |
| ATC | ATT | GAT | GGA | GTG | CCT | GTG | GAA | ATA | ACT | GAA | AAA | GAG | ACA | CGA | GAA | 2119 |
| Ile | Ile | Asp | Gly | Val | Pro | Val | Glu | Ile | Thr | Glu | Lys | Glu | Thr | Arg | Glu |      |
|     |     | 660 |     |     |     |     | 665 |     |     |     |     | 670 |     |     |     |      |
| GAA | CGA | ATC | ATT | ACA | GGT | CCT | GAA | ATA | AAA | TAC | ACT | AGG | ATT | TCT | ACT | 2167 |
| Glu | Arg | Ile | Ile | Thr | Gly | Pro | Glu | Ile | Lys | Tyr | Thr | Arg | Ile | Ser | Thr |      |
|     | 675 |     |     |     |     | 680 |     |     |     |     | 685 |     |     |     |     |      |
| GGA | GGT | GGA | GAA | ACA | GAA | GAA | ACT | CTG | AAG | AAA | TTG | TTA | CAA | GAA | GAG | 2215 |
| Gly | Gly | Gly | Glu | Thr | Glu | Glu | Thr | Leu | Lys | Lys | Leu | Leu | Gln | Glu | Glu |      |
| 690 |     |     |     |     | 695 |     |     |     |     | 700 |     |     |     |     | 705 |      |
| GTC | ACC | AAG | GTC | ACC | AAA | TTC | ATT | GAA | GGT | GGT | GAT | GGT | CAT | TTA | TTT | 2263 |
| Val | Thr | Lys | Val | Thr | Lys | Phe | Ile | Glu | Gly | Gly | Asp | Gly | His | Leu | Phe |      |

```
                          710                    715                      720
GAA  GAT  GAA  GAA  ATT  AAA  AGA  CTG  CTT  CAG  GGA  GAC  ACA  CCC  GTG  AGG         2311
Glu  Asp  Glu  Glu  Ile  Lys  Arg  Leu  Leu  Gln  Gly  Asp  Thr  Pro  Val  Arg
               725                    730                     735

AAG  TTG  CAA  GCC  AAC  AAA  AAA  GTT  CAA  GGT  TCT  AGA  AGA  CGA  TTA  AGG         2359
Lys  Leu  Gln  Ala  Asn  Lys  Lys  Val  Gln  Gly  Ser  Arg  Arg  Arg  Leu  Arg
               740                    745                     750

GAA  GGT  CGT  TCT  CAGTGAAAAT  CCAAAAACCA  GAAAAAAATG  TTTATACAAC                      2411
Glu  Gly  Arg  Ser  Gln
               755

CCTAAGTCAA   TAACCTGACC   TTAGAAAATT   GTGAGAGCCA   AGTTGACTTC   AGGAACTGAA             2471
ACATCAGCAC   AAAGAAGCAA   TCATCAAATA   ATTCTGAACA   CAAATTTAAT   ATTTTTTTT              2531
CTGAATGAGA   AACATGAGGG   AAATTGTGGA   GTTAGCCTCC   TGTGGAGTTA   GCCTCCTGTG             2591
GTAAAGGAAT   TGAAGAAAAT   ATAACACCTT   ACACCCTTTT   TCATCTTGAC   ATTAAAAGTT             2651
CTGGCTAACT   TTGGAATCCA   TTAGAGAAAA   ATCCTTGTCA   CCAGATTCAT   TACAATTCAA             2711
ATCGAAGAGT   TGTGAACTGT   TATCCCATTG   AAAAGACCGA   GCCTTGTATG   TATGTTATGG             2771
ATACATAAAA   TGCACGCAAG   CCATTATCTC   TCCATGGGAA   GCTAAGTTAT   AAAAATAGGT             2831
GCTTGGTGTA   CAAAACTTTT   TATATCAAAA   GGCTTTGCAC   ATTTCTATAT   GAGTGGGTTT             2891
ACTGGTAAAT   TATGTTATTT   TTTACAACTA   ATTTGTACT    CTCAGAATGT   TTGTCATATG             2951
CTTCTTGCAA   TGCATATTTT   TTAATCTCAA   ACGTTTCAAT   AAAACCATTT   TTCAGATATA             3011
AAGAGAATTA   CTTCAAATTG   AGTAATTCAG   AAAAACTCAA   GATTTAAGTT   AAAAAGTGGT             3071
TTGGACTTGG   GAACAGGACT   T                                                            3092
```

( 2 ) INFORMATION FOR SEQ ID NO:4:

( i ) SEQUENCE CHARACTERISTICS:
        ( A ) LENGTH: 779 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ile  Pro  Phe  Leu  Pro  Met  Phe  Ser  Leu  Leu  Leu  Leu  Ile  Val
-21  -20                      -15                          -10

Asn  Pro  Ile  Asn  Ala  Asn  Asn  His  Tyr  Asp  Lys  Ile  Leu  Ala  His  Ser
 -5                     1                 5                          10

Arg  Ile  Arg  Gly  Arg  Asp  Gln  Gly  Pro  Asn  Val  Cys  Ala  Leu  Gln  Gln
               15                    20                     25

Ile  Leu  Gly  Thr  Lys  Lys  Lys  Tyr  Phe  Ser  Thr  Cys  Lys  Asn  Trp  Tyr
          30                    35                    40

Lys  Lys  Ser  Ile  Cys  Gly  Gln  Lys  Thr  Thr  Val  Leu  Tyr  Glu  Cys  Cys
     45                     50                    55

Pro  Gly  Tyr  Met  Arg  Met  Glu  Gly  Met  Lys  Gly  Cys  Pro  Ala  Val  Leu
60                       65                    70                          75

Pro  Ile  Asp  His  Val  Tyr  Gly  Thr  Leu  Gly  Ile  Val  Gly  Ala  Thr  Thr
               80                    85                    90

Thr  Gln  Arg  Tyr  Ser  Asp  Ala  Ser  Lys  Leu  Arg  Glu  Glu  Ile  Glu  Gly
          95                    100                   105

Lys  Gly  Ser  Phe  Thr  Tyr  Phe  Ala  Pro  Ser  Asn  Glu  Ala  Trp  Asp  Asn
          110                   115                   120

Leu  Asp  Ser  Asp  Ile  Arg  Arg  Gly  Leu  Glu  Ser  Asn  Val  Asn  Val  Glu
     125                   130                   135
```

```
Leu Leu Asn Ala Leu His Ser His Met Ile Asn Lys Arg Met Leu Thr
140             145                 150                 155

Lys Asp Leu Lys Asn Gly Met Ile Ile Pro Ser Met Tyr Asn Asn Leu
                160                 165                 170

Gly Leu Phe Ile Asn His Tyr Pro Asn Gly Val Val Thr Val Asn Cys
            175                 180                 185

Ala Arg Ile Ile His Gly Asn Gln Ile Ala Thr Asn Gly Val Val His
        190                 195                 200

Val Ile Asp Arg Val Leu Thr Gln Ile Gly Thr Ser Ile Gln Asp Phe
    205                 210                 215

Ile Glu Ala Glu Asp Asp Leu Ser Ser Phe Arg Ala Ala Ala Ile Thr
220             225                 230                 235

Ser Asp Ile Leu Glu Ala Leu Gly Arg Asp Gly His Phe Thr Leu Phe
                240                 245                 250

Ala Pro Thr Asn Glu Ala Phe Glu Lys Leu Pro Arg Gly Val Leu Glu
            255                 260                 265

Arg Phe Met Gly Asp Lys Val Ala Ser Glu Ala Leu Met Lys Tyr His
        270                 275                 280

Ile Leu Asn Thr Leu Gln Cys Ser Glu Ser Ile Met Gly Gly Ala Val
    285                 290                 295

Phe Glu Thr Leu Glu Gly Asn Thr Ile Glu Ile Gly Cys Asp Gly Asp
300             305                 310                 315

Ser Ile Thr Val Asn Gly Ile Lys Met Val Asn Lys Lys Asp Ile Val
                320                 325                 330

Thr Asn Asn Gly Val Ile His Leu Ile Asp Gln Val Leu Ile Pro Asp
            335                 340                 345

Ser Ala Lys Gln Val Ile Glu Leu Ala Gly Lys Gln Gln Thr Thr Phe
        350                 355                 360

Thr Asp Leu Val Ala Gln Leu Gly Leu Ala Ser Ala Leu Arg Pro Asp
    365                 370                 375

Gly Glu Tyr Thr Leu Leu Ala Pro Val Asn Asn Ala Phe Ser Asp Asp
380             385                 390                 395

Thr Leu Ser Met Val Gln Arg Leu Leu Lys Leu Ile Leu Gln Asn His
                400                 405                 410

Ile Leu Lys Val Lys Val Gly Leu Asn Glu Leu Tyr Asn Gly Gln Ile
            415                 420                 425

Leu Glu Thr Ile Gly Gly Lys Gln Leu Arg Val Phe Val Tyr Arg Thr
        430                 435                 440

Ala Val Cys Ile Glu Asn Ser Cys Met Glu Lys Gly Ser Lys Gln Gly
    445                 450                 455

Arg Asn Gly Ala Ile His Ile Phe Arg Glu Ile Ile Lys Pro Ala Glu
460             465                 470                 475

Lys Ser Leu His Glu Lys Leu Lys Gln Asp Lys Arg Phe Ser Thr Phe
                480                 485                 490

Leu Ser Leu Leu Glu Ala Ala Asp Leu Lys Glu Leu Leu Thr Gln Pro
            495                 500                 505

Gly Asp Trp Thr Leu Phe Val Pro Thr Asn Asp Ala Phe Lys Gly Met
        510                 515                 520

Thr Ser Glu Glu Lys Glu Ile Leu Ile Arg Asp Lys Asn Ala Leu Gln
    525                 530                 535

Asn Ile Ile Leu Tyr His Leu Thr Pro Gly Val Phe Ile Gly Lys Gly
540             545                 550                 555

Phe Glu Pro Gly Val Thr Asn Ile Leu Lys Thr Thr Gln Gly Ser Lys
                560                 565                 570
```

| | | | | | | | | | | | | | |
|---|---|---|---|---|---|---|---|---|---|---|---|---|---|
| Ile | Phe | Leu | Lys 575 | Glu | Val | Asn | Asp | Thr 580 | Leu | Leu | Val | Asn 585 | Glu | Leu | Lys |
| Ser | Lys | Glu 590 | Ser | Asp | Ile | Met | Thr 595 | Thr | Asn | Gly | Val | Ile 600 | His | Val | Val |
| Asp | Lys 605 | Leu | Leu | Tyr | Pro | Ala 610 | Asp | Thr | Pro | Val | Gly 615 | Asn | Asp | Gln | Leu |
| Leu 620 | Glu | Ile | Leu | Asn | Lys 625 | Leu | Ile | Lys | Tyr | Ile 630 | Gln | Ile | Lys | Phe | Val 635 |
| Arg | Gly | Ser | Thr | Phe 640 | Lys | Glu | Ile | Pro | Val 645 | Thr | Val | Tyr | Lys | Pro 650 | Ile |
| Ile | Lys | Lys | Tyr 655 | Thr | Lys | Ile | Ile | Asp 660 | Gly | Val | Pro | Val | Glu 665 | Ile | Thr |
| Glu | Lys | Glu 670 | Thr | Arg | Glu | Glu | Arg 675 | Ile | Ile | Thr | Gly | Pro 680 | Glu | Ile | Lys |
| Tyr | Thr 685 | Arg | Ile | Ser | Thr | Gly 690 | Gly | Glu | Thr | Glu 695 | Glu | Thr | Leu | Lys |
| Lys 700 | Leu | Leu | Gln | Glu | Glu 705 | Val | Thr | Lys | Val | Thr 710 | Lys | Phe | Ile | Glu | Gly 715 |
| Gly | Asp | Gly | His | Leu 720 | Phe | Glu | Asp | Glu | Glu 725 | Ile | Lys | Arg | Leu | Leu 730 | Gln |
| Gly | Asp | Thr | Pro 735 | Val | Arg | Lys | Leu | Gln 740 | Ala | Asn | Lys | Lys | Val 745 | Gln | Gly |
| Ser | Arg | Arg 750 | Arg | Leu | Arg | Glu | Gly 755 | Arg | Ser | Gln | | | | |

(2) INFORMATION FOR SEQ ID NO:5:

(i) SEQUENCE CHARACTERISTICS:
  (A) LENGTH: 3253 base pairs
  (B) TYPE: nucleic acid
  (C) STRANDEDNESS: double
  (D) TOPOLOGY: linear (ii) MOLECULE TYPE: cDNA to mRNA (vi) ORIGINAL SOURCE:
  (A) ORGANISM: Homo sapiens
  (G) CELL TYPE: osteosarcoma (ix) FEATURE:
  (A) NAME/KEY: CDS
  (B) LOCATION: join(32..2540)

(ix) FEATURE:
  (A) NAME/KEY: mat_peptide
  (B) LOCATION: join(97..2540)

(xi) SEQUENCE DESCRIPTION: SEQ ID NO:5:

```
GAATTCGGAG ATCTACAGGG AGAGACTCAA G ATG ATT CCC TTT TTA CCC ATG        52
                                  Met Ile Pro Phe Leu Pro Met
                                  -21 -20              -15

TTT TCT CTA CTA TTG CTG CTT ATT GTT AAC CCT ATA AAC GCC AAC AAT      100
Phe Ser Leu Leu Leu Leu Leu Ile Val Asn Pro Ile Asn Ala Asn Asn
            -10              -5                       1

CAT TAT GAC AAG ATC TTG GCT CAT AGT CGT ATC AGG GGT CGG GAC CAA      148
His Tyr Asp Lys Ile Leu Ala His Ser Arg Ile Arg Gly Arg Asp Gln
             5               10              15

GGC CCA AAT GTC TGT GCC CTT CAA CAG ATT TTG GGC ACC AAA AAG AAA      196
Gly Pro Asn Val Cys Ala Leu Gln Gln Ile Leu Gly Thr Lys Lys Lys
         20              25              30

TAC TTC AGC ACT TGT AAG AAC TGG TAT AAA AAG TCC ATC TGT GGA CAG      244
Tyr Phe Ser Thr Cys Lys Asn Trp Tyr Lys Lys Ser Ile Cys Gly Gln
```

-continued

```
             35                          40                            45                         50
AAA   ACG   ACT   GTT   TTA   TAT   GAA   TGT   TGC   CCT   GGT   TAT   ATG   AGA   ATG   GAA        292
Lys   Thr   Thr   Val   Leu   Tyr   Glu   Cys   Cys   Pro   Gly   Tyr   Met   Arg   Met   Glu
                         55                      60                            65

GGA   ATG   AAA   GGC   TGC   CCA   GCA   GTT   TTG   CCC   ATT   GAC   CAT   GTT   TAT   GGC        340
Gly   Met   Lys   Gly   Cys   Pro   Ala   Val   Leu   Pro   Ile   Asp   His   Val   Tyr   Gly
                   70                            75                            80

ACT   CTG   GGC   ATC   GTG   GGA   GCC   ACC   ACA   ACG   CAG   CGC   TAT   TCT   GAC   GCC        388
Thr   Leu   Gly   Ile   Val   Gly   Ala   Thr   Thr   Thr   Gln   Arg   Tyr   Ser   Asp   Ala
             85                            90                            95

TCA   AAA   CTG   AGG   GAG   GAG   ATC   GAG   GGA   AAG   GGA   TCC   TTC   ACT   TAC   TTT        436
Ser   Lys   Leu   Arg   Glu   Glu   Ile   Glu   Gly   Lys   Gly   Ser   Phe   Thr   Tyr   Phe
       100                     105                     110

GCA   CCG   AGT   AAT   GAG   GCT   TGG   GAC   AAC   TTG   GAT   TCT   GAT   ATC   CGT   AGA        484
Ala   Pro   Ser   Asn   Glu   Ala   Trp   Asp   Asn   Leu   Asp   Ser   Asp   Ile   Arg   Arg
115                     120                     125                           130

GGT   TTG   GAG   AGC   AAC   GTG   AAT   GTT   GAA   TTA   CTG   AAT   GCT   TTA   CAT   AGT        532
Gly   Leu   Glu   Ser   Asn   Val   Asn   Val   Glu   Leu   Leu   Asn   Ala   Leu   His   Ser
                         135                     140                           145

CAC   ATG   ATT   AAT   AAG   AGA   ATG   TTG   ACC   AAG   GAC   TTA   AAA   AAT   GGC   ATG        580
His   Met   Ile   Asn   Lys   Arg   Met   Leu   Thr   Lys   Asp   Leu   Lys   Asn   Gly   Met
                   150                           155                           160

ATT   ATT   CCT   TCA   ATG   TAT   AAC   AAT   TTG   GGG   CTT   TTC   ATT   AAC   CAT   TAT        628
Ile   Ile   Pro   Ser   Met   Tyr   Asn   Asn   Leu   Gly   Leu   Phe   Ile   Asn   His   Tyr
                   165                           170                           175

CCT   AAT   GGG   GTT   GTC   ACT   GTT   AAT   TGT   GCT   CGA   ATC   ATC   CAT   GGG   AAC        676
Pro   Asn   Gly   Val   Val   Thr   Val   Asn   Cys   Ala   Arg   Ile   Ile   His   Gly   Asn
             180                           185                           190

CAG   ATT   GCA   ACA   AAT   GGT   GTT   GTC   CAT   GTC   ATT   GAC   CGT   GTG   CTT   ACA        724
Gln   Ile   Ala   Thr   Asn   Gly   Val   Val   His   Val   Ile   Asp   Arg   Val   Leu   Thr
195                     200                     205                           210

CAA   ATT   GGT   ACC   TCA   ATT   CAA   GAC   TTC   ATT   GAA   GCA   GAA   GAT   GAC   CTT        772
Gln   Ile   Gly   Thr   Ser   Ile   Gln   Asp   Phe   Ile   Glu   Ala   Glu   Asp   Asp   Leu
                         215                     220                           225

TCA   TCT   TTT   AGA   GCA   GCT   GCC   ATC   ACA   TCG   GAC   ATA   TTG   GAG   GCC   CTT        820
Ser   Ser   Phe   Arg   Ala   Ala   Ala   Ile   Thr   Ser   Asp   Ile   Leu   Glu   Ala   Leu
             230                           235                           240

GGA   AGA   GAC   GGT   CAC   TTC   ACA   CTC   TTT   GCT   CCC   ACC   AAT   GAG   GCT   TTT        868
Gly   Arg   Asp   Gly   His   Phe   Thr   Leu   Phe   Ala   Pro   Thr   Asn   Glu   Ala   Phe
             245                           250                           255

GAG   AAA   CTT   CCA   CGA   GGT   GTC   CTA   GAA   AGG   TTC   ATG   GGA   GAC   AAA   GTG        916
Glu   Lys   Leu   Pro   Arg   Gly   Val   Leu   Glu   Arg   Phe   Met   Gly   Asp   Lys   Val
       260                     265                     270

GCT   TCC   GAA   GCT   CTT   ATG   AAG   TAC   CAC   ATC   TTA   AAT   ACT   CTC   CAG   TGT        964
Ala   Ser   Glu   Ala   Leu   Met   Lys   Tyr   His   Ile   Leu   Asn   Thr   Leu   Gln   Cys
275                     280                     285                           290

TCT   GAG   TCT   ATT   ATG   GGA   GGA   GCA   GTC   TTT   GAG   ACG   CTG   GAA   GGA   AAT       1012
Ser   Glu   Ser   Ile   Met   Gly   Gly   Ala   Val   Phe   Glu   Thr   Leu   Glu   Gly   Asn
                         295                     300                           305

ACA   ATT   GAG   ATA   GGA   TGT   GAC   GGT   GAC   AGT   ATA   ACA   GTA   AAT   GGA   ATC       1060
Thr   Ile   Glu   Ile   Gly   Cys   Asp   Gly   Asp   Ser   Ile   Thr   Val   Asn   Gly   Ile
                   310                           315                           320

AAA   ATG   GTG   AAC   AAA   AAG   GAT   ATT   GTG   ACA   AAT   AAT   GGT   GTG   ATC   CAT       1108
Lys   Met   Val   Asn   Lys   Lys   Asp   Ile   Val   Thr   Asn   Asn   Gly   Val   Ile   His
             325                           330                           335

TTG   ATT   GAT   CAG   GTC   CTA   ATT   CCT   GAT   TCT   GCC   AAA   CAA   GTT   ATT   GAG       1156
Leu   Ile   Asp   Gln   Val   Leu   Ile   Pro   Asp   Ser   Ala   Lys   Gln   Val   Ile   Glu
       340                     345                     350

CTG   GCT   GGA   AAA   CAG   CAA   ACC   ACC   TTC   ACG   GAT   CTT   GTG   GCC   CAA   TTA       1204
Leu   Ala   Gly   Lys   Gln   Gln   Thr   Thr   Phe   Thr   Asp   Leu   Val   Ala   Gln   Leu
```

| | | | | | | | | | | | | | | | |
|---|---|---|---|---|---|---|---|---|---|---|---|---|---|---|---|
| 355 | | | | 360 | | | | 365 | | | | 370 | | | |
| GGC | TTG | GCA | TCT | GCT | CTG | AGG | CCA | GAT | GGA | GAA | TAC | ACT | TTG | CTG | GCA | 1252 |
| Gly | Leu | Ala | Ser | Ala | Leu | Arg | Pro | Asp | Gly | Glu | Tyr | Thr | Leu | Leu | Ala | |
| | | | 375 | | | | 380 | | | | | | 385 | | | |
| CCT | GTG | AAT | AAT | GCA | TTT | TCT | GAT | GAT | ACT | CTC | AGC | ATG | GTT | CAG | CGC | 1300 |
| Pro | Val | Asn | Asn | Ala | Phe | Ser | Asp | Asp | Thr | Leu | Ser | Met | Val | Gln | Arg | |
| | | | 390 | | | | 395 | | | | | | 400 | | | |
| CTC | CTT | AAA | TTA | ATT | CTG | CAG | AAT | CAC | ATA | TTG | AAA | GTA | AAA | GTT | GGC | 1348 |
| Leu | Leu | Lys | Leu | Ile | Leu | Gln | Asn | His | Ile | Leu | Lys | Val | Lys | Val | Gly | |
| | | 405 | | | | | 410 | | | | | 415 | | | | |
| CTT | AAT | GAG | CTT | TAC | AAC | GGG | CAA | ATA | CTG | GAA | ACC | ATC | GGA | GGC | AAA | 1396 |
| Leu | Asn | Glu | Leu | Tyr | Asn | Gly | Gln | Ile | Leu | Glu | Thr | Ile | Gly | Gly | Lys | |
| | 420 | | | | 425 | | | | | 430 | | | | | | |
| CAG | CTC | AGA | GTC | TTC | GTA | TAT | CGT | ACA | GCT | GTC | TGC | ATT | GAA | AAT | TCA | 1444 |
| Gln | Leu | Arg | Val | Phe | Val | Tyr | Arg | Thr | Ala | Val | Cys | Ile | Glu | Asn | Ser | |
| 435 | | | | 440 | | | | | 445 | | | | | | 450 | |
| TGC | ATG | GAG | AAA | GGG | AGT | AAG | CAA | GGG | AGA | AAC | GGT | GCG | ATT | CAC | ATA | 1492 |
| Cys | Met | Glu | Lys | Gly | Ser | Lys | Gln | Gly | Arg | Asn | Gly | Ala | Ile | His | Ile | |
| | | | | 455 | | | | | 460 | | | | | 465 | | |
| TTC | CGC | GAG | ATC | ATC | AAG | CCA | GCA | GAG | AAA | TCC | CTC | CAT | GAA | AAG | TTA | 1540 |
| Phe | Arg | Glu | Ile | Ile | Lys | Pro | Ala | Glu | Lys | Ser | Leu | His | Glu | Lys | Leu | |
| | | | 470 | | | | | 475 | | | | | 480 | | | |
| AAA | CAA | GAT | AAG | CGC | TTT | AGC | ACC | TTC | CTC | AGC | CTA | CTT | GAA | GCT | GCA | 1588 |
| Lys | Gln | Asp | Lys | Arg | Phe | Ser | Thr | Phe | Leu | Ser | Leu | Leu | Glu | Ala | Ala | |
| | | 485 | | | | | 490 | | | | | 495 | | | | |
| GAC | TTG | AAA | GAG | CTC | CTG | ACA | CAA | CCT | GGA | GAC | TGG | ACA | TTA | TTT | GTG | 1636 |
| Asp | Leu | Lys | Glu | Leu | Leu | Thr | Gln | Pro | Gly | Asp | Trp | Thr | Leu | Phe | Val | |
| | 500 | | | | | 505 | | | | | 510 | | | | | |
| CCA | ACC | AAT | GAT | GCT | TTT | AAG | GGA | ATG | ACT | AGT | GAA | GAA | AAA | GAA | ATT | 1684 |
| Pro | Thr | Asn | Asp | Ala | Phe | Lys | Gly | Met | Thr | Ser | Glu | Glu | Lys | Glu | Ile | |
| 515 | | | | | 520 | | | | | 525 | | | | | 530 | |
| CTG | ATA | CGG | GAC | AAA | AAT | GCT | CTT | CAA | AAC | ATC | ATT | CTT | TAT | CAC | CTG | 1732 |
| Leu | Ile | Arg | Asp | Lys | Asn | Ala | Leu | Gln | Asn | Ile | Ile | Leu | Tyr | His | Leu | |
| | | | 535 | | | | | 540 | | | | | 545 | | | |
| ACA | CCA | GGA | GTT | TTC | ATT | GGA | AAA | GGA | TTT | GAA | CCT | GGT | GTT | ACT | AAC | 1780 |
| Thr | Pro | Gly | Val | Phe | Ile | Gly | Lys | Gly | Phe | Glu | Pro | Gly | Val | Thr | Asn | |
| | | | 550 | | | | | 555 | | | | | 560 | | | |
| ATT | TTA | AAG | ACC | ACA | CAA | GGA | AGC | AAA | ATC | TTT | CTG | AAA | GAA | GTA | AAT | 1828 |
| Ile | Leu | Lys | Thr | Thr | Gln | Gly | Ser | Lys | Ile | Phe | Leu | Lys | Glu | Val | Asn | |
| | | 565 | | | | | 570 | | | | | 575 | | | | |
| GAT | ACA | CTT | CTG | GTG | AAT | GAA | TTG | AAA | TCA | AAA | GAA | TCT | GAC | ATC | ATG | 1876 |
| Asp | Thr | Leu | Leu | Val | Asn | Glu | Leu | Lys | Ser | Lys | Glu | Ser | Asp | Ile | Met | |
| | 580 | | | | | 585 | | | | | 590 | | | | | |
| ACA | ACA | AAT | GGT | GTA | ATT | CAT | GTT | GTA | GAT | AAA | CTC | CTC | TAT | CCA | GCA | 1924 |
| Thr | Thr | Asn | Gly | Val | Ile | His | Val | Val | Asp | Lys | Leu | Leu | Tyr | Pro | Ala | |
| 595 | | | | | 600 | | | | | 605 | | | | | 610 | |
| GAC | ACA | CCT | GTT | GGA | AAT | GAT | CAA | CTG | CTG | GAA | ATA | CTT | AAT | AAA | TTA | 1972 |
| Asp | Thr | Pro | Val | Gly | Asn | Asp | Gln | Leu | Leu | Glu | Ile | Leu | Asn | Lys | Leu | |
| | | | | 615 | | | | | 620 | | | | | 625 | | |
| ATC | AAA | TAC | ATC | CAA | ATT | AAG | TTT | GTT | CGT | GGT | AGC | ACC | TTC | AAA | GAA | 2020 |
| Ile | Lys | Tyr | Ile | Gln | Ile | Lys | Phe | Val | Arg | Gly | Ser | Thr | Phe | Lys | Glu | |
| | | | 630 | | | | | 635 | | | | | 640 | | | |
| ATC | CCC | GTG | ACT | GTC | TAT | ACA | ACT | AAA | ATT | ATA | ACC | AAA | GTT | GTG | GAA | 2068 |
| Ile | Pro | Val | Thr | Val | Tyr | Thr | Thr | Lys | Ile | Ile | Thr | Lys | Val | Val | Glu | |
| | | | 645 | | | | 650 | | | | | 655 | | | | |
| CCA | AAA | ATT | AAA | GTG | ATT | GAA | GGC | AGT | CTT | CAG | CCT | ATT | ATC | AAA | ACT | 2116 |
| Pro | Lys | Ile | Lys | Val | Ile | Glu | Gly | Ser | Leu | Gln | Pro | Ile | Ile | Lys | Thr | |
| | 660 | | | | | 665 | | | | | 670 | | | | | |
| GAA | GGA | CCC | ACA | CTA | ACA | AAA | GTC | AAA | ATT | GAA | GGT | GAA | CCT | GAA | TTC | 2164 |
| Glu | Gly | Pro | Thr | Leu | Thr | Lys | Val | Lys | Ile | Glu | Gly | Glu | Pro | Glu | Phe | |

| | | | | | | | | | | | | | | | | |
|---|---|---|---|---|---|---|---|---|---|---|---|---|---|---|---|---|
|AGA|CTG|ATT|AAA|GAA|GGT|GAA|ACA|ATA|ACT|GAA|GTG|ATC|CAT|GGA|GAG|2212|
|Arg|Leu|Ile|Lys|Glu|Gly|Glu|Thr|Ile|Thr|Glu|Val|Ile|His|Gly|Glu||
| | | |695| | | | |700| | | |705| | | | |
|CCA|ATT|ATT|AAA|AAA|TAC|ACC|AAA|ATC|ATT|GAT|GGA|GTG|CCT|GTG|GAA|2260|
|Pro|Ile|Ile|Lys|Lys|Tyr|Thr|Lys|Ile|Ile|Asp|Gly|Val|Pro|Val|Glu||
| | | |710| | | |715| | | | |720| | | | |
|ATA|ACT|GAA|AAA|GAG|ACA|CGA|GAA|GAA|CGA|ATC|ATT|ACA|GGT|CCT|GAA|2308|
|Ile|Thr|Glu|Lys|Glu|Thr|Arg|Glu|Glu|Arg|Ile|Ile|Thr|Gly|Pro|Glu||
| | |725| | | |730| | | | |735| | | | | |
|ATA|AAA|TAC|ACT|AGG|ATT|TCT|ACT|GGA|GGT|GGA|GAA|ACA|GAA|GAA|ACT|2356|
|Ile|Lys|Tyr|Thr|Arg|Ile|Ser|Thr|Gly|Gly|Gly|Glu|Thr|Glu|Glu|Thr||
| |740| | | |745| | | | |750| | | | | | |
|CTG|AAG|AAA|TTG|TTA|CAA|GAA|GAG|GTC|ACC|AAG|GTC|ACC|AAA|TTC|ATT|2404|
|Leu|Lys|Lys|Leu|Leu|Gln|Glu|Glu|Val|Thr|Lys|Val|Thr|Lys|Phe|Ile||
|755| | | | |760| | | | |765| | | | |770| |
|GAA|GGT|GGT|GAT|GGT|CAT|TTA|TTT|GAA|GAT|GAA|GAA|ATT|AAA|AGA|CTG|2452|
|Glu|Gly|Gly|Asp|Gly|His|Leu|Phe|Glu|Asp|Glu|Glu|Ile|Lys|Arg|Leu||
| | | | |775| | | |780| | | | |785| | | |
|CTT|CAG|GGA|GAC|ACA|CCC|GTG|AGG|AAG|TTG|CAA|GCC|AAC|AAA|AAA|GTT|2500|
|Leu|Gln|Gly|Asp|Thr|Pro|Val|Arg|Lys|Leu|Gln|Ala|Asn|Lys|Lys|Val||
| | | |790| | | |795| | | | |800| | | | |
|CAA|GGT|TCT|AGA|AGA|CGA|TTA|AGG|GAA|GGT|CGT|TCT|CAGTGAAAAT| | | |2546|
|Gln|Gly|Ser|Arg|Arg|Arg|Leu|Arg|Glu|Gly|Arg|Ser|Gln| | | | |
| | |805| | | |810| | | | |815| | | | | |

| | | | | |
|---|---|---|---|---|
|CCAAAAACCA|GAAAAAAATG|TTTATACAAC|CCTAAGTCAA|TAACCTGACC TTAGAAAATT|2606|
|GTGAGAGCCA|AGTTGACTTC|AGGAACTGAA|ACATCAGCAC|AAAGAAGCAA TCATCAAATA|2666|
|ATTCTGAACA|CAAATTTAAT|ATTTTTTTT|CTGAATGAGA|AACATGAGGG AAATTGTGGA|2726|
|GTTAGCCTCC|TGTGGTAAAG|GAATTGAAGA|AAATATAACA|CCTTACACCC TTTTTCATCT|2786|
|TGACATTAAA|AGTTCTGGCT|AACTTTGGAA|TCCATTAGAG|AAAAATCCTT GTCACCAGAT|2846|
|TCATTACAAT|TCAAATCGAA|GAGTTGTGAA|CTGTTATCCC|ATTGAAAAGA CCGAGCCTTG|2906|
|TATGTATGTT|ATGGATACAT|AAAATGCACG|CAAGCCATTA|TCTCTCCATG GGAAGCTAAG|2966|
|TTATAAAAAT|AGGTGCTTGG|TGTACAAAAC|TTTTTATATC|AAAAGGCTTT GCACATTTCT|3026|
|ATATGAGTGG|GTTTACTGGT|AAATTATGTT|ATTTTTTACA|ACTAATTTTG TACTCTCAGA|3086|
|ATGTTTGTCA|TATGCTTCTT|GCAATGCATA|TTTTTAATC|TCAAACGTTT CAATAAAACC|3146|
|ATTTTTCAGA|TATAAAGAGA|ATTACTTCAA|ATTGAGTAAT|TCAGAAAAAC TCAAGATTTA|3206|
|AGTTAAAAAG|TGGTTTGGAC|TTGGGAACCC|TGTAGATCTC|CGAATTC|3253|

( 2 ) INFORMATION FOR SEQ ID NO:6:

( i ) SEQUENCE CHARACTERISTICS:
        ( A ) LENGTH: 836 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
|Met|Ile|Pro|Phe|Leu|Pro|Met|Phe|Ser|Leu|Leu|Leu|Leu|Ile|Val|
|-21| |-20| | | |-15| | | | |-10| | | |
|Asn|Pro|Ile|Asn|Ala|Asn|Asn|His|Tyr|Asp|Lys|Ile|Leu|Ala|His|Ser|
|-5| | | |1| | | |5| | | | | |10| |
|Arg|Ile|Arg|Gly|Arg|Asp|Gln|Gly|Pro|Asn|Val|Cys|Ala|Leu|Gln|Gln|
| | | |15| | | |20| | | | |25| | | |
|Ile|Leu|Gly|Thr|Lys|Lys|Lys|Tyr|Phe|Ser|Thr|Cys|Lys|Asn|Trp|Tyr|

-continued

|  | 30 |  |  |  | 35 |  |  |  | 40 |  |  |  |
|---|---|---|---|---|---|---|---|---|---|---|---|---|
| Lys | Lys 45 | Ser | Ile | Cys | Gly 50 | Gln | Lys | Thr | Thr 55 | Val | Leu | Tyr | Glu | Cys | Cys |
| Pro 60 | Gly | Tyr | Met | Arg | Met 65 | Glu | Gly | Met | Lys 70 | Gly | Cys | Pro | Ala | Val | Leu 75 |
| Pro | Ile | Asp | His | Val 80 | Tyr | Gly | Thr | Leu | Gly 85 | Ile | Val | Gly | Ala | Thr 90 | Thr |
| Thr | Gln | Arg | Tyr 95 | Ser | Asp | Ala | Ser | Lys 100 | Leu | Arg | Glu | Glu | Ile 105 | Glu | Gly |
| Lys | Gly | Ser 110 | Phe | Thr | Tyr | Phe | Ala 115 | Pro | Ser | Asn | Glu | Ala 120 | Trp | Asp | Asn |
| Leu | Asp 125 | Ser | Asp | Ile | Arg | Arg 130 | Gly | Leu | Glu | Ser | Asn 135 | Val | Asn | Val | Glu |
| Leu 140 | Leu | Asn | Ala | Leu | His 145 | Ser | His | Met | Ile | Asn 150 | Lys | Arg | Met | Leu | Thr 155 |
| Lys | Asp | Leu | Lys | Asn 160 | Gly | Met | Ile | Ile | Pro 165 | Ser | Met | Tyr | Asn | Asn 170 | Leu |
| Gly | Leu | Phe | Ile 175 | Asn | His | Tyr | Pro | Asn 180 | Gly | Val | Val | Thr | Val 185 | Asn | Cys |
| Ala | Arg | Ile 190 | Ile | His | Gly | Asn | Gln 195 | Ile | Ala | Thr | Asn | Gly 200 | Val | Val | His |
| Val | Ile 205 | Asp | Arg | Val | Leu | Thr 210 | Gln | Ile | Gly | Thr | Ser 215 | Ile | Gln | Asp | Phe |
| Ile 220 | Glu | Ala | Glu | Asp | Asp 225 | Leu | Ser | Ser | Phe | Arg 230 | Ala | Ala | Ala | Ile | Thr 235 |
| Ser | Asp | Ile | Leu | Glu 240 | Ala | Leu | Gly | Arg | Asp 245 | Gly | His | Phe | Thr | Leu 250 | Phe |
| Ala | Pro | Thr | Asn 255 | Glu | Ala | Phe | Glu | Lys 260 | Leu | Pro | Arg | Gly | Val 265 | Leu | Glu |
| Arg | Phe | Met 270 | Gly | Asp | Lys | Val | Ala 275 | Ser | Glu | Ala | Leu | Met 280 | Lys | Tyr | His |
| Ile | Leu 285 | Asn | Thr | Leu | Gln | Cys 290 | Ser | Glu | Ser | Ile | Met 295 | Gly | Gly | Ala | Val |
| Phe 300 | Glu | Thr | Leu | Glu | Gly 305 | Asn | Thr | Ile | Glu | Ile 310 | Gly | Cys | Asp | Gly | Asp 315 |
| Ser | Ile | Thr | Val | Asn 320 | Gly | Ile | Lys | Met | Val 325 | Asn | Lys | Lys | Asp | Ile 330 | Val |
| Thr | Asn | Asn | Gly 335 | Val | Ile | His | Leu | Ile 340 | Asp | Gln | Val | Leu | Ile 345 | Pro | Asp |
| Ser | Ala | Lys 350 | Gln | Val | Ile | Glu | Leu 355 | Ala | Gly | Lys | Gln | Gln 360 | Thr | Thr | Phe |
| Thr | Asp 365 | Leu | Val | Ala | Gln | Leu 370 | Gly | Leu | Ala | Ser | Ala 375 | Leu | Arg | Pro | Asp |
| Gly 380 | Glu | Tyr | Thr | Leu | Leu 385 | Ala | Pro | Val | Asn | Asn 390 | Ala | Phe | Ser | Asp | Asp 395 |
| Thr | Leu | Ser | Met | Val 400 | Gln | Arg | Leu | Leu | Lys 405 | Leu | Ile | Leu | Gln | Asn 410 | His |
| Ile | Leu | Lys | Val 415 | Lys | Val | Gly | Leu | Asn 420 | Glu | Leu | Tyr | Asn | Gly 425 | Gln | Ile |
| Leu | Glu | Thr 430 | Ile | Gly | Gly | Lys | Gln 435 | Leu | Arg | Val | Phe | Val 440 | Tyr | Arg | Thr |
| Ala | Val 445 | Cys | Ile | Glu | Asn | Ser 450 | Cys | Met | Glu | Lys | Gly 455 | Ser | Lys | Gln | Gly |

| | | | | | | | | | | | | | |
|---|---|---|---|---|---|---|---|---|---|---|---|---|---|
| Arg 460 | Asn | Gly | Ala | Ile 465 | His | Ile | Phe | Arg | Glu 470 | Ile | Ile | Lys | Pro | Ala | Glu 475 |
| Lys | Ser | Leu | His | Glu 480 | Lys | Leu | Lys | Gln | Asp 485 | Lys | Arg | Phe | Ser | Thr 490 | Phe |
| Leu | Ser | Leu | Leu 495 | Glu | Ala | Ala | Asp | Leu 500 | Lys | Glu | Leu | Leu 505 | Thr | Gln | Pro |
| Gly | Asp | Trp 510 | Thr | Leu | Phe | Val | Pro 515 | Thr | Asn | Asp | Ala | Phe 520 | Lys | Gly | Met |
| Thr | Ser 525 | Glu | Glu | Lys | Glu | Ile 530 | Leu | Ile | Arg | Asp | Lys 535 | Asn | Ala | Leu | Gln |
| Asn 540 | Ile | Ile | Leu | Tyr | His 545 | Leu | Thr | Pro | Gly | Val 550 | Phe | Ile | Gly | Lys | Gly 555 |
| Phe | Glu | Pro | Gly | Val 560 | Thr | Asn | Ile | Leu | Lys 565 | Thr | Thr | Gln | Gly | Ser 570 | Lys |
| Ile | Phe | Leu | Lys 575 | Glu | Val | Asn | Asp | Thr 580 | Leu | Leu | Val | Asn 585 | Glu | Leu | Lys |
| Ser | Lys | Glu 590 | Ser | Asp | Ile | Met | Thr 595 | Thr | Asn | Gly | Val | Ile 600 | His | Val | Val |
| Asp | Lys 605 | Leu | Leu | Tyr | Pro | Ala 610 | Asp | Thr | Pro | Val | Gly 615 | Asn | Asp | Gln | Leu |
| Leu 620 | Glu | Ile | Leu | Asn | Lys 625 | Leu | Ile | Lys | Tyr | Ile 630 | Gln | Ile | Lys | Phe | Val 635 |
| Arg | Gly | Ser | Thr | Phe 640 | Lys | Glu | Ile | Pro | Val 645 | Thr | Val | Tyr | Thr | Thr 650 | Lys |
| Ile | Ile | Thr | Lys 655 | Val | Val | Glu | Pro | Lys 660 | Ile | Lys | Val | Ile 665 | Glu | Gly | Ser |
| Leu | Gln | Pro 670 | Ile | Ile | Lys | Thr | Glu 675 | Gly | Pro | Thr | Leu | Thr 680 | Lys | Val | Lys |
| Ile | Glu 685 | Gly | Glu | Pro | Glu | Phe 690 | Arg | Leu | Ile | Lys | Glu 695 | Gly | Glu | Thr | Ile |
| Thr 700 | Glu | Val | Ile | His | Gly 705 | Glu | Pro | Ile | Ile | Lys 710 | Lys | Tyr | Thr | Lys | Ile 715 |
| Ile | Asp | Gly | Val | Pro 720 | Val | Glu | Ile | Thr | Glu 725 | Lys | Glu | Thr | Arg | Glu 730 | Glu |
| Arg | Ile | Ile | Thr 735 | Gly | Pro | Glu | Ile | Lys 740 | Tyr | Thr | Arg | Ile | Ser 745 | Thr | Gly |
| Gly | Gly | Glu 750 | Thr | Glu | Glu | Thr | Leu 755 | Lys | Lys | Leu | Leu | Gln 760 | Glu | Glu | Val |
| Thr | Lys 765 | Val | Thr | Lys | Phe | Ile 770 | Glu | Gly | Gly | Asp | Gly 775 | His | Leu | Phe | Glu |
| Asp 780 | Glu | Glu | Ile | Lys | Arg 785 | Leu | Leu | Gln | Gly | Asp 790 | Thr | Pro | Val | Arg | Lys 795 |
| Leu | Gln | Ala | Asn | Lys 800 | Lys | Val | Gln | Gly | Ser 805 | Arg | Arg | Arg | Leu | Arg 810 | Glu |
| Gly | Arg | Ser | Gln 815 | | | | | | | | | | | | |

( 2 ) INFORMATION FOR SEQ ID NO:7:

( i ) SEQUENCE CHARACTERISTICS:
        ( A ) LENGTH: 62 base pairs
        ( B ) TYPE: nucleic acid
        ( C ) STRANDEDNESS: double
        ( D ) TOPOLOGY: linear ( i i ) MOLECULE TYPE: Other
        ( A ) DESCRIPTION: other nucleic acid ( i x ) FEATURE:
    ( A ) NAME/KEY: misc_feature
    ( B ) LOCATION: 5..59
    ( D ) OTHER INFORMATION: /note= "Sequence ID No. 7 is
        complementary to Seq ID No. 8 from positions 5 -
        48 of Sequence ID No. 7."

( x i ) SEQUENCE DESCRIPTION: SEQ ID NO:7:

```
CATGCAACAG TTACTATGAC AAGGTCCTGG CTCACAGCCG CATCAGGGGT CGGGATCAGG    60

GC                                                                  62
```

( 2 ) INFORMATION FOR SEQ ID NO:8:

( i ) SEQUENCE CHARACTERISTICS:
        ( A ) LENGTH: 55 base pairs
        ( B ) TYPE: nucleic acid
        ( C ) STRANDEDNESS: double
        ( D ) TOPOLOGY: linear ( i i ) MOLECULE TYPE: Other
        ( A ) DESCRIPTION: other nucleic acid ( i x ) FEATURE:
        ( A ) NAME/KEY: misc_feature
        ( B ) LOCATION: 1..55
        ( D ) OTHER INFORMATION: /note= "Sequence ID No. 8 is
            complementary to Sequence ID No. 7 from positions
            1-55 of Sequence ID No. 8."

( x i ) SEQUENCE DESCRIPTION: SEQ ID NO:8:

```
CTGATCCCGA CCCCTGATGC GGCTGTGAGC CAGGACCTTG TCATAGTAAC TGTTG         55
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Mus musculus ( x i ) SEQUENCE DESCRIPTION: SEQ ID NO:9:

```
Glu Asn Leu Asp Ser Asp Ile Arg Arg Gly Leu Glu Asn Asn Val Asn
 1               5                  10                  15
```

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Mus musculus ( x i ) SEQUENCE DESCRIPTION: SEQ ID NO:10:

```
Glu Lys Ser Leu His Asp Lys Leu Arg Gln Asp Lys Arg
 1               5                  10
```

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear (ii) MOLECULE TYPE: peptide (vi) ORIGINAL SOURCE:
(A) ORGANISM: Mus musculus (xi) SEQUENCE DESCRIPTION: SEQ ID NO:11:

```
Asn Lys Arg Val Gln Gly Pro Arg Arg Arg Ser Arg Glu Gly Arg Ser
1               5                   10                  15
```

(2) INFORMATION FOR SEQ ID NO:12:

(i) SEQUENCE CHARACTERISTICS:
(A) LENGTH: 16 amino acids
(B) TYPE: amino acid
(D) TOPOLOGY: linear (ii) MOLECULE TYPE: peptide (vi) ORIGINAL SOURCE:
(A) ORGANISM: Mus musculus (xi) SEQUENCE DESCRIPTION: SEQ ID NO:12:

```
Gly His Phe Thr Leu Phe Ala Pro Thr Asn Glu Ala Phe Glu Lys Leu
1               5                   10                  15
```

(2) INFORMATION FOR SEQ ID NO:13:

(i) SEQUENCE CHARACTERISTICS:
(A) LENGTH: 18 amino acids
(B) TYPE: amino acid
(D) TOPOLOGY: linear (ii) MOLECULE TYPE: peptide (vi) ORIGINAL SOURCE:
(A) ORGANISM: Mus musculus (xi) SEQUENCE DESCRIPTION: SEQ ID NO:13:

```
Ile Val Thr Lys Asn Gly Val Ile His Leu Ile Asp Glu Val Leu Ile
1               5                   10                  15

Pro Asp
```

(2) INFORMATION FOR SEQ ID NO:14:

(i) SEQUENCE CHARACTERISTICS:
(A) LENGTH: 128 amino acids
(B) TYPE: amino acid
(D) TOPOLOGY: linear (ii) MOLECULE TYPE: peptide (xi) SEQUENCE DESCRIPTION: SEQ ID NO:14:

```
Gly Ile Val Gly Ala Thr Thr Thr Gln Arg Tyr Ser Asp Ala Ser Lys
1               5                   10                  15

Leu Arg Glu Glu Ile Glu Gly Lys Gly Ser Phe Thr Tyr Phe Ala Pro
                20                  25                  30

Ser Asn Glu Ala Trp Asp Asn Leu Asp Ser Asp Ile Arg Arg Gly Leu
                35                  40                  45

Glu Ser Asn Val Asn Val Glu Leu Leu Asn Ala Leu His Ser His Met
        50                  55                  60

Ile Asn Lys Arg Met Leu Thr Lys Asp Leu Lys Asn Gly Met Ile Ile
65                      70                  75                  80

Pro Ser Met Tyr Asn Asn Leu Gly Leu Phe Ile Asn His Tyr Pro Asn
                    85                  90                  95

Gly Val Val Thr Val Asn Cys Ala Arg Ile Ile His Gly Asn Gln Ile
```

|     |     |     |     |     | 100 |     |     |     | 105 |     |     |     |     | 110 |
| --- | --- | --- | --- | --- | --- | --- | --- | --- | --- | --- | --- | --- | --- | --- |

Ala  Thr  Asn  Gly  Val  Val  His  Val  Ile  Asp  Arg  Val  Leu  Thr  Gln  Ile
               115                      120                     125

(2) INFORMATION FOR SEQ ID NO:15:

(i) SEQUENCE CHARACTERISTICS:
       (A) LENGTH: 135 amino acids
       (B) TYPE: amino acid
       (D) TOPOLOGY: linear (ii) MOLECULE TYPE: peptide (xi) SEQUENCE DESCRIPTION: SEQ ID NO:15:

Gly  Thr  Ser  Ile  Gln  Asp  Phe  Ile  Glu  Ala  Glu  Asp  Leu  Ser  Ser
 1                    5                     10                     15

Phe  Arg  Ala  Ala  Ala  Ile  Thr  Ser  Asp  Ile  Leu  Glu  Ala  Leu  Gly  Arg
                20                     25                     30

Asp  Gly  His  Phe  Thr  Leu  Phe  Ala  Pro  Thr  Asn  Glu  Ala  Phe  Glu  Lys
           35                     40                     45

Leu  Pro  Arg  Gly  Val  Leu  Glu  Arg  Phe  Met  Gly  Asp  Lys  Val  Ala  Ser
      50                     55                     60

Glu  Ala  Leu  Met  Asp  Tyr  His  Ile  Leu  Asn  Thr  Leu  Gln  Cys  Ser  Glu
 65                      70                     75                     80

Ser  Ile  Met  Gly  Gly  Ala  Val  Phe  Glu  Thr  Leu  Glu  Gly  Asn  Thr  Ile
                     85                     90                     95

Glu  Ile  Gly  Cys  Asp  Gly  Asp  Ser  Ile  Thr  Val  Asn  Gly  Ile  Lys  Met
                100                    105                    110

Val  Asn  Lys  Lys  Asp  Ile  Val  Thr  Asn  Asn  Gly  Val  Ile  His  Leu  Ile
               115                    120                    125

Asp  Gln  Val  Leu  Ile  Pro  Asp
      130                    135

(2) INFORMATION FOR SEQ ID NO:16:

(i) SEQUENCE CHARACTERISTICS:
       (A) LENGTH: 127 amino acids
       (B) TYPE: amino acid
       (D) TOPOLOGY: linear (ii) MOLECULE TYPE: peptide (xi) SEQUENCE DESCRIPTION: SEQ ID NO:16:

Ser  Ala  Lys  Gln  Val  Ile  Glu  Leu  Ala  Gly  Lys  Gln  Gln  Thr  Thr  Phe
 1                    5                     10                     15

Thr  Asp  Leu  Val  Ala  Gln  Leu  Gly  Leu  Ala  Ser  Ala  Leu  Arg  Pro  Asp
                20                     25                     30

Gly  Glu  Tyr  Thr  Leu  Leu  Ala  Pro  Val  Asn  Asn  Ala  Phe  Ser  Asp  Asp
           35                     40                     45

Thr  Leu  Ser  Met  Val  Gln  Arg  Leu  Leu  Lys  Leu  Ile  Leu  Gln  Asn  His
      50                     55                     60

Ile  Leu  Lys  Val  Lys  Val  Gly  Leu  Asn  Glu  Leu  Tyr  Asn  Gly  Gln  Ile
 65                      70                     75                     80

Leu  Glu  Thr  Ile  Gly  Gly  Lys  Gln  Leu  Arg  Val  Phe  Val  Tyr  Arg  Thr
                     85                     90                     95

Ala  Val  Cys  Ile  Glu  Asn  Ser  Cys  Met  Glu  Lys  Gly  Ser  Lys  Gln  Gly
                100                    105                    110

Arg  Asn  Gly  Ala  Ile  His  Ile  Phe  Arg  Glu  Ile  Ile  Lys  Pro  Ala
               115                    120                    125

( 2 ) INFORMATION FOR SEQ ID NO:17:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Glu Lys Ser Leu His Glu Lys Leu Lys Gln Asp Lys Arg Phe Ser Thr
 1               5                  10                  15
Phe Leu Ser Leu Leu Glu Ala Ala Asp Leu Lys Glu Leu Leu Thr Gln
            20                  25                  30
Pro Gly Asp Trp Thr Leu Phe Val Pro Thr Asn Asp Ala Phe Lys Gly
        35                  40                  45
Met Thr Ser Glu Glu Lys Glu Ile Leu Ile Arg Asp Lys Asn Ala Leu
    50                  55                  60
Gln Asn Ile Ile Leu Tyr His Leu Thr Pro Gly Val Phe Ile Gly Lys
65                  70                  75                  80
Gly Phe Glu Pro Gly Val Thr Asn Ile Leu Lys Thr Thr Gln Gly Ser
                85                  90                  95
Lys Ile Phe Leu Lys Glu Val Asn Asp Thr Leu Leu Val Asn Glu Leu
               100                 105                 110
Lys Ser Lys Glu Ser Asp Ile Met Thr Thr Asn Gly Val Ile His Val
           115                 120                 125
Val Asp Lys Leu Leu Tyr Pro Ala
    130                 135
```

( 2 ) INFORMATION FOR SEQ ID NO:18:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Ala Ala Ala Ala Asp Leu Ala Asp Lys Leu Arg Asp Asp Ser Glu Leu
 1               5                  10                  15
Ser Gln Phe Tyr Ser Leu Leu Glu Ser Asn Gln Ile Ala Asn Ser Thr
            20                  25                  30
Leu Ser Leu Arg Ser Cys Thr Ile Phe Val Pro Thr Asn Glu Ala Phe
        35                  40                  45
Gln Arg Tyr Lys Ser Lys Thr Ala His Val Leu Tyr His Ile Thr Thr
    50                  55                  60
Glu Ala Tyr Thr Gln Lys Arg Leu Pro Asn Thr Val Ser Ser Asp Met
65                  70                  75                  80
Ala Gly Asn Pro Pro Leu Tyr Ile Thr Lys Asn Ser Asn Gly Asp Ile
                85                  90                  95
Phe Val Asn Asn Ala Arg Ile Ile Pro Ser Leu Ser Val Glu Thr Asn
               100                 105                 110
Ser Asp Gly Lys Arg Gln Ile Met His Ile Ile Asp Glu Val Leu Glu
           115                 120                 125
Pro Leu
    130
```

( 2 ) INFORMATION FOR SEQ ID NO:19:

( i ) SEQUENCE CHARACTERISTICS:
    ( A ) LENGTH: 154 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

```
Asn Pro Asn Ala Leu Lys Phe Leu Lys Asn Ala Glu Glu Phe Asn Val
 1               5                  10                  15
Asp Asn Ile Gly Val Arg Thr Tyr Arg Ser Gln Val Thr Met Ala Lys
             20                  25                  30
Lys Glu Ser Val Tyr Asp Ala Ala Gly Gln His Thr Phe Leu Val Pro
         35                  40                  45
Val Asp Glu Gly Phe Lys Leu Ser Ala Arg Ser Ser Leu Val Asp Gly
     50                  55                  60
Lys Val Ile Asp Gly His Val Ile Pro Asn Thr Val Ile Phe Thr Ala
 65                  70                  75                  80
Ala Ala Gln His Asp Asp Pro Lys Ala Ser Ala Ala Phe Glu Asp Leu
                 85                  90                  95
Leu Lys Val Thr Val Ser Phe Phe Lys Gln Lys Asn Gly Lys Met Tyr
             100                 105                 110
Val Lys Ser Asn Thr Ile Val Gly Asp Ala Lys His Arg Val Gly Val
             115                 120                 125
Val Leu Ala Glu Ile Val Lys Ala Asn Ile Pro Val Ser Asn Gly Val
     130                 135                 140
Val His Leu Ile His Arg Pro Leu Met Ile
145                 150
```

( 2 ) INFORMATION FOR SEQ ID NO:20:

( i ) SEQUENCE CHARACTERISTICS:
        ( A ) LENGTH: 154 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Ile Asp Thr Thr Val Thr Gln Phe Leu Gln Ser Phe Lys Glu Asn Ala
 1               5                  10                  15
Glu Asn Gly Ala Leu Arg Lys Phe Tyr Glu Val Ile Met Asp Asn Gly
             20                  25                  30
Gly Ala Val Leu Asp Asp Ile Asn Ser Leu Thr Glu Val Thr Ile Leu
         35                  40                  45
Ala Pro Ser Asn Glu Ala Trp Asn Ser Ser Asn Ile Asn Asn Val Leu
     50                  55                  60
Arg Asp Arg Asn Lys Met Arg Gln Ile Leu Asn Met His Ile Ile Lys
 65                  70                  75                  80
Asp Arg Leu Asn Val Asp Lys Ile Arg Gln Lys Asn Ala Asn Leu Ile
                 85                  90                  95
Ala Gln Val Pro Thr Val Asn Asn Asn Thr Phe Leu Tyr Phe Asn Val
             100                 105                 110
Arg Gly Glu Gly Ser Asp Thr Val Ile Thr Val Glu Gly Gly Gly Val
             115                 120                 125
Asn Ala Thr Val Ile Gln Ala Asp Val Ala Gln Thr Asn Gly Tyr Val
     130                 135                 140
His Ile Ile Asp His Val Leu Gly Val Pro
```

145 150

( 2 ) INFORMATION FOR SEQ ID NO:21:

( i ) SEQUENCE CHARACTERISTICS:
    ( A ) LENGTH: 153 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:21:

| Tyr | Thr | Thr | Val | Leu | Gly | Lys | Leu | Glu | Ser | Asp | Pro | Met | Met | Ser | Asp |
|---|---|---|---|---|---|---|---|---|---|---|---|---|---|---|---|
| 1 | | | | 5 | | | | | 10 | | | | | 15 | |
| Thr | Tyr | Lys | Met | Gly | Lys | Phe | Ser | His | Phe | Asn | Asp | Gln | Leu | Asn | Asn |
| | | | 20 | | | | | 25 | | | | | 30 | | |
| Thr | Gln | Arg | Arg | Phe | Thr | Tyr | Phe | Val | Pro | Arg | Asp | Lys | Gly | Trp | Gln |
| | | | 35 | | | | | 40 | | | | | 45 | | |
| Lys | Thr | Glu | Leu | Asp | Tyr | Pro | Ser | Ala | His | Lys | Lys | Leu | Phe | Met | Ala |
| | | | 50 | | | | | 55 | | | | | 60 | | |
| Asp | Phe | Ser | Tyr | His | Ser | Lys | Ser | Ile | Leu | Glu | Arg | His | Leu | Ala | Ile |
| 65 | | | | | 70 | | | | | 75 | | | | | 80 |
| Ser | Asp | Lys | Glu | Tyr | Thr | Met | Lys | Asp | Leu | Val | Lys | Phe | Ser | Gln | Glu |
| | | | | 85 | | | | | 90 | | | | | 95 | |
| Ser | Gly | Ser | Val | Ile | Leu | Pro | Thr | Phe | Arg | Asp | Ser | Leu | Ser | Ile | Arg |
| | | | | 100 | | | | | 105 | | | | | 110 | |
| Val | Glu | Glu | Glu | Ala | Gly | Arg | Tyr | Val | Ile | Ile | Trp | Asn | Tyr | Lys | Lys |
| | | | 115 | | | | | 120 | | | | | 125 | | |
| Ile | Asn | Val | Tyr | Arg | Pro | Asp | Val | Glu | Cys | Thr | Asn | Gly | Ile | Ile | His |
| | | 130 | | | | | 135 | | | | | 140 | | | |
| Val | Ile | Asp | Tyr | Pro | Leu | Leu | Glu | Glu | | | | | | | |
| 145 | | | | | 150 | | | | | | | | | | |

( 2 ) INFORMATION FOR SEQ ID NO:22:

( i ) SEQUENCE CHARACTERISTICS:
    ( A ) LENGTH: 811 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:22:

| Met | Val | Pro | Leu | Leu | Pro | Leu | Tyr | Ala | Leu | Leu | Leu | Leu | Phe | Leu | Cys |
|---|---|---|---|---|---|---|---|---|---|---|---|---|---|---|---|
| 1 | | | | 5 | | | | | 10 | | | | | 15 | |
| Asp | Ile | Asn | Pro | Ala | Asn | Ala | Asn | Ser | Tyr | Tyr | Asp | Lys | Val | Leu | Ala |
| | | | 20 | | | | | 25 | | | | | 30 | | |
| His | Ser | Arg | Ile | Arg | Gly | Arg | Asp | Gln | Gly | Pro | Asn | Val | Cys | Ala | Leu |
| | | | 35 | | | | | 40 | | | | | 45 | | |
| Gln | Gln | Ile | Leu | Gly | Thr | Lys | Lys | Lys | Tyr | Phe | Ser | Ser | Cys | Lys | Asn |
| | | | 50 | | | | | 55 | | | | | 60 | | |
| Trp | Tyr | Gln | Gly | Ala | Ile | Cys | Gly | Lys | Lys | Thr | Thr | Val | Leu | Tyr | Glu |
| 65 | | | | | 70 | | | | | 75 | | | | | 80 |
| Cys | Cys | Pro | Gly | Tyr | Met | Arg | Met | Glu | Gly | Met | Lys | Gly | Cys | Pro | Ala |
| | | | | 85 | | | | | 90 | | | | | 95 | |
| Val | Met | Pro | Ile | Asp | His | Val | Tyr | Gly | Thr | Leu | Gly | Ile | Val | Gly | Ala |
| | | | | 100 | | | | | 105 | | | | | 110 | |
| Thr | Thr | Thr | Gln | His | Tyr | Ser | Asp | Val | Ser | Lys | Leu | Arg | Glu | Glu | Ile |
| | | | 115 | | | | | 120 | | | | | 125 | | |

```
Glu Gly Lys Gly Ser Tyr Thr Tyr Phe Ala Pro Ser Asn Glu Ala Trp
    130             135                 140
Glu Asn Leu Asp Ser Asp Ile Arg Arg Gly Leu Glu Asn Asn Val Asn
145             150                 155                     160
Val Glu Leu Leu Asn Ala Leu His Ser His Met Val Asn Lys Arg Met
                165             170                 175
Leu Thr Lys Asp Leu Lys His Gly Met Val Ile Pro Ser Met Tyr Asn
            180             185                     190
Asn Leu Gly Leu Phe Ile Asn His Tyr Pro Asn Gly Val Val Thr Val
        195                 200             205
Asn Cys Ala Arg Val Ile His Gly Asn Gln Ile Ala Thr Asn Gly Val
    210                 215                 220
Val His Val Ile Asp Arg Val Leu Thr Gln Ile Gly Thr Ser Ile Gln
225             230                 235                     240
Asp Phe Leu Glu Ala Glu Asp Leu Ser Ser Phe Arg Ala Ala Ala
            245                 250                 255
Ile Thr Ser Asp Leu Leu Glu Ser Leu Gly Arg Asp Gly His Phe Thr
            260             265                 270
Leu Phe Ala Pro Thr Asn Glu Ala Phe Glu Lys Leu Pro Arg Gly Val
    275                 280                 285
Leu Glu Arg Ile Met Gly Asp Lys Val Ala Ser Glu Ala Leu Met Lys
    290             295                 300
Tyr His Ile Leu Asn Thr Leu Gln Cys Ser Glu Ala Ile Thr Gly Gly
305             310                 315                     320
Ala Val Phe Glu Thr Met Glu Gly Asn Thr Ile Glu Ile Gly Cys Glu
                325                 330                 335
Gly Asp Ser Ile Ser Ile Asn Gly Ile Lys Met Val Asn Lys Lys Asp
            340                 345                 350
Ile Val Thr Lys Asn Gly Val Ile His Leu Ile Asp Glu Val Leu Ile
            355                 360             365
Pro Asp Ser Ala Lys Gln Val Ile Glu Leu Ala Gly Lys Gln Gln Thr
    370                 375                 380
Thr Phe Thr Asp Leu Val Ala Gln Leu Gly Leu Ala Ser Ser Leu Lys
385             390                 395                     400
Pro Asp Gly Glu Tyr Thr Leu Leu Ala Pro Val Asn Asn Ala Phe Ser
                405                 410                 415
Asp Asp Thr Leu Ser Met Asp Gln Arg Leu Leu Lys Leu Ile Leu Gln
            420                 425                 430
Asn His Ile Leu Lys Val Lys Val Gly Leu Ser Asp Leu Tyr Asn Gly
        435                 440                 445
Gln Ile Leu Glu Thr Ile Gly Gly Lys Gln Leu Arg Val Phe Val Tyr
    450                 455                 460
Arg Thr Ala Ile Cys Ile Glu Asn Ser Cys Met Val Arg Gly Ser Lys
465                 470                 475                 480
Gln Gly Arg Asn Gly Ala Ile His Ile Phe Arg Glu Ile Ile Gln Pro
                485                 490                 495
Ala Glu Lys Ser Leu His Asp Lys Leu Arg Gln Asp Lys Arg Phe Ser
            500                 505                 510
Ile Phe Leu Ser Leu Leu Glu Ala Ala Asp Leu Lys Asp Leu Leu Thr
        515                 520                 525
Gln Pro Gly Asp Trp Thr Leu Phe Ala Pro Thr Asn Asp Ala Phe Lys
    530                 535                 540
Gly Met Thr Ser Glu Glu Arg Glu Leu Leu Ile Gly Asp Lys Asn Ala
545                 550                 555                 560
```

| | | | | | | | | | | | | | | | |
|---|---|---|---|---|---|---|---|---|---|---|---|---|---|---|---|
|Leu|Gln|Asn|Ile|Ile 565|Leu|Tyr|His|Leu 570|Thr|Pro|Gly|Val|Tyr|Ile 575|Gly|
|Lys|Gly|Phe|Glu 580|Pro|Gly|Val|Thr|Asn 585|Ile|Leu|Lys|Thr|Thr 590|Gln|Gly|
|Ser|Lys|Ile 595|Tyr|Leu|Lys|Gly|Val 600|Asn|Glu|Thr|Leu|Leu 605|Val|Asn|Glu|
|Leu|Lys 610|Ser|Lys|Glu|Ser|Asp 615|Ile|Met|Thr|Thr|Asn 620|Gly|Val|Ile|His|
|Val 625|Val|Asp|Lys|Leu|Leu 630|Tyr|Pro|Ala|Asp|Ile 635|Pro|Val|Gly|Asn|Asp 640|
|Gln|Leu|Leu|Glu|Leu 645|Leu|Asn|Lys|Leu|Ile 650|Lys|Tyr|Ile|Gln|Ile 655|Lys|
|Phe|Val|Arg|Gly 660|Ser|Thr|Phe|Lys|Glu 665|Ile|Pro|Met|Thr|Val 670|Tyr|Arg|
|Pro|Ala|Met 675|Thr|Lys|Ile|Gln|Ile 680|Glu|Gly|Asp|Pro|Asp 685|Phe|Arg|Leu|
|Ile|Lys 690|Glu|Gly|Glu|Thr|Val 695|Thr|Glu|Val|Ile|His 700|Gly|Glu|Pro|Val|
|Ile 705|Lys|Lys|Tyr|Thr|Lys 710|Ile|Ile|Asp|Gly|Val 715|Pro|Val|Glu|Ile|Thr 720|
|Glu|Lys|Gln|Thr|Arg 725|Glu|Glu|Arg|Ile|Ile 730|Thr|Gly|Pro|Glu|Ile 735|Lys|
|Tyr|Thr|Arg|Ile 740|Ser|Thr|Gly|Gly|Gly 745|Glu|Thr|Gly|Glu|Thr 750|Leu|Gln|
|Lys|Phe|Leu 755|Gln|Lys|Glu|Val|Ser 760|Lys|Val|Thr|Lys|Phe 765|Ile|Glu|Gly|
|Gly|Asp 770|Gly|His|Leu|Phe|Glu 775|Asp|Glu|Glu|Ile|Lys 780|Arg|Leu|Leu|Gln|
|Gly 785|Asp|Thr|Pro|Ala|Lys 790|Lys|Ile|Pro|Ala|Asn 795|Lys|Arg|Val|Gln|Gly 800|
|Pro|Arg|Arg|Arg|Ser 805|Arg|Glu|Gly|Arg|Ser 810|Gln| | | | | |

( 2 ) INFORMATION FOR SEQ ID NO:23:

( i ) SEQUENCE CHARACTERISTICS:
( A ) LENGTH: 837 amino acids
( B ) TYPE: amino acid
( D ) TOPOLOGY: linear ( i i ) MOLECULE TYPE: peptide ( x i ) SEQUENCE DESCRIPTION: SEQ ID NO:23:

| | | | | | | | | | | | | | | | |
|---|---|---|---|---|---|---|---|---|---|---|---|---|---|---|---|
|Met 1|Ile|Pro|Phe|Leu 5|Pro|Met|Phe|Ser|Leu 10|Leu|Leu|Leu|Leu|Ile 15|Val|
|Asn|Pro|Ile|Asn 20|Ala|Asn|Asn|His|Tyr 25|Asp|Lys|Ile|Leu|Ala 30|His|Ser|
|Arg|Ile|Arg 35|Gly|Arg|Asp|Gln|Gly 40|Pro|Asn|Val|Cys|Ala 45|Leu|Gln|Gln|
|Ile|Leu 50|Gly|Thr|Lys|Lys|Lys 55|Tyr|Phe|Ser|Thr|Cys 60|Lys|Asn|Trp|Tyr|
|Lys 65|Lys|Ser|Ile|Cys|Gly 70|Gln|Lys|Thr|Thr|Val 75|Leu|Tyr|Glu|Cys|Cys 80|
|Pro|Gly|Tyr|Met|Arg 85|Met|Glu|Gly|Met|Lys 90|Gly|Cys|Pro|Ala|Val 95|Leu|
|Pro|Ile|Asp|His|Val|Tyr|Gly|Thr|Leu|Gly|Ile|Val|Gly|Ala|Thr|Thr|

|     |     |     |     |     |     |     | 100 |     |     |     |     | 105 |     |     |     |     | 110 |     |     |
|-----|-----|-----|-----|-----|-----|-----|-----|-----|-----|-----|-----|-----|-----|-----|-----|-----|-----|-----|-----|

Thr Gln Arg Tyr Ser Asp Ala Ser Lys Leu Arg Glu Glu Ile Glu Gly
            115                 120             125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

|  |  |  |  |  |  |  |  |  |  |  |  |  |  |
|---|---|---|---|---|---|---|---|---|---|---|---|---|---|
| Gly | Asp | Trp | Thr | Leu | Phe | Val | Pro | Thr | Asn | Asp | Ala | Phe | Lys | Gly | Met |
|  | 530 |  |  |  | 535 |  |  |  |  | 540 |  |  |  |
| Thr | Ser | Glu | Glu | Lys | Glu | Ile | Leu | Ile | Arg | Asp | Lys | Asn | Ala | Leu | Gln |
| 545 |  |  |  |  | 550 |  |  |  | 555 |  |  |  |  | 560 |
| Asn | Ile | Ile | Leu | Tyr | His | Leu | Thr | Pro | Gly | Val | Phe | Ile | Gly | Lys | Gly |
|  |  |  |  | 565 |  |  |  |  | 570 |  |  |  |  | 575 |
| Phe | Glu | Pro | Gly | Val | Thr | Asn | Ile | Leu | Lys | Thr | Thr | Gln | Gly | Ser | Lys |
|  |  |  | 580 |  |  |  |  | 585 |  |  |  |  | 590 |
| Ile | Phe | Leu | Lys | Glu | Val | Asn | Asp | Thr | Leu | Leu | Val | Asn | Glu | Leu | Lys |
|  |  | 595 |  |  |  |  | 600 |  |  |  |  | 605 |
| Ser | Lys | Glu | Ser | Asp | Ile | Met | Thr | Thr | Asn | Gly | Val | Ile | His | Val | Val |
|  | 610 |  |  |  |  | 615 |  |  |  |  | 620 |
| Asp | Lys | Leu | Leu | Tyr | Pro | Ala | Asp | Thr | Pro | Val | Gly | Asn | Asp | Gln | Leu |
| 625 |  |  |  |  | 630 |  |  |  |  | 635 |  |  |  |  | 640 |
| Leu | Glu | Ile | Leu | Asn | Lys | Leu | Ile | Lys | Tyr | Ile | Gln | Ile | Lys | Phe | Val |
|  |  |  |  | 645 |  |  |  |  | 650 |  |  |  |  | 655 |
| Arg | Gly | Ser | Thr | Phe | Lys | Glu | Ile | Pro | Val | Thr | Val | Tyr | Arg | Thr | Thr |
|  |  |  | 660 |  |  |  |  | 665 |  |  |  |  | 670 |
| Lys | Ile | Ile | Thr | Lys | Val | Val | Glu | Pro | Lys | Ile | Lys | Val | Ile | Glu | Gly |
|  |  | 675 |  |  |  |  | 680 |  |  |  |  | 685 |
| Ser | Leu | Gln | Pro | Ile | Ile | Lys | Thr | Glu | Gly | Pro | Thr | Leu | Thr | Lys | Val |
|  | 690 |  |  |  |  | 695 |  |  |  | 700 |
| Lys | Ile | Glu | Gly | Glu | Pro | Glu | Phe | Arg | Leu | Ile | Lys | Glu | Gly | Glu | Thr |
| 705 |  |  |  |  | 710 |  |  |  |  | 715 |  |  |  |  | 720 |
| Ile | Thr | Glu | Val | Ile | His | Gly | Glu | Pro | Ile | Ile | Lys | Lys | Tyr | Thr | Lys |
|  |  |  |  | 725 |  |  |  |  | 730 |  |  |  |  | 735 |
| Ile | Ile | Asp | Gly | Val | Pro | Val | Glu | Ile | Thr | Glu | Lys | Glu | Thr | Arg | Glu |
|  |  |  | 740 |  |  |  |  | 745 |  |  |  |  | 750 |
| Glu | Arg | Ile | Ile | Thr | Gly | Pro | Glu | Ile | Lys | Tyr | Thr | Arg | Ile | Ser | Thr |
|  |  | 755 |  |  |  |  | 760 |  |  |  |  | 765 |
| Gly | Gly | Gly | Glu | Thr | Glu | Glu | Thr | Leu | Lys | Lys | Leu | Leu | Gln | Glu | Glu |
|  | 770 |  |  |  |  | 775 |  |  |  |  | 780 |
| Val | Thr | Lys | Val | Thr | Lys | Phe | Ile | Glu | Gly | Gly | Asp | Gly | His | Leu | Phe |
| 785 |  |  |  |  | 790 |  |  |  |  | 795 |  |  |  |  | 800 |
| Glu | Asp | Glu | Glu | Ile | Lys | Arg | Leu | Leu | Gln | Gly | Asp | Thr | Pro | Val | Arg |
|  |  |  |  | 805 |  |  |  |  | 810 |  |  |  |  | 815 |
| Lys | Leu | Gln | Ala | Asn | Lys | Lys | Val | Gln | Gly | Ser | Arg | Arg | Arg | Leu | Arg |
|  |  |  | 820 |  |  |  |  | 825 |  |  |  |  | 830 |
| Glu | Gly | Arg | Ser | Gln |
|  |  |  | 835 |

(2) INFORMATION FOR SEQ ID NO:24:

(i) SEQUENCE CHARACTERISTICS:
    (A) LENGTH: 779 amino acids
    (B) TYPE: amino acid
    (D) TOPOLOGY: linear (ii) MOLECULE TYPE: peptide (xi) SEQUENCE DESCRIPTION: SEQ ID NO:24:

|  |  |  |  |  |  |  |  |  |  |  |  |  |  |  |  |
|---|---|---|---|---|---|---|---|---|---|---|---|---|---|---|---|
| Met | Ile | Pro | Phe | Leu | Pro | Met | Phe | Ser | Leu | Leu | Leu | Leu | Leu | Ile | Val |
| 1 |  |  |  | 5 |  |  |  |  | 10 |  |  |  |  | 15 |
| Asn | Pro | Ile | Asn | Ala | Asn | Asn | His | Tyr | Asp | Lys | Ile | Leu | Ala | His | Ser |
|  |  |  | 20 |  |  |  |  | 25 |  |  |  |  | 30 |
| Arg | Ile | Arg | Gly | Arg | Asp | Gln | Gly | Pro | Asn | Val | Cys | Ala | Leu | Gln | Gln |
|  |  | 35 |  |  |  |  | 40 |  |  |  |  | 45 |

```
Ile Leu Gly Thr Lys Lys Lys Tyr Phe Ser Thr Cys Lys Asn Trp Tyr
     50              55              60
Lys Lys Ser Ile Cys Gly Gln Lys Thr Thr Val Leu Tyr Glu Cys Cys
 65              70              75                       80
Pro Gly Tyr Met Arg Met Glu Gly Met Lys Gly Cys Pro Ala Val Leu
                 85              90                   95
Pro Ile Asp His Val Tyr Gly Thr Leu Gly Ile Val Gly Ala Thr Thr
             100             105             110
Thr Gln Arg Tyr Ser Asp Ala Ser Lys Leu Arg Glu Ile Glu Gly
         115             120             125
Lys Gly Ser Phe Thr Tyr Phe Ala Pro Ser Asn Glu Ala Trp Asp Asn
     130             135             140
Leu Asp Ser Asp Ile Arg Arg Gly Leu Glu Ser Asn Val Asn Val Glu
 145             150             155             160
Leu Leu Asn Ala Leu His Ser His Met Ile Asn Lys Arg Met Leu Thr
                 165             170             175
Lys Asp Leu Lys Asn Gly Met Ile Ile Pro Ser Met Tyr Asn Asn Leu
             180             185             190
Gly Leu Phe Ile Asn His Tyr Pro Asn Gly Val Val Thr Val Asn Cys
         195             200             205
Ala Arg Ile Ile His Gly Asn Gln Ile Ala Thr Asn Gly Val Val His
     210             215             220
Val Ile Asp Arg Val Leu Thr Gln Ile Gly Thr Ser Ile Gln Asp Phe
 225             230             235             240
Ile Glu Ala Glu Asp Asp Leu Ser Ser Phe Arg Ala Ala Ala Ile Thr
                 245             250             255
Ser Asp Ile Leu Glu Ala Leu Gly Arg Asp Gly His Phe Thr Leu Phe
             260             265             270
Ala Pro Thr Asn Glu Ala Phe Glu Lys Leu Pro Arg Gly Val Leu Glu
         275             280             285
Arg Phe Met Gly Asp Lys Val Ala Ser Glu Ala Leu Met Lys Tyr His
     290             295             300
Ile Leu Asn Thr Leu Gln Cys Ser Glu Ser Ile Met Gly Gly Ala Val
 305             310             315             320
Phe Glu Thr Leu Glu Gly Asn Thr Ile Glu Ile Gly Cys Asp Gly Asp
                 325             330             335
Ser Ile Thr Val Asn Gly Ile Lys Met Val Asn Lys Lys Asp Ile Val
             340             345             350
Thr Asn Asn Gly Val Ile His Leu Ile Asp Gln Val Leu Ile Pro Asp
         355             360             365
Ser Ala Lys Gln Val Ile Glu Leu Ala Gly Lys Gln Gln Thr Thr Phe
     370             375             380
Thr Asp Leu Val Ala Gln Leu Gly Leu Ala Ser Ala Leu Arg Pro Asp
 385             390             395             400
Gly Glu Tyr Thr Leu Leu Ala Pro Val Asn Asn Ala Phe Ser Asp Asp
                 405             410             415
Thr Leu Ser Met Val Gln Arg Leu Leu Lys Leu Ile Leu Gln Asn His
             420             425             430
Ile Leu Lys Val Lys Val Gly Leu Asn Glu Leu Tyr Asn Gly Gln Ile
         435             440             445
Leu Glu Thr Ile Gly Gly Lys Gln Leu Arg Val Phe Val Tyr Arg Thr
     450             455             460
Ala Val Cys Ile Glu Asn Ser Cys Met Glu Lys Gly Ser Lys Gln Gly
```

|     | 465 |     |     |     | 470 |     |     |     | 475 |     |     |     | 480 |     |
| --- | --- | --- | --- | --- | --- | --- | --- | --- | --- | --- | --- | --- | --- | --- |
| Arg | Asn | Gly | Ala | Ile<br>485 | His | Ile | Phe | Arg | Glu<br>490 | Ile | Ile | Lys | Pro | Ala<br>495 | Glu |
| Lys | Ser | Leu | His<br>500 | Glu | Lys | Leu | Lys | Gln<br>505 | Asp | Lys | Arg | Phe | Ser<br>510 | Thr | Phe |
| Leu | Ser | Leu<br>515 | Leu | Glu | Ala | Ala | Asp<br>520 | Leu | Lys | Glu | Leu | Leu<br>525 | Thr | Gln | Pro |
| Gly | Asp<br>530 | Trp | Thr | Leu | Phe | Val<br>535 | Pro | Thr | Asn | Asp | Ala<br>540 | Phe | Lys | Gly | Met |
| Thr<br>545 | Ser | Glu | Glu | Lys | Glu<br>550 | Ile | Leu | Ile | Arg | Asp<br>555 | Lys | Asn | Ala | Leu | Gln<br>560 |
| Asn | Ile | Ile | Leu | Tyr<br>565 | His | Leu | Thr | Pro | Gly<br>570 | Val | Phe | Ile | Gly | Lys<br>575 | Gly |
| Phe | Glu | Pro | Gly<br>580 | Val | Thr | Asn | Ile | Leu<br>585 | Lys | Thr | Thr | Gln | Gly<br>590 | Ser | Lys |
| Ile | Phe | Leu<br>595 | Lys | Glu | Val | Asn | Asp<br>600 | Thr | Leu | Leu | Val | Asn<br>605 | Glu | Leu | Lys |
| Ser | Lys<br>610 | Glu | Ser | Asp | Ile | Met<br>615 | Thr | Thr | Asn | Gly | Val<br>620 | Ile | His | Val | Val |
| Asp<br>625 | Lys | Leu | Leu | Tyr | Pro<br>630 | Ala | Asp | Thr | Pro | Val<br>635 | Gly | Asn | Asp | Gln | Leu<br>640 |
| Leu | Glu | Ile | Leu | Asn<br>645 | Lys | Leu | Ile | Lys | Tyr<br>650 | Ile | Gln | Ile | Lys | Phe<br>655 | Val |
| Arg | Gly | Ser | Thr<br>660 | Phe | Lys | Glu | Ile | Pro<br>665 | Val | Thr | Val | Tyr | Lys<br>670 | Pro | Ile |
| Ile | Lys | Lys<br>675 | Tyr | Thr | Lys | Ile | Ile<br>680 | Asp | Gly | Val | Pro | Val<br>685 | Glu | Ile | Thr |
| Glu | Lys<br>690 | Glu | Thr | Arg | Glu | Glu<br>695 | Arg | Ile | Ile | Thr | Gly<br>700 | Pro | Glu | Ile | Lys |
| Tyr<br>705 | Thr | Arg | Ile | Ser | Thr<br>710 | Gly | Gly | Gly | Glu | Thr<br>715 | Glu | Glu | Thr | Leu | Lys<br>720 |
| Lys | Leu | Leu | Gln | Glu<br>725 | Glu | Val | Thr | Lys | Val<br>730 | Thr | Lys | Phe | Ile | Glu<br>735 | Gly |
| Gly | Asp | Gly | His<br>740 | Leu | Phe | Glu | Asp | Glu<br>745 | Glu | Ile | Lys | Arg | Leu<br>750 | Leu | Gln |
| Gly | Asp | Thr<br>755 | Pro | Val | Arg | Lys | Leu<br>760 | Gln | Ala | Asn | Lys | Lys<br>765 | Val | Gln | Gly |
| Ser | Arg<br>770 | Arg | Arg | Leu | Arg | Glu<br>775 | Gly | Arg | Ser | Gln |     |     |     |     |     |

We claim:

1. An isolated mouse OSF-2 protein encoded by the nucleotide sequence from the ATG at position 33 to the CAG at position 2465 of SEQ ID NO:1.

2. An isolated human placenta OSF-2 protein encoded by the nucleotide sequence from the ATG at position 38 to the CAG at position 2374 of SEQ ID NO:3.

3. An isolated human osteosarcoma OSF-2 protein encoded by the nucleotide sequence from the ATG at position 32 to the CAG at position 2539 of SEQ ID NO:5.

4. An antigenic synthetic peptide selected from the group consisting of OSF-2.1, OSF-2.2, OSF-2.3, OSF-2.4 or OSF-2.5.

* * * * *